United States Patent
Vukicevic et al.

(10) Patent No.: US 11,642,437 B2
(45) Date of Patent: May 9, 2023

(54) AUTOLOGOUS BONE GRAFT SUBSTITUTE COMPOSITION COMPRISING BIOCERAMIC PARTICLES OF DIFFERENT GEOMETRY

(71) Applicant: Genera Istraživanja d.o.o., Rakov Potok (HR)

(72) Inventors: Slobodan Vukicevic, Zagreb (HR); Kuber T. Sampath, Holliston, MA (US)

(73) Assignee: Genera Istrazivanja d.o.o.

( * ) Notice: Subject to any disclaimer, the term of this patent is extended or adjusted under 35 U.S.C. 154(b) by 35 days.

(21) Appl. No.: 17/361,937

(22) Filed: Jun. 29, 2021

(65) Prior Publication Data

US 2022/0023494 A1    Jan. 27, 2022

Related U.S. Application Data

(60) Provisional application No. 63/045,367, filed on Jun. 29, 2020.

(51) Int. Cl.
*A61L 27/12* (2006.01)
*A61L 27/22* (2006.01)
*A61L 27/36* (2006.01)

(52) U.S. Cl.
CPC .............. *A61L 27/12* (2013.01); *A61L 27/227* (2013.01); *A61L 27/3616* (2013.01); *A61L 2300/414* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 4,968,590 | A | 11/1990 | Kuberasampath et al. |
| 5,011,691 | A | 4/1991 | Oppermann et al. |
| 5,496,552 | A | 3/1996 | Kuberasampath et al. |
| 5,674,844 | A | 10/1997 | Kuberasampath et al. |
| 6,333,312 | B1 | 12/2001 | Kuberasampath et al. |
| 2017/0106119 | A1* | 4/2017 | Skinner .................. A61L 27/58 |

FOREIGN PATENT DOCUMENTS

WO    2019076484 A1    4/2019

OTHER PUBLICATIONS

Akamaru T, Suh D, Boden SD, Kim HS, Minamide A, Louis-Ugbo J. Simple carrier matrix modifications can enhance delivery of recombinant human bone morphogenetic protein-2 for posterolateral spine fusion. Spine. 2003;28(5):429-34.
Alam MI, Asahina I, Ohmamiuda K, Takahashi K, Yokota S, Enomoto S Evaluation of ceramics composed of different hydroxyapatite to tricalcium phosphate ratios as carriers for rhBMP-2. Biomaterials. 2001;22(12):1643-51.
Albrektsson T, Johansson C. Osteoinduction, osteoconduction and osseointegration. European spine journal: official publication of the European Spine Society, the European Spinal Deformity Society, and the European Section of the Cervical Spine Research Society. 2001;10 Suppl 2: S96-101.
Boden SD, Schimandle JH, Hutton WC. 1995 Volvo Award in basic sciences. The use of an osteoinductive growth factor for lumbar spinal fusion. Part II: Study of dose, carrier, and species. Spine. 1995;20(24):2633-44.
Chu TM, Warden SJ, Turner CH, Stewart RL Segmental bone regeneration using a load-bearing biodegradable carrier of bone morphogenetic protein-2. Biomaterials. 2007;28(3):459-67.
Dimar JR, Glassman SD, Burkus KJ, Carreon LY. Clinical outcomes and fusion success at 2 years of single-level nstrumented posterolateral fusions with recombinant human bone morphogenetic protein-2/ compression resistant matrix versus iliac crest bone graft. Spine. 2006;31(22):2534-9; discussion 40.
Dohzono S, Imai Y, Nakamura H, Wakitani S, Takaoka K. Successful spinal fusion by *E. coli*-derived BMP-2-adsorbed porous beta-TCP granules: a pilot study. Clinical orthopaedics and related research. 2009;467(12):3206-12.
Dorozhkin SV. Bioceramics of calcium orthophosphates. Biomaterials. 2010;31(7):1465-85.
El Bialy I, Jiskoot W, Reza Nejadnik M. Formulation, Delivery and Stability of Bone Morphogenetic Proteins for Effective Bone Regeneration. Pharmaceutical research 2017;34(6):1152-70.
Glassman SD, Dimar JR, Carreon LY, Campbell MJ, Puno RM, Johnson JR. Initial fusion rates with recombinant human bone morphogenetic protein-2/compression resistant matrix and a hydroxyapatite and tricalcium phosphate/collagen carrier in posterolateral spinal fusion. Spine. 2005 ;30(15) :1694-8.
Grgurevic L, Erjavec, I.; Gupta, M.; Pecin, M.; Bordukalo-Niksic, T.; Stokovic, N., et al. Autologous blood coagulum containing rhBMP6 induces new bone formation to promote anterior lumbar interbody fusion (ALIF) and posterolateral umbar fusion (PLF) of spine in sheep. Bone. 2020.

(Continued)

*Primary Examiner* — Robert A Wax
*Assistant Examiner* — Randeep Singh
(74) *Attorney, Agent, or Firm* — St Onge Steward Johnston and Reens LLC

(57) ABSTRACT

An autologous bone graft substitute composition for inducing new bone formation, promoting bone growth and treating bone defects. The composition includes autologous blood; one or more analogs of an osteogenic bone morphogenetic protein selected from BMP-6, BMP-2, BMP-7, BMP-4, BMP-5, BMP-8, BMP-9, BMP-12, and BMP-13, and combinations thereof in a range of from 2 to 1000 μg per ml of autologous blood; and hydroxyapatite, tri-calcium phosphate, or a mixture thereof as a compression resistant matrix, the compression resistant matrix being provided in the form of particles having a particle size in a range of from above 74 to 8000 μm. Preferably, a ratio between the compression resistant matrix and the autologous blood coagulum is from 50 to 500 mg of the compression resistant matrix per mL of the autologous blood coagulum.

26 Claims, 33 Drawing Sheets
(24 of 33 Drawing Sheet(s) Filed in Color)

(56) References Cited

OTHER PUBLICATIONS

Grgurevic L, Oppermann H, Pecin M, Erjavec I, Capak H, Pauk M, et al. Recombinant Human Bone Morphogenetic Protein 6 Delivered Within Autologous Blood Coagulum Restores Critical Size Segmental Defects of Ulna in Rabbits. JBMR plus. 2019;3(5):e10085.

Griffith, Diana L., Peter C. Keck, T.Kuber Sampath,, David C. Rueger, and William D. Carlson. Three-dimensional structure of recombinant human osteogenic protein 1: Structural paradigm for the transforming growth factor b superfamily; Proc Natl Acad Sci USA. 1996; (93) 878-883.

Hoffmann MF, Jones CB, Sietsema DL. Recombinant Human Bone Morphogenetic Protein-2 in Posterolateral Spinal Fusion: What's the Right Dose? Asian spine journal 2016;10(3):457-64.

Itoh H, Ebara S, Kamimura M, Tateiwa Y, Kinoshita T, Yuzawa Y, et al. Experimental spinal fusion with use of recombinant human bone morphogenetic protein 2. Spine. 1999;24(14):1402-5.

Jenis LG, Wheeler D, Parazin SJ, Connolly RJ. The effect of osteogenic protein-1 in instrumented and noninstrumented posterolateral fusion in rabbits. The spine journal: official journal of the North American Spine Society. 2002;2(3):173-8.

Jung UW, Choi SY, Pang EK, Kim CS, Choi SH, Cho KS. The effect of varying the particle size of beta tricalcium phosphate carrier of recombinant human bone morphogenetic protein-4 on bone formation in rat calvarial defects. Journal of periodontology. 2006;77(5):765-72.

Konishi S, Nakamura H, Seki M, Nagayama R, Yamano Y. Hydroxyapatite granule graft combined with recombinant human bone morphogenic protein-2 for solid lumbar fusion. Journal of spinal disorders & techniques. 2002; 15(3):237-44.

Lee JH, Yu CH, Yang JJ, Baek HR, Lee KM, Koo TY, et al. Comparative study of fusion rate induced by different dosages of *Escherichia coli*-derived recombinant human bone morphogenetic protein-2 using hydroxyapatite carrier. The spine journal: official journal of the North American Spine Society. 2012 ; 12(3) :239-48.

Lee SH, Shin H. Matrices and scaffolds for delivery of bioactive molecules in bone and cartilage tissue engineering. Advanced drug delivery reviews. 2007;59(4-5):339-59.

Lee JW, Lee S, Lee SH, Yang HS, Im Gl, Kim CS, et al. Improved spinal fusion efficacy by long-term delivery of bone morphogenetic protein-2 in a rabbit model. Acta orthopaedica 2011;82(6):756-60.

Louis-Ugbo J, Kim HS, Boden SD, Mayr MT, Li RC, Seeherman H, et al. Retention of 125I-labeled recombinant human bone morphogenetic protein-2 by biphasic calcium phosphate or a composite sponge in a rabbit posterolateral spine arthrodesis model. Journal of orthopaedic research: official publication of the Orthopaedic Research Society. 2002;20(5):1050-9.

Massagué J (1998) TGF-? signal transduction. Annu Rev Biochem 67: 753-791.

McKay B. Development of the first commercially available recombinant human bone morphogenetic protein (rhBMP-2) as an autograft replacement for spinal fusion and ongoing R&D direction. In: Vukicevic S & Sampath K, editor. Bone Morphogenetic Proteins: Regeneration of Bone and Beyond. Progress in Inflammation Research. Basel: Birkhäuser; 2004. p. 163-85.

Minamide A, Kawakami M, Hashizume H, Sakata R, Yoshida M, Tamaki T. Experimental study of carriers of bone morphogenetic protein used for spinal fusion. Journal of orthopaedic science: official journal of the Japanese Orthopaedic Association. 2004;9(2):142-51.

Namikawa T, Terai H, Suzuki E, Hoshino M, Toyoda H, Nakamura H, et al. Experimental spinal fusion with recombinant human bone morphogenetic protein-2 delivered by a synthetic polymer and beta-tricalcium phosphate in a rabbit model. Spine. 2005;30(15):1717-22.

Pelletier MH, Oliver RA, Christou C, Yu Y, Bertollo N, Irie H, et al. Lumbar spinal fusion with beta-TCP granules and variable *Escherichia coli*-derived rhBMP-2 dose. The spine journal: official journal of the North American Spine Society. 2014;14(8):1758-68.

Sampath, T.K., A . H. Reddi. Dissociative extraction and reconstitution of extracellular matrix components involved in local bone differentiation. Proc. Natl Acad. Sci. USA vol. 78, No. 12, pp. 7599-7603, 1981.

Sampath, T. Kuber, John E. Coughlin, Robert M. Whetson,David Banach, Clare Corbett, Robert J. Ridge, Engin Uzhaynak, Hermamm Oppermann and David C. Rueger. Bovine Osteogenic Protein Is Composed of Dimers of OP-1 and BMP-2A, Two Members of the Transforming Growth Factor-P Superfamily. The Journal of Biological Chemistry vol. 265, No. 22, pp. 13198-13205, 1990.

Sampath, T. K., N. Muthukamran, A. H. Reddi. Isolation of osteogenin, an extracellular matrix-associated, bone-inductive protein, by heparin affinity chromatography. Proc Nut/. Acad. Sci. USA vol. 84, pp. 7109-7113, 1987.

Seeherman H, Wozney JM. Delivery of bone morphogenetic proteins for orthopedic tissue regeneration. Cytokine & growth factor reviews 2005;16(3):329-45.

Suh DY, Boden SD, Louis-Ugbo J, Mayr M, Murakami H, Kim HS, et al. Delivery of recombinant human bone morphogenetic protein-2 using a compression-resistant matrix in posterolateral spine fusion in the rabbit and in the on-human primate. Spine. 2002;27(4):353-60.

Tazaki J, Murata M, Akazawa T, Yamamoto M, Ito K, Arisue M, et al. BMP-2 release and dose-response studies in hydroxyapatite and beta-tricalcium phosphate. Bio-medical materials and engineering 2009;19(2-3):141-6.

Toth JM, Wang M, Lawson J, Badura JM, DuBose KB. Radiographic, biomechanical, and histological evaluation of rhBMP-2 in a 3-level intertransverse process spine fusion: an ovine study. Journal of neurosurgery Spine. 2016;25(6):733-9.

Tsuruga E, Takita H, Itoh H, Wakisaka Y, Kuboki Y. Pore size of porous hydroxyapatite as the cell-substratum controls BMP-induced osteogenesis. Journal of biochemistry. 1997;121(2):317-24.

Valdes M, Moore DC, Palumbo M, Lucas PR, Robertson A, Appel J, et al. rhBMP-6 stimulated osteoprogenitor cells enhance posterolateral spinal fusion in the New Zealand white rabbit. The spine journal: official journal of the North American Spine Society. 2007;7(3):318-25.

Vukicevic S, Oppermann H, Verbanac D, Jankolija M, Popek I, Curak J, et al. The clinical use of bone morphogenetic proteins revisited: a novel biocompatible carrier device OSTEOGROW for bone healing. International orthopaedics. 2014;38(3):635-47.

Vukicevic S, Grgurevic L, Erjavec I, Pecin M, Bordukalo-Niksic T, Stokovic N, et al. Autologous blood coagulum is a physiological carrier for BMP6 to induce new bone formation and promote posterolateral lumbar spine fusion in rabbits. Journal of tissue engineering and regenerative medicine. 2020;14(1):147-59.

Vukicevic ,Slobodan, Vanja Basic, Dunja Rogic, Nikolina Basic, Mei-Shu Shih, Alyssa Shepard, Don Jin, Bosukonda Dattatreyamurty, William Jones, Haimanti Dorai, Susan Ryan, Denise Griffiths, James Maliakal, Mislav Jelic, Maria Pastorcic, Ana Stavljenic, and T. Kuber Sampath. Osteogenic Protein1 (Bone Morphogenetic Protein 7) Reduces Severity of Injury After Ischemic Acute Renal Failure in Rat. J. Clin. Invest. Volume 102, No. 1, 1998, 202-214.

Wang, Elizabeth A., Vicky Rosen, Paul Cordes, Rodney M. Hewich, Mary Jo Kriz, Deborah P. Luxenbeg, Barbara S. Sibley and John M. Wozeny. Purification and characterization of other distinct bone-inducing factors . Proc. Natl. Acad. Sci. USA 1988. Vol. 85, pp. 9484-9488.

Wang, Elizabeth A., Vicki Rosen, Josephine S. D'Alessandro, Marc Baudry, Paul Cordes, Tomoko Harada, David I. Israel, Rodney M Hewick. ,Kelvin M. Kerns, Peter LaPan, Deborah P. Luxenberg, David McQuaid, Ioannis K. Moutsatos, John Nove and John Wozney. Recombinant human bone morphogenetic protein induces bone formation. Proc. Natl. Acad. Sci. USA vol. 87, pp. 2220-2224, Mar. 1990.

Wozney, John M., Vicki Rosen, Anthony J. Celeste, Lisa M. Mitsock, Matthew J. Whitter, Ronald W. Kriz, Rodney M. Hewick and Elizabeth A. Wang. Novel Regulators of Bone Formation: Molecular Clones and Activities. Proc. Natl. Acad. Sci. USA 85: 9484-9488, 1988.

(56) References Cited

OTHER PUBLICATIONS

Xu H, Shimizu Y, Asai S, Ooya K. Experimental sinus grafting with the use of deproteinized bone particles of different sizes. Clinical oral implants research. 2003;14(5):548-55.

* cited by examiner

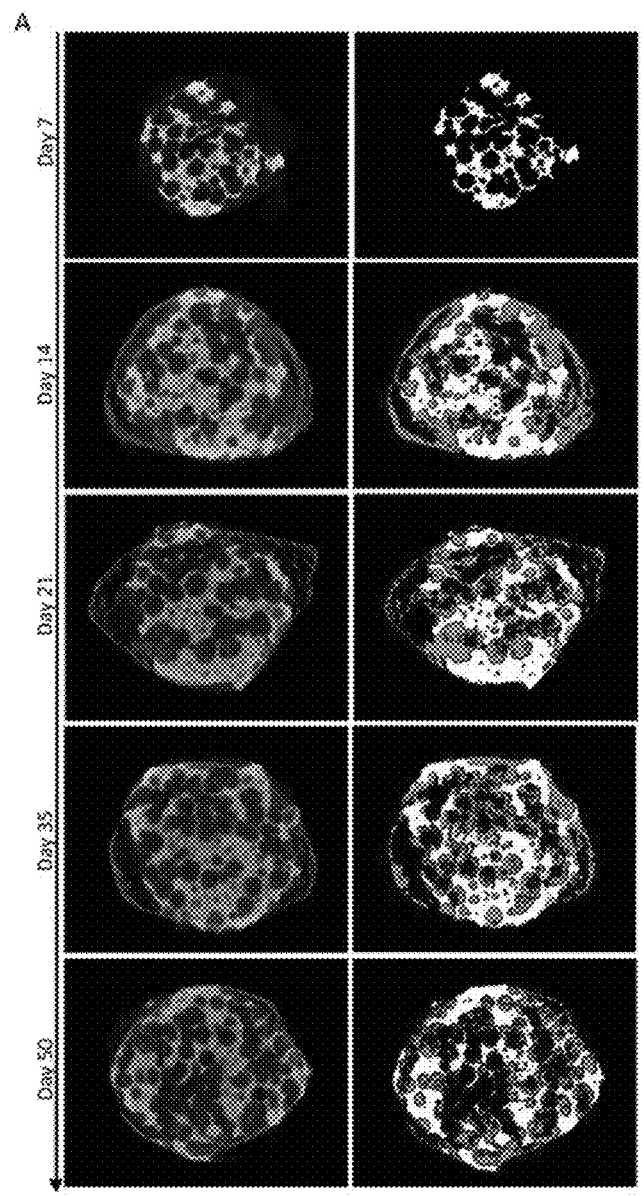
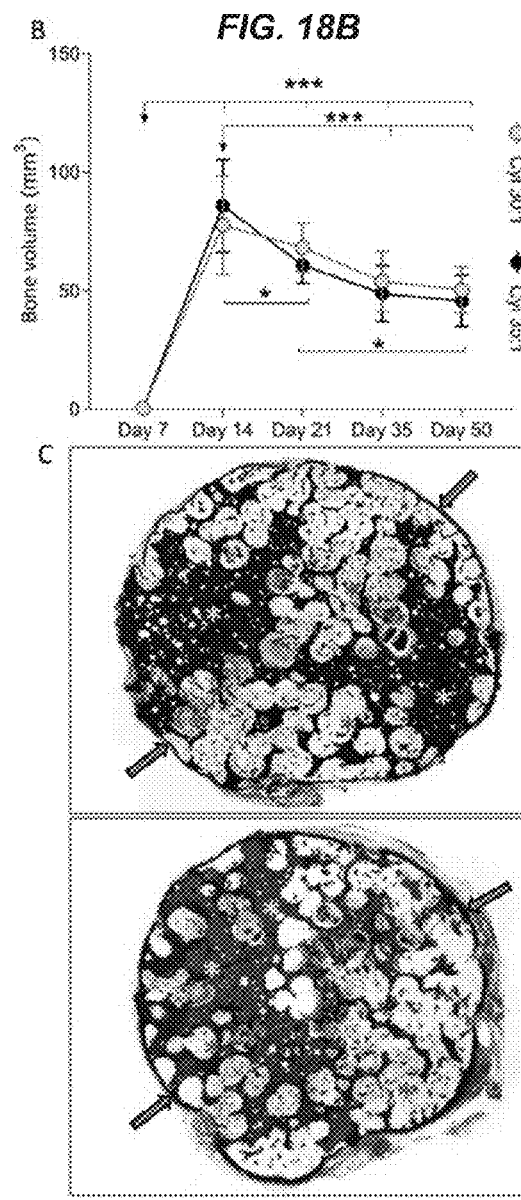
FIG. 18A
FIG. 18B
FIG. 18C

AUTOLOGOUS BONE GRAFT SUBSTITUTE COMPOSITION COMPRISING BIOCERAMIC PARTICLES OF DIFFERENT GEOMETRY

FIELD OF THE INVENTION

The present invention relates to an Autologous Bone Graft Substitute composition comprising bioceramic particles of different geometry, said composition capable of imitating "Live Autograft" for use in treating bone defects, inducing new bone formation and promoting bone growth. In a particular aspect, the invention relates to an implantable Autologous Bone Graft Substitute Composition (hereinafter referred to by abbreviation ABGS) for use in treatment of bone defects, the ABGS comprising bioceramic particles where a surface area, pore volume and particle size of said bioceramic particles having a significant role as a compression resistant matrix (hereafter referred to by CRM) in conjunction with an autologous blood coagulum (hereafter referred to by ABC) as carrier for an osteogenic bone morphogenetic protein (hereinafter referred to by abbreviation BMP) in bone induction, wherein both components CRM and ABC provide a biphasic/multiphasic and extended release of the BMP at the implant site.

BACKGROUND OF THE INVENTION

Bone grafts are employed in a variety of surgical procedures designed to promote growth of new bone to repair a bone defect, augment the bone growth at a particular site, promote fusion of adjacent bones to restore, enhance the stability of a skeletal structure and reduce back and leg pain suffered by an affected individual. In many situations, a surgical procedure employs a bone graft in conjunction with any of a variety of instrumentations, such as pedicle screws and rods, to secure the implanted bone graft and enhance stability while new bone grows to correct the defect.

Posterolateral spinal fusion (PLF) is a commonly performed surgical procedure for the treatment of pathological conditions of the lumbosacral spine including degenerative disc disease, spondylolisthesis, spinal instability and symptomatic scoliosis (1-4). Most spinal arthrodesis procedures consist of an autologous bone graft (autograft; ABG) or an autologous bone graft substitute (ABGS) combined with a posterior instrumentation consisting of pedicle screws and rods (1).

Autografts are currently considered as the gold standard for PLF because they possess inherent osteoconductivity, osteogenicity and osteoinductivity (5-7). However, the use of autografts has several limitations including small amount of bone graft which can be harvested and morbidities associated with the donor site (acute and chronic pain, risk for wound infection, skin scarring and deformity) or secondary surgery (increased blood loss and length of the procedure) (1, 2, 7-10). Therefore, there is an imminent medical need for osteoinductive ABGS, which would replace the use of autografts and provide a safe solution for treatment of patients with spinal pathology. Further, the use of allografts includes the potential for transmission of infectious diseases and rejection due to its immunogenicity.

Bone morphogenetic proteins (BMPs) are well known osteoinductive molecules and their efficacy to achieve posterolateral spinal fusion has been demonstrated in preclinical rabbit, sheep and primate studies (1, 3, 4, 8, 9, 11-20). However, major challenge which still remains unresolved is the development of an optimal carrier/delivery system for BMPs (3). The ideal BMP carrier should be biocompatible, sustain the concentration of the BMP at the treatment site, enable vascular and cellular invasion, define the contours of the resulting bone, prevent ectopic ossification, (19, 21-24) and most importantly maintain its biological and biomechanical function for an extended time period following surgery avoiding thus rapid loss of CRM and favoring a strength comparable to native bone.

BMP carriers might be classified into four major categories: naturally occurring biopolymers, synthetic polymers, inorganic materials and composites of these materials (24, 25). Bovine sourced collagen has been the most widely used BMP carrier in both preclinical studies and clinical practice (25), although it has shown major disadvantages including compressibility, a weak affinity for BMPs thus allowing enhanced release of the protein at the implant site and provoking unwanted safety issues i.e., heterotopic bone formation, and immune reactions needing the use of large BMP doses (8, 11).

From the article "Autologous blood coagulum is a physiological carrier for BMP6 to induce new bone formation and promote posterolateral lumbar spine fusion in rabbits", Journal of tissue engineering and regenerative medicine. 2020; 14(1):147-59, it is known that autologous blood coagulum (ABC) as a physiological native carrier for rhBMP6 effects osteogenesis in various models such as rat subcutaneous sites, rabbit segmental bone defects and anterior lumbar interbody and posterolateral lumbar fusion in rabbit and sheep models (15, 26). Furthermore, it has been demonstrated that ABC suppresses foreign body response elicited by mineral containing compression resistant matrix i.e., allograft, promotes rhBMP6 binding to plasma proteins within the fibrin meshwork, allows a sustained release of rhBMP6 and protects rhBMP6 against generation of antibodies (15, 22, 26). The safety and efficacy outcome obtained from these preclinical studies prompted us to evaluate ABGS (ABC/rhBMP6) containing allograft in randomized controlled clinical trial in patients undergoing PLIF due to the lumbar pain because of degenerative disc disease (EudraCT number 2017-000860-14).

From the WO2019/076484 it is known that a compression resistant matrix (CRM) present in an Autologous Bone Graft Substitute Composition provides a biocompatible scaffold that both structurally supports and is progressively replaced by new bone growth stimulated by the osteogenic BMP component of an implanted autologous bone graft substitute composition. The CRM of WO2019/076484 useful in the autologous bone graft substitute composition includes a bone allograft, a bone autograft, bioresorbable hydrogels, calcium sulfate, synthetic calcium phosphate-carbonate composite such as hydroxyapatite (HA), tri-calcium phosphate (TCP), and combinations thereof. Example #2 of WO2019/076484 provides Allograft, Allogenic bone from donor (ALLO) or Tri-calcium Phosphate (TCP) or TCP and Hydroxyapatite (HA) composite as the CRM without specifying particular particle sizes or ranges thereof. Moreover, in said example ALLO particles were used. Example #3 also shows results with ALLO particles as CRM. Further, Example #4 specifies ALLO particles sizes of from 2-5 mm or 5-8 mm. Further, in Posterolateral Lumbar Fusion (PLF) Study in Rabbits and Posterolateral Lumbar Fusion (PLF) Study in Sheep ALLO particles were used as the CRM.

However, there is no indication in those prior art documents about preferred geometry specifically a particle size range, average pore diameter and total porous volume. Also, it does not mention a ratio between synthetic ceramics (tri-calcium phosphate and hydroxyapatite) and ABC that it can be used in conjunction with an osteogenic BMP in order to achieve a biodegradation (resorption) of ceramics orderly by providing a rate of new bone formation with creeping substitution with a compressive resistance as required to promote a long term sustainability for certain indications.

Aforementioned problems required search of an alternative carrier (8). To address issues related to collagen compressibility, synthetic ceramics such as tri-calcium phosphate (TCP) and hydroxyapatite (HA) have been tested as a compression resistant matrix (CRM) either in combination with collagen (3, 8, 12, 13) or as a stand-alone BMP carrier or in combination with autologous or allogenic bone marrow (11, 14). TCP has shown a faster resorption rate than HA (21). However, strength and speed of resorption might be adjusted using a biphasic ceramic (hereinafter referred to by abbreviation BCP containing both TCP and HA) having a different ratio between TCP to HA (13).

Accordingly, it is the principal object of the present invention to provide an Autologous Bone Graft Substitute Composition having Ca—P based synthetic ceramics as compression resistant matrices with defined particle size and geometry to overcome the above disadvantages associated with a bone autograft or bone allograft.

SUMMARY OF THE INVENTION

It is an object of the present invention to provide an Autologous Bone Graft Substitute Composition comprising synthetic ceramics having preferred particle size range, average pore diameter and total porous volume as a compression resistant matrix (CRM) to substitute devitalized mineralized allograft in conjunction with Autologous Blood Coagulum containing a BMP to promote a bone induction.

Another object of the present invention is to provide an Autologous Bone Graft Substitute Composition comprising bioceramic particles having a particle size in a range of from above 74 to 8000 μm.

To achieve the above object, the present invention relates to an Autologous Bone Graft Substitute Composition providing the features of claim 1.

The advantages of an Autologous Bone Graft Substitute Composition having a compression resistant matrix (CRM) according to the present invention compared to the state-of-the-art compression resistant matrix are the following:

(a) compared to bone allograft, a bone autograft, a bioresorbable polymer or copolymer (e.g., polylactide, polyglycolide, etc.), bioresorbable hydrogels-based compression resistant matrix, the CRM of the present invention is easily and costly manufactured for large scale production;

(b) compared to bone autograft or allograft-based compression resistant matrix, the CRM of the present invention having a particle size in a range of from above 74 to 8000 μm offer the important advantage that the additional, comparatively large particles provide a scaffold enabling vascular and cellular invasion;

(c) compared to bone autograft or allograft-based compression resistant matrix, the CRM of the present invention has more uniform distribution of particles in an autologous blood coagulum; and (d) compared to bone autograft or allograft-based compression resistant matrix, the CRM of the present invention avoids disadvantages that bone allograft possesses, including the potential for transmission of infectious diseases and rejection due to its immunogenicity.

According to a first aspect of the present invention there is provided an Autologous Bone Graft Substitute composition for inducing new bone formation, promoting bone growth and treating of bone defect, wherein the composition comprises:

(i) autologous blood;
(ii) an osteogenic bone morphogenetic protein selected from BMP-6, BMP-2, BMP-7, BMP-4, BMP-5, BMP-8, BMP-9, BMP-12, and BMP-13, analogs thereof or heterodimers thereof, and combinations thereof, in a range of from 2 μg per ml to 1000 μg per mL of autologous blood; and
(iii) hydroxyapatite, tri-calcium phosphate, or a mixture thereof as a compression resistant matrix, the compression resistant matrix comprises particles having a particle size in a range of from above 74 to 8000 μm.

wherein the autologous blood forms an autologous blood coagulum comprising the osteogenic bone morphogenetic protein within fibrin-meshwork and reinforced with the compression resistant matrix, the coagulum gel containing the osteogenic bone morphogenetic protein, whereby the coagulum gel and the compression resistant matrix provide a sustained multiphasic release of the osteogenic bone morphogenetic protein.

In accordance with an embodiment of the invention, a ratio between the compression resistant matrix and the autologous blood coagulum is preferably from 50 to 500 mg of the compression resistant matrix per mL of the autologous blood coagulum.

In accordance with one aspect of the invention, a ratio between the compression resistant matrix and the autologous blood coagulum is of from 100 to 250 mg of the compression resistant matrix per mL of the autologous blood coagulum.

In accordance with one aspect of the invention, an osteogenic bone morphogenetic protein is BMP-6.

In one aspect of the invention, the osteogenic bone morphogenetic protein is BMP-6 or BMP-2 present in a range of from 10 to 100 μg per mL of the autologous blood coagulum.

In another aspect of the invention, the osteogenic bone morphogenetic protein is BMP-6 in the amount of 50 μg per mL of autologous blood.

In another aspect of the invention, the osteogenic bone morphogenetic protein is BMP-6 in the amount of 62.5 μg per mL of autologous blood.

In another aspect of the invention, the osteogenic bone morphogenetic protein is BMP-6 in the amount of 100 μg per mL of autologous blood.

According to one embodiment of the invention, a compression resistant matrix (CRM) is selected from the group consisting of tri-calcium phosphate (TCP) or a biphasic bioceramic (BCP), the biphasic bioceramic (BCP) containing tri-calcium phosphate (TCP) and hydroxyapatite (HA).

According to one embodiment of the invention, a ratio between a compression resistant matrix and an autologous blood coagulum is of from 200 to 500 mg of the compression resistant matrix per 1 mL of the autologous blood coagulum.

In a preferred embodiment of the invention, a particle size is in a range of from above 74 to 420 μm.

In a preferred embodiment of the invention, a particle size is in a range of from 500 to 1700 μm.

In a preferred embodiment of the invention, a particle size is in a range of from 1700 to 2500 μm.

In a further embodiment a particle size is in a range of from 1000 to 4000 μm.

In a further embodiment an average pore diameter of tri-calcium phosphate is in a range of from 320 to 444 µm, and a total porous volume of tri-calcium phosphate is in a range of from 82 to 86%.

In a further embodiment an average pore diameter of a biphasic bioceramic (BCP) containing TCP and HA is in a range of from 356 to 544 µm, and a total porous volume of the biphasic bioceramic (BCP) is in a range of from 86-89%.

In a further embodiment of the present invention, a ratio between tri-calcium phosphate and hydroxyapatite is 80/20.

In another aspect of the present invention, a ratio between tri-calcium phosphate and hydroxyapatite is 60/40.

According to a further embodiment of the present invention there is provided a method of inducing or promoting bone growth by treatment of a bone with an autologous bone graft substitute composition comprising:
 (i) autologous blood;
 (ii) an osteogenic bone morphogenetic protein selected from BMP-6, BMP-2, BMP-7, BMP-4, BMP-5, BMP-8, BMP-9, BMP-12, and BMP-13, analogs thereof or heterodimers thereof, and combinations thereof, in a range of from 2 µg per mL to 1000 µg per mL of autologous blood; and
 (iii) hydroxyapatite, tri-calcium phosphate, or a mixture thereof as a compression resistant matrix, the compression resistant matrix comprises particles having a particle size in a range of from above 74 to 8000 µm,
wherein the autologous blood forms an autologous blood coagulum comprising the osteogenic bone morphogenetic protein within fibrin-meshwork and reinforced with the compression resistant matrix, the coagulum gel containing the osteogenic bone morphogenetic protein, whereby the coagulum gel and the compression resistant matrix provide a sustained multiphasic release of the osteogenic bone morphogenetic protein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 4 shows a µCT analyses of PLF in rabbits, where

FIG. 18A is a series of MicroCT images on day 7, 14, 24, 35 and 50 showing newly formed bone in the BCS.

FIG. 18B is a graph showing new bone volume on day 7, 14, 24, 35 and 50 in the BCS.

FIG. 18C is two histological sections on day 35 showing newly formed bone in the BCS.

DETAILED DESCRIPTION OF THE INVENTION

Figure 1A:
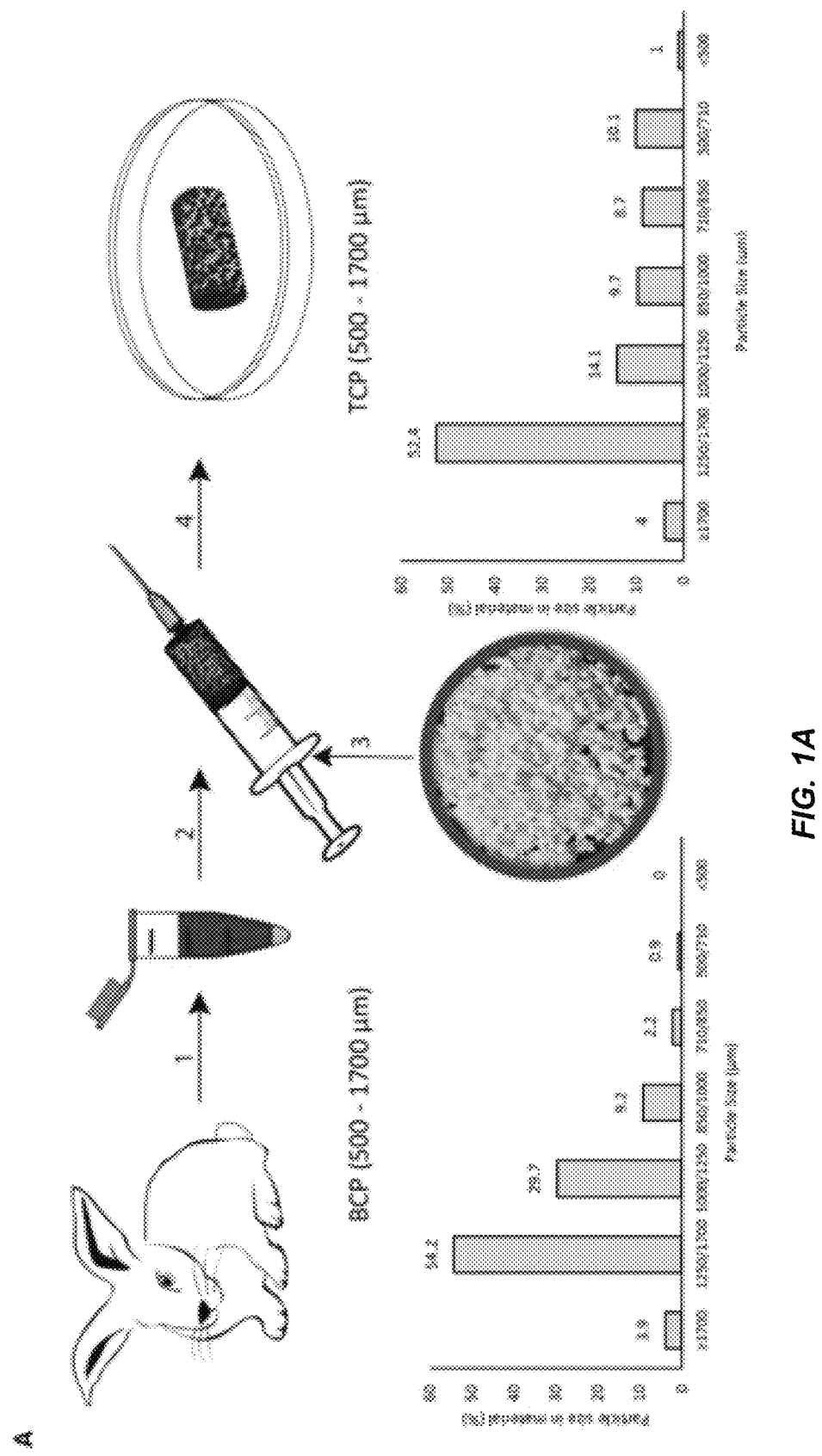
FIG. 1A schematically illustrates a preparation steps of an Autologous Bone Graft Substitute Composition implant and graphs illustrating a distribution of bioceramics particle size fraction.

The disclosure of Applicant's parent patent application, U.S. patent application Ser. No. 16/756,783 filed Apr. 16, 2020, published as US-2020-0237959-A1 on Jul. 30, 2020, and granted as U.S. Pat. No. 10,960,109 on Mar. 30, 2021 is hereby incorporated by reference.

The disclosure of Applicant's parent patent application, U.S. patent application Ser. No. 17/215,843 filed Mar. 29, 2021 is hereby incorporated by reference.

The invention provides an Autologous Bone Graft Substitute Composition (ABGS) for inducing new bone formation, promoting bone growth and treating of bone defect at a desired site. The ABGS of the present invention comprises autologous blood; an osteogenic bone morphogenetic protein selected from BMP-6, BMP-2, BMP-7, BMP-4, BMP-5, BMP-8, BMP-9, BMP-12, and BMP-13, analogs thereof or heterodimers thereof, and combinations thereof, in a range of from 0.002 mg per mL to 1 mg per mL of autologous blood; and hydroxyapatite, tri-calcium phosphate, or a mixture thereof as a compression resistant matrix, the compression resistant matrix comprises a particle size in a range of from above 74 to 8000 μm, wherein the autologous blood forms an autologous blood coagulum comprising the osteogenic bone morphogenetic protein within fibrin-meshwork and reinforced with the compression resistant matrix, in a range of from 50 to 500 mg of the compression resistant matrix per mL of the autologous blood coagulum (hereinafter referred to by abbreviation ABC).

According to one embodiment of the invention, a method of preparation of an autologous bone graft substitute composition, comprising the steps of: mixing a set of components comprising a sample of autologous blood, an osteogenic bone morphogenetic protein (preferably BMP-6), and a compression resistant matrix (CRM). Said components are incubated for a period sufficient to form a biomechanically stable autologous blood coagulum comprising the osteogenic bone morphogenetic protein within fibrin-meshwork and reinforced with the compression resistant matrix.

The period sufficient to form the biomechanically stable autologous blood coagulum comprising the osteogenic bone morphogenetic protein within fibrin-meshwork and reinforced with the compression resistant matrix is 60-90 minutes.

According to another embodiment of the invention, a method of preparation of an autologous bone graft substitute composition, comprising the steps of: mixing the osteogenic bone morphogenic protein BMP (preferably BMP-6) in an aqueous solution with the compression resistant matrix in a sterile lyophilization container wherein a volume of osteogenic bone morphogenic protein aqueous solution added to the compression resistant matrix is optimized for complete wetting of the compression resistant matrix; lyophilization of the osteogenic bone morphogenetic protein BMP (preferably BMP-6) in aqueous solution and the compression resistant matrix; adding autologous blood; and incubating the lyophilized osteogenic bone morphogenetic protein BMP (preferably BMP-6), the compression resistant matrix and autologous blood for a period sufficient to form a biomechanically stable autologous blood coagulum around the lyophilized osteogenic bone morphogenic protein BMP and the compression resistant matrix.

The period sufficient to form the biomechanically stable autologous blood coagulum around the lyophilized osteogenic bone morphogenic protein BMP and the compression resistant matrix is 60-90 minutes.

An ABGS may be prepared by methods described in the international patent application WO2019/076484 and U.S. patent application Ser. No. 17/215,843—Filed Mar. 29, 2021, which are incorporated by reference herein in their entirety.

According to the invention, an ABGS described herein can be readily implanted to a site in which there is a need or desire for a new bone growth.

Definitions

Unless defined otherwise below, all technical and scientific terms used herein have the same meaning as commonly understood by one of ordinary skill in the art to which this invention belongs.

In order that the invention may be more clearly understood, the following terms are defined. The terms "bone morphogenetic protein", "BMP", "osteogenic BMP", and "morphogen" are synonymous and refer to any member of a particular subclass (i.e., the BMP family) of the transforming growth factor □ (TGF-□) super family of proteins (see, e.g., Massagué J (1998) TGF-□ signal transduction. Annu Rev Biochem 67: 753-791; Sampath T K, Rueger D C (1994) Structure, function and orthopedic application of osteogenic protein-1 (OP-1). Complications in Orthopedics 9:101-107 (1994); U.S. Pat. Nos. 4,968,590; 5,011,691; 5,674,844; 6,333,312). All such BMPs have a signal peptide, pro-domain, and a carboxy-terminal (mature) domain. The carboxyl-terminal domain is the mature form of the BMP monomer and contains a highly conserved region characterized by seven cysteines, called "7-Cysteine Domain" a hall mark of BMP-Family proteins that form a cysteine knot (see, Griffith et al., Proc. Natl. Acad. Sci. USA., 93: 878-883 (1996).

BMPs were originally isolated from mammalian bone using protein purification methods (see, e.g., Sampath, et al., Proc. Natl. Acad. Sci. USA 84: 7109-7113 (1987); Wang et al., Proc. Natl. Acad. Sci. USA 85: 9484-9488 (1988); Sampath, et al., J. Biol. Chem. 265: 13198-13205 (1990); U.S. Pat. No. 5,496,552). However, BMPs have also been detected in or isolated from other mammalian tissues and organs including kidney, liver, lung, brain, muscle, teeth, and gut. BMPs may also be produced using standard in vitro recombinant DNA technology for expression in prokaryotic or eukaryotic cell cultures (see, e.g., Wang et al., Proc. Natl. Acad. Sci. USA, 87: 2220-2224 (1990); Wozney et al., Science, 242: 1528-1534 (1988)). Some BMPs are commercially available for local use as well (e.g., BMP-7 is manufactured and distributed for treatment of long bone non-union fractures by Stryker (Kalamazoo, Mich., U.S.). BMP-2 is manufactured and distributed for long bone acute fractures by Wyeth (Madison, N.J., U.S.) and also for spinal fusions in the InFUSE® bone graft that employs a processed bovine Type I collagen sponge carrier in combination with an implantable lordotic threaded cage (LT/CAGE® Lumbar Tapered Fusion Device by Medtronic Sofamor Danek USA, Inc.; Memphis, Tenn., U.S.).

BMPs normally exist as dimers of the same monomeric polypeptides (homodimers) held together by hydrophobic interactions and at least one inter-chain (between monomers) disulfide bond. BMPs useful in the compositions and methods described herein are those that have osteogenic activity, i.e., the ability to stimulate bone formation. Osteogenic (or "osteoinductive") activity may be detected using any of a variety of standard assays. Such osteogenic assays include ectopic bone formation assays in which a carrier matrix comprising collagen and a BMP is implanted at an ectopic site in a rodent and then monitored for bone formation (Sampath T K and Reddi A H Proc. Natl. Acad. Sci. USA, 78: 7599-7603 (1981). In a variation of such an assay, the matrix may be implanted at an ectopic site and the BMP administered to the site, e.g., by intravenous injection into the rodent. Another way to assay for BMP osteogenic activity is to incubate cultured mesenchymal progenitor cells with a BMP and then monitor the cells for differentiation into chondrocytes and/or osteoblasts (see, e.g., Asahina et al., Exp. Cell. Res., 222: 38-47 (1996)). BMPs that have osteogenic activity and that are therefore useful in the compositions and methods described herein include, but are not limited to, BMP-2, BMP-4, BMP-6, BMP-7, BMP-9, BMP-12, BMP-13, and heterodimers thereof, whether purified from a natural source if any, produced recombinant by eukaryotic (e.g., mammalian, yeasts, insects, fish) or prokaryotic (e.g., bacterial) cells, or produced in whole or in part by in vitro protein synthesis methods. A BMP that has an osteogenic activity may also possess one or more other beneficial pharmacological activities, such as the ability to restore or regenerate damaged soft tissues or organs, e.g., ischemic kidneys (Vukicevic et al., J. Clin. Invest., 102: 202-214 (1998).

The term "pharmaceutically acceptable" refers to a material that is not biologically, chemically, or in any other way incompatible with body chemistry and metabolisms and also does not adversely affect the desired, effective activity of an osteogenic BMP or any other component in a composition that may be administered to an individual to promote bone growth according to the invention. one or more named elements or steps also describes the corresponding, more limited, composition or method "consisting essentially of" (or "which consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "which consists of") the named elements or steps to the exclusion of any other unnamed element or step. In any composition or method disclosed herein, known or disclosed equivalents of any named essential element or step may be substituted for that element or step. Unless indicated otherwise, the meaning of other terms is the same as understood and used by persons skilled in the art, including the fields of orthopedic surgeries, medicine, immunology, biochemistry, molecular biology, and tissue regeneration.

As used herein the term "biomechanically stable autologous blood coagulum" refers to an autologous blood coagulum adapted to release BMP at a treatment site in a "sustained release" profile over a period of time. In one aspect, the period of time taken by the autologous blood coagulum to release the at least one BMP is between several days and several weeks. Preferably, the autologous blood coagulum is adapted to release the at least one BMP over a period of weeks. Preferably, the blood coagulum is obtained from "autologous blood".

As used herein the term "multiphasic release" refers to an initial release of the at least one BMP over an initial period of time, followed by "sustained" release of the at least one BMP over a second period of time. Preferably, the initial period of time is roughly over 7 to 10 days and the second period of time is roughly 10 days to weeks. Such a release profile may also be referred to as "biphasic release" since it occurs in two stages. In preferred embodiments, the initial release is provided by an autologous blood coagulum of the invention and the "sustained" release is provided by a compression resistant matrix of the invention.

As used herein the term "compression resistant matrix" refers to a material comprising single or multiple components and is adapted to release at least one BMP at a treatment site in a "sustained release" profile over a period of time. In one aspect, the period of time taken by the compression resistant matrix to release the at least one BMP is between several days and several weeks. Preferably, the compression resistant matrix is adapted to release the at least one BMP over a period of weeks.

The BMP present in an autologous bone graft substitute composition described herein promotes new bone growth from progenitor cells that are present in, or migrate into the defect site where the bone graft substitute is implanted. Any osteogenic bone morphogenetic protein (BMP) may be used in the compositions and methods described herein, including analogs thereof, heterodimers of two BMPs, and combinations (mixtures) of two or more BMPs. Preferred osteogenic BMPs useful in the ABGS described herein include, without limitation, BMP-2, BMP-4, BMP-5, BMP-6, BMP-7, BMP-9, BMP-12, BMP-13, heterodimers thereof, and combinations thereof. Even more preferred for use in a bone graft substitute described herein is an osteogenic BMP selected from BMP-2, BMP-4, BMP-6, BMP-7, analogs thereof, heterodimers thereof, and combinations thereof. Most preferably, the BMP used in the ABGS described herein is BMP-6.

A compression resistant matrix (CRM) present in an autologous bone graft substitute composition described herein provides a biocompatible scaffold that both structurally supports and is progressively replaced by new bone growth stimulated by the osteogenic BMP component of the implanted autologous bone graft substitute composition. The CRM useful in the autologous bone graft substitute composition described herein includes a synthetic calcium phosphate-carbonate composite such as hydroxyapatite (HA), tri-calcium phosphate (TCP), or a mixture thereof such as a biphasic bioceramic (BCP) composed of tri-calcium phosphate and hydroxyapatite having a preferred TCP to HA ratio.

The terms "disorder" and "disease" are synonymous and refer to any pathological condition, irrespective of cause or etiological agent. A "defect" in a bone or other tissue refers to a site of abnormal or deficient tissue growth. A "disease" or "disorder" may be characterized by one or more "defects" in one or more tissues. As used herein, the terms "treatment" and "treating" refer to any regimen that alleviates one or more symptoms or manifestations of a disease or disorder, that inhibits, arrests or reverses (causes regression) of a disease or disorder, or that prevents onsets of a disease or disorder. The term "treatment" includes prophylaxis (prevention) of one or more symptoms or manifestations of a disease, including ameliorating or inhibiting the extent of a symptom or manifestation, including pain, that would otherwise characterize the disease in the absence of the treatment.

A "therapeutically effective amount" is an amount of a compound (for example, osteogenic BMP protein) that promotes bone growth at a desired location and in an amount that is desired for achieving a desired endpoint, such as, but not limited to, a stabilized spinal fusion of adjacent vertebrae, filling of a bone defect with new bone, bridging of distal ends of a bone defect, or correction or rebuilding of an oral or maxillofacial injury or anomaly. Such an endpoint can be determined by following new bone growth through standard methodologies, such as X-rays or visual inspection by an attending surgeon or other skilled practitioner.

A composition or method described herein as "comprising" one or more named elements or steps is open-ended, meaning that the named elements or steps are essential, but other elements or steps may be added within the scope of the composition or method. To avoid prolixity, it is also understood that any composition or method described herein as "comprising" (or "which comprises").

According to the present invention, the effect of combining the CRM and the ABC gel in the present invention is that the BMP from the CRM and bound by the coagulum gel/stable blood fibrin mesh work is slowly released. From the CRM, the BMP is gradually released as the coagulum gel/stable blood coagulum is undergoing dissolution. Hence, this is a two-fold slow-release mechanism, a very gradual slow release to prevent spreading of the BMP into tissues distant from the implant site, wherein the coagulum gel/stable blood plasma protein-fibrin mesh work encapsulates the CRM as an additional barrier against a burst-release. The composition of the present invention has two reservoirs of the BMP in combination with two different BMP binding mechanisms—the binding to the CRM and the binding to plasma proteins of the coagulum gel/stable fibrin mesh, both having relatively high capacity for BMP binding.

According to the present invention, the formation of coagulum gel is achieved within the period from 60 to 90 minutes, with or without an anticoagulant substance in solution, but in the presence of mineral-containing solid CRM to achieve specific rheological properties required for a robust, safe and uniform new bone formation within the implant that is retained at the implant site. The inventive Autologous Blood Coagulum ("ABC") gel composition provides for a sustained release of the osteogenic BMP in an initial release profile over a first time period being over 7-10 days, and the compression resistant matrix is adapted to release the osteogenic bone morphogenetic protein in a sustained release profile over a second time period being 10 days to several to weeks.

The sustained release of the osteogenic BMP from the autologous coagulum gel, in combination with the CRM, are essential for safe and robust new bone formation and for subsequently allowing the CRM to undergo a creeping substitution via physiological bone remodeling. These features of the invention prevent a sudden surge and spreading of the BMP that promotes new bone formation away from the implant site, and thus avoid unwanted safety issues.

The surprising unexpected effect is that combination of ABC, BMP and CRM shows a biphasic/multiphasic and extended release of the BMP enabling new bone formation and creeping substitution of CRM via bone remodeling, and at the same time preventing the spreading of the BMP and new bone formation distant from the implant site. In addition, as the coagulum gel undergoes dissolution at the implant site, the new bone is formed simultaneously and BMP is entrapped within the newly formed bone, which additionally effects osteogenesis.

Further, the surprising unexpected effect of the ABGS composition of the present invention includes optimal amount of the CRM, chemical composition and size of particles of the CRM, a method of BMP application and a lower dose of the BMP in bone induction providing a complete fusion and promoting osseointegration between the transverse processes and new bone when implanted with an autologous bone graft substitute composition described herein.

EXAMPLES

The present invention will now be described by means of the following examples. These examples illustrate the novel findings by the inventors that physical attributes of a compression resistant matrix of the present invention like surface area, pore volume and particle size play a significant role as carrier for BMP in bone induction providing a complete fusion and promoting osseointegration between the transverse processes and new bone when implanted with an autologous bone graft substitute composition described herein.

It will be understood that the examples provided herein are intended solely to illustrate the present invention and not to limit the scope of the invention in any way. Likewise, the invention is not limited to any particular preferred embodiments described herein. Indeed, many modifications and variations of the invention may be apparent to those skilled in the art upon reading the present specification. The invention is therefore to be limited only by the terms of the appended claims, along with the full scope of equivalents to which the claims are entitled.

Bone morphogenetic proteins (BMPs) are well known osteoinductive agents and have an essential role in bone tissue engineering. In order to define optimal properties of a novel autologous bone graft substitute (ABGS) containing rhBMP6 within an autologous blood coagulum (ABC) and bioceramic particles as a compression resistant matrix (CRM) the influence of their chemical composition, size and ratio with ABC on the osteoconductive and osteoinductive properties of ABGS were investigated. A series of rat subcutaneous implant assays were conducted with various ABGS formulations. Tested bioceramic particles included tricalcium phosphate (TCP), hydroxyapatite (HA) and biphasic bioceramic (BCP), containing TCP and HA in 80/20 or 60/40 ratio of different particle sizes (small 74-420 µm, medium 500-1700 µm and large 1000-4000 µm). rhBMP6 was either mixed with ABC or lyophilized on CRM prior to use with ABC. In addition, it has been compared bone induction capacity of ABGS containing large particles and five different CRM/ABC ratios. The experiments were terminated on day 21 and implants were analyzed by µCT, histology and histomorphometry. All tested formulation induced in vivo formation of a bone-ceramic structure (BCS) consisting of newly formed bone guided by bioceramic particle scaffold. µCT analyses revealed that all tested ABGS formulations induced an extensive amount of new ectopic bone. TCP and HA (used individually or combined forming BCP) have shown appropriate osteoconductive properties and based on new formed bone as well as the trabecular parameters it was not possible to determine the superiority of one material to others. Also, there were no obvious differences between the two methods of rhBMP6 application in the bone volume appearance. However, particle size and the geometry defined the structural pattern of BCS. Small particles were surrounded with new bone forming a dense trabecular network. BCS containing medium and large particles consisted of bone present on CRM surface and in the pores, with more pronounced cortical bone on the boundaries and the trabeculae between bioceramic particles. Histomorphometrical analysis revealed that shorter distances between small particles than between medium and large ones correlated with higher bone/bone marrow ratio. Particle size and geometry of the bioceramics in ABC/rhBMP6/CRM implants determined the pattern of the newly formed bone and other microenvironmental structures in the novel ABGS. Altering the size, geometry and distance of the particles used as scaffolds during ectopic bone formation is a powerful tool in obtaining the desired ectopic tissue outcome. Successful bone formation in all tested ABGS formulation with its appendices including distribution of CRM, cellular content of the bone marrow, the ratio between the cortical and trabecular bone and the ratio between the bone and bone marrow all could justify the different properties for their use in complex skeletal indications.

Additionally, a series of rat subcutaneous implant assay experiments has been conducted to determine the biology of bone formation induced by autologous bone graft substitute composition (ABGS) comprised of Bone Morphogenetic Protein (BMP) in autologous blood coagulum (ABC) with bioceramic particles as a compression resistant matrix (CRM). Moreover, this model was used to optimize ABGS composition and to address important issues including optimal amount of the CRM, chemical composition and size of particles, method of BMP application and dose of BMP. In particularly preferred embodiments, the bone morphogenetic protein is recombinant human Bone Morphogenetic Protein 6 (rhBMP6).

ABGS compositions which provided optimal results in rat experiments were tested in rabbit posterolateral lumbar fusion (PLF) model. In these experiments it has been evaluated safety and efficacy of ABGS in this clinically relevant model. Moreover, it has been explored the biology of ABGS-induced bone formation in rabbits and further evaluated the effect of chemical composition and size of particles, method of rhBMP6 application and rhBMP6 dosage on the outcome in PLF model.

Finally, ABGS composition with bioceramic particles in sheep PLF model was evaluated to demonstrate safety and efficacy on larger animals that have spine anatomy resembling humans.

A summary table of the experiments and relevant findings is provided below in Table 1. Each experiment is described separately.

TABLE 1

| Study/Example number/Type/Species | Group/treatment/animals per group | Duration/ rhBMP6 amount per implant | Relevant finding |
|---|---|---|---|
| Example 1 | 1) BCP 500-1700 μm, BCP 1700-2500 μm, two different TCP slabs—high and low porosity | 60 days 125 μg | ABGS implants with BCP 500-1700 μm particles the osseointegration was complete, in the implant containing BCP 1700-2500 μm particles it was moderate, while in implants containing TCP slabs the osseointegration did not occur. |
|  | A) Biphasic bioceramic (BCP) 500-1700 μm + 2.5 mL ABC + 125 μg BMP6; B) Biphasic bioceramic (BCP) 500-1700 μm + 2.5 mL ABC + 125 μg BMP6 (lyophilized on BCP); C) Tri-calcium phosphate bioceramic (TCP) 500-1700 μm + 2.5 mL ABC + 125 μg BMP6; D) Tri-calcium phosphate bioceramic (TCP) 500-1700 μm + 2.5 mL ABC + 125 μg BMP6 (lyophilized on TCP) | 60 days 125 μg of rhBMP6 | ABGS implants with both TCP and BCP yielded a complete fusion as there is no difference in the quality and quantity of bone formed. |
| Example 2 | Chemical composition and particle size: TCP 74-420 + ABC + BMP6 HA 74-420 + ABC + BMP6 BCP 74-420 + ABC + BMP6 TCP 500-1500 + ABC + BMP6 HA 500-1500 + ABC + BMP6 BCP 500-1500 + ABC + BMP6 TCP 1000-4000 + ABC + BMP6 HA 1000-4000 + ABC + BMP6 BCP 1000-4000 + ABC + BMP6 |  | ABGS containing rhBMP6 in ABC combined with bioceramic particles, implanted subcutaneously in the axillary region of rats induced formation of new bone which along with bioceramic particles formed unique, vascularized, complex tissue engineered bone-ceramic structure (BCS). The amount of new bone was extensive in all BCS regardless of the particle size, chemical composition of particles, method of rhBMP6 application and CRM/ABC ratio used in tested ABGS formulations |
|  | Method of rhBMP6 application and particle size: BCP 74-420 μm + ABC + rhBMP6 BCP 74-420 μm + ABC + rhBMP6 (lyophilized on BCP) BCP 74-420 μm + ABC + rhBMP6 (lyophilized on BCP) BCP 1000-1700 μm + ABC + rhBMP6 (lyophilized on BCP) + ABC BCP 1000-4000 μm + ABC + rhBMP6 BCP 1000-4000 μm + ABC + rhBMP6 (lyophilized on BCP) Bioceramic mass/Autologous blood coagulum volume ratio: 25 mg BCP 1000-4000 μm + ABC + BMP6 50 mg BCP 1000-4000 μm + ABC + BMP6 75 mg BCP 1000-4000 μm + ABC + BMP6 | 21 days 20 μg of rhBMP6 | ABGS compositions containing higher CRM/ABC ratios induced more bone than compositions containing lower CRM/ABC ratios |

TABLE 1-continued

| Study/Example number/Type/ Species | Group/treatment/animals per group | Duration/ rhBMP6 amount per implant | Relevant finding |
|---|---|---|---|
| | 100 mg BCP 1000-4000 µm + ABC + BMP6 125 mg BCP 1000-4000 µm + ABC + BMP6 | | |
| Example 3 OPS- 20190529/ Subcutaneous implant assay/ Rats | 1. BCP (TCP/HA 80/20) 74-420 µm + ABGS (rhBMP6 in ABC) (n = 10) 2. BCP (TCP/HA 80/20) 500-1700 µm + ABGS (rhBMP6 in ABC) (n = 10) 3. BCP (TCP/HA 80/20) 1000-4000 µm + ABGS (rhBMP6 in ABC) (n = 10) | 1 week 2 weeks 3 weeks 4 weeks 5 weeks 20 µg of rhBMP6 | ABGS implants with bioceramic particles of different sizes induced formation of newly formed bone which along with particles formed bone-ceramic structure (BCS). Newly formed bone was formed through endochondral and intramembranous pathway. Endochondral pathway was predominant in ABGS implants with larger (>500 µm) particles while between smaller particles (>500 µm) bone was formed primarily through intramembranous ossification. |
| Example 4 OPS- 20191119/ Subcutaneous implant assay/ Rats | 1. BCP (TCP/HA 80/20) macroporous block (30:1) + ABGS (rhBMP6 in ABC) (n = 6) 2. BCP (TCP/HA 80/20) macroporous block (35:1) + ABGS (rhBMP6 in ABC) (n = 6) | 1 week 2 weeks 3 weeks 4 weeks 5 weeks 20 µg of rhBMP6 | ABGS implants with bioceramic macroporous block induced formation of newly formed bone which along with bioceramic cylinders formed bone-ceramic structure (BCS). Newly formed bone was formed predominantly by endochondral ossification. |
| Example 5 OPS- 20190205/ Subcutaneous implant assay/ Rats | 1. ABGS (rhBMP6 in ABC) (n = 10) 2. 25 mg BCP (TCP/HA 80/20) 1000-4000 µm + ABGS (rhBMP6 in ABC) (n = 10) 3. 50 mg BCP (TCP/HA 80/20) 1000-4000 µm + ABGS (rhBMP6 in ABC) (n = 10) 4. 75 mg BCP (TCP/HA 80/20) 1000-4000 µm + ABGS (rhBMP6 in ABC) (n = 10) 5. 100 mg BCP (TCP/HA 80/20) 1000-4000 µm + ABGS (rhBMP6 in ABC) (n = 10) 6. 125 mg BCP (TCP/HA 80/20) 1000-4000 µm + ABGS (rhBMP6 in ABC) (n = 10) | 3 weeks 20 µg of rhBMP6 | The addition of bioceramic particles in the ABGS significantly increased the amount of newly formed bone. The amount of newly formed bone in bone-ceramic structure (BCS) correlated with the increase in amount of used bioceramics. The optimal CRM/ABC ratio was found to be 100-125 mg/500 µL ABC. |
| Example 6 OPS- 20190402/ Subcutaneous implant assay/ Rats | 1. HA 1000-4000 µm + ABGS (rhBMP6 in ABC) (n = 10) 2. HA 500-1500 µm + ABGS (rhBMP6 in ABC) (n = 10) 3. HA 74-420 µm + ABGS (rhBMP6 in ABC) (n = 10) 4. TCP 1000-4000 µm + ABGS (rhBMP6 in ABC) (n = 10) 5. TCP 500-1500 µm + ABGS (rhBMP6 in ABC) (n = 10) | 3 weeks 20 µg of rhBMP6 | The amount and structure of newly formed bone induced by ABGS implants were dependent on the particle size and not on chemical composition of bioceramics. Significantly higher amount of newly formed bone was formed in ABGS implants containing small (74-420 µm) and medium (500-1700 µm) than large (1000-4000 µm) particles. Bone-ceramic structure (BCS) with small particles |

TABLE 1-continued

| Study/Example number/Type/ Species | Group/treatment/animals per group | Duration/ rhBMP6 amount per implant | Relevant finding |
|---|---|---|---|
| | 6. TCP 74-420 µm + ABGS (rhBMP6 in ABC) (n = 10)<br>7. BCP (TCP/HA 80/20) 1000-4000 µm + ABGS (rhBMP6 in ABC) (n = 10)<br>8. BCP (TCP/HA 80/20) 500-1500 µm + ABGS (rhBMP6 in ABC) (n = 10)<br>9. BCP (TCP/HA 80/20) 74-420 µm + ABGS (rhBMP6 in ABC) (n = 10) | | consisted of a dense bone network between the particles while BCS with medium and large particles consisted of cortical bone, bone on the bioceramic surfaces and trabeculae surrounded with abundant bone marrow between the particles. |
| Example 7<br>OPS-20191107/<br>Subcutaneous implant assay/<br>Rats | 1. BCP (TCP/HA 80/20) 74-420 µm + ABGS (rhBMP6 + ABC) (n = 6)<br>2. BCP (TCP/HA 80/20) 74-420 µm + rhBMP6 (lyo) + ABC (n = 6)<br>3. BCP (TCP/HA 80/20) 1000-1700 µm + ABGS (rhBMP6 in ABC) (n = 6)<br>4. BCP (TCP/HA 80/20) 1000-1700 µm + rhBMP6 (lyo) + ABC (n = 6)<br>5. BCP (TCP/HA 80/20) 1000-4000 µm + ABGS (rhBMP6 in ABC) (n = 6)<br>6. BCP (TCP/HA 80/20) 1000-4000 µm + rhBMP6 (lyo) + ABC (n = 6) | 3 weeks/<br>20 µg of rhBMP6 | Two tested methods of rhBMP6 application in ABGS implants (rhBMP6 added directly to blood or rhBMP6 prelyophilized on bioceramic particles) had equivalent outcome regardless of the used particle size of bioceramics. |
| Example 8<br>OPS-20200201/<br>Subcutaneous implant assay/<br>Rats | 1. BCP (TCP/HA 80/20) 1000-1700 µm + ABGS (5 µg BMP2 in ABC)<br>2. BCP (TCP/HA 80/20) 1000-1700 µm + ABGS (20 µg BMP2 in ABC)<br>3. BCP (TCP/HA 80/20) 1000-1700 µm + ABGS (50 µg BMP2 in ABC)<br>4. BCP (TCP/HA 80/20) 1000-1700 µm + ABGS (5 µg BMP6 in ABC)<br>5. BCP (TCP/HA 80/20) 1000-1700 µm + ABGS (20 µg BMP6 in ABC)<br>6. BCP (TCP/HA 80/20) 1000-1700 µm + ABGS (50 µg BMP6 in ABC) | 3 weeks<br>5 µg of BMP2 (groups 1 and 3)<br>20 µg of rhBMP6 (groups 2 and 5)<br>50 µg of rhBMP6 (groups 3 and 6) | ABGS implants containing both rhBMP6 or rhBMP2 induced formation of extensive amount of newly formed bone which along the bioceramic particles formed bone-ceramic structure (BCS). However, when the highest dose (50 µg) was applied rhBMP6 was superior to rhBMP2 |
| Example 9<br>OPS-20200703<br>Biomechanical testing/Rabbit | 1. BCP (TCP/HA 40/60) 74-420 µm + ABC (n = 5)<br>2. BCP (TCP/HA 40/60) 500-1700 µm + ABC (n = 5)<br>C) BCP (TCP/HA 80/20) macroporous blocks 30:1 + ABC (n = 5)<br>D) BCP (TCP/HA 80/20) macroporous blocks 35:1 + ABC (n = 5)<br>5) ABC (n = 5) | | ABGS implants containing bioceramic blocks as CRM have higher stiffness and work but lower elasticity compared to implants with bioceramic particles as CRM or without CRM (ABC alone) |
| Example 10<br>OPS-20190321/<br>Posterolateral spinal fusion/<br>Rabbit | 1. BCP (TCP/HA 80/20) 1700-2500 µm + ABGS (rhBMP6 in ABC) (n = 1)<br>2. BCP (TCP/HA 80/20) 500-1700 µm + ABGS (rhBMP6 in ABC) (n = 1)<br>3. TCP macroporous block (35:1) + ABGS (rhBMP6 in ABC) (n = 1)<br>4. TCP macroporous block (24:1) + ABGS (rhBMP6 in ABC) (n = 1) | 8 weeks<br>125 µg of rhBMP6 | Successful rebridgment and highest amount of newly formed bone was observed in ABGS with 500-1700 µm bioceramic particles while the fusion was unsuccessful in implants containing bioceramic macroporous blocks. |

TABLE 1-continued

| Study/Example number/Type/ Species | Group/treatment/animals per group | Duration/ rhBMP6 amount per implant | Relevant finding |
|---|---|---|---|
| Example 11 OPS-20190604/ Posterolateral spinal fusion/ Rabbit | 1. BCP (TCP/HA 80/20) 500-1700 μm + ABGS (rhBMP6 in ABC) (n = 6) 2. BCP (TCP/HA 80/20) 500-1700 μm + BMP6 (lyo) + ABC (n = 6) 3. TCP 500-1700 μm + ABGS (rhBMP6 in ABC) (n = 6) 4. TCP 500-1700 μm + BMP6 (lyo) + ABC (n = 6) | 7 weeks 125 μg of rhBMP6 | ABGS implants with bioceramics induced successful spinal fusion between adjacent transverse processes in more than 90% cases. Two tested methods of rhBMP6 application in ABGS implants (rhBMP6 added directly to blood or rhBMP6 prelyophilized on bioceramic particles) had equivalent spinal fusion outcome. There was no significant difference in CRM resorption between TCP and BCP (TCP/HA 80/20) after 7 weeks. |
| Example 12 OPS-20191030/ Posterolateral spinal fusion/ Rabbit | 1. TCP 500-1700 μm + ABGS (rhBMP6 in ABC) (n = 4) 2. TCP 500-1700 μm + ABGS (rhBMP6 in ABC) (n = 4) 3. BCP (TCP/HA 80/20) 1000-1700 μm + ABGS (rhBMP6 in ABC) (n = 4) 4. BCP (TCP/HA 80/20) 1000-1700 μm + ABGS (rhBMP6 in ABC) (n = 4) 5. BCP (TCP/HA 80/20) 1000-1700 μm + ABGS (rhBMP6 in ABC) + 50 μg ZA (n = 4) | 14 weeks 125 μg of rhBMP6 (groups 1, 3 and 5) 250 μg of rhBMP6 (groups 2 and 4) | ABGS implants with bioceramics induced successful bilateral spinal fusion between adjacent transverse processes in all rabbits (success rate 100%). There was no difference between different BMP doses (125 and 250 μg) neither in the amount of newly formed bone nor spinal fusion success rate. TCP particles were significantly more resorbed than BCP (TCP/HA 80/20) particles after 14 weeks. |
| Example 13 OPS-20200610/ Posterolateral spinal fusion/ Rabbit | 1. TCP 500-1700 μm + ABGS (rhBMP6 in ABC) (n = 6) 2. TCP 74-420 μm + ABGS (rhBMP6 in ABC) (n = 6) 3. BCP (TCP/HA 40/60) 500-1700 μm + ABGS (rhBMP6 in ABC) (n = 6) 4. BCP (TCP/HA 40/60) 74-420 μm + ABGS (rhBMP6 in ABC) (n = 6) | 27 weeks 125 μg of rhBMP6 | ABGS implants with bioceramics induced successful bilateral spinal fusion between adjacent transverse processes in all rabbits (success rate 100%). There was no difference neither in the amount of newly formed bone nor spinal fusion success rate between bioceramics which differ in particle size (74-420 μm and 500-1700 μm). TCP particles were almost completely resorbed while BCP (TCP/HA 40/60) particles were only partially resorbed after 27 weeks. |
| Example 14 OPS-20201111/ Posterolateral spinal fusion/ Sheep | 1. BCP (TCP/HA 40/60) 74-420 μm + ABGS (rhBMP6 in ABC) (n = 1) 2. BCP (TCP/HA 40/60) 500-1700 μm + ABGS (rhBMP6 in ABC) (n = 1) 3. BCP (TCP/HA 80/20) 74-420 μm + ABGS (rhBMP6 in ABC) (n = 9) 4. BCP (TCP/HA 80/20) 500-1700 μm + ABGS (rhBMP6 in ABC) (n = 9) | 21 week (pilot) 27 weeks (pilot) 500 μg of rhBMP6 800 μg of rhBMP6 | ABGS implants with bioceramics (BCP 74-420 or 500-1700 μm) induced successful bilateral spinal fusion between adjacent transverse processes in sheep (success rate 100% in 74-420 μm and 88.8% in 500-1700 μm group). |

Example 1

Example 1 describes testing of four different bioceramic composites (BCP 500-1700 μm, BCP 1700-2500 μm, two different TCP slabs—high and low porosity) in combination with 125 μg rhBMP6 and 2.5 mL ABC (50 μg/mL ABC).

Material and Methods in Posterolateral Lumbar Fusion (PLF) in Rabbits

Prior to in vivo testing bioceramic particles of various sizes of from 74-420 μm to 1700-2500 μm, and slabs were mixed with 2.5 mL of rabbit blood (n=8) to evaluate by μCT and x-ray images the uniformity of ceramic distribution in the ABGS. Since the bioceramic particles below 500 μm was not uniformly distributed in more than 50% specimens (data not shown) following a standardized procedure used for allograft as CRM (15, 26, 27) bioceramic composites of 500 µm and above were used for in vivo experiments.

A first (pilot) PLF rabbit experiment was conducted to test four different bioceramic composites (BCP 500-1700 µm, BCP 1700-2500 µm, two different TCP slabs—high and low porosity) in combination with 125 µg rhBMP6 and 2.5 mL ABC. Observation period in the first experiment was 60 days. Based on the results from the first experiment, a second rabbit experiment was performed in which rhBMP6 was either added to autologous blood and mixed with bioceramic granules or previously lyophilized on bioceramics and then mixed with autologous blood. As the CRM two different types of bioceramics: biphasic bioceramic composed of tri-calcium phosphate and hydroxyapatite (TCP/HA ratio 80/20, particle size 500-1700 µm) and tri-calcium phosphate bioceramics (particle size 500-1700 µm) were used. Quantity and distribution of various particle size fractions among selected bioceramic particle size range (500-1700 µm) is shown in FIG. 1A. The average pore diameter was 356 µm (BCP) and 320 µm (TCP) while the total porous volume was 86% (BCP) and 82% (TCP). White New Zealand rabbits (9 months old, weight 4 kg) were used and assigned to following experimental groups: A) Biphasic bioceramic (BCP) 500-1700 µm+2.5 mL ABC+125 pgBMP6; B) Biphasic bioceramic (BCP) 500-1700 µm+2.5 mL ABC+125 pgBMP6 (lyophilized on BCP); C) Tri-calcium phosphate bioceramic (TCP) 500-1700 µm+2.5 mL ABC+125 pgBMP6; D) Tri-calcium phosphate bioceramic (TCP) 500-1700 µm+2.5 mL ABC+125 pgBMP6 (lyophilized on TCP). Number of samples was 6 per group with an observation period of 50 days. In both experiments the rhBMP6 (Lot No 20160411) produced by Genera Research (Zagreb, Croatia) as previously described (15) was used.

The bioceramic particles features tested are shown in Table 2.

TABLE 2

| Lot Number | Material | Particle Size (mm) | Average Pore Diameter (microns) | Total Porous Volume (%) |
| --- | --- | --- | --- | --- |
| SAMTCP030618A2 | β-TOP Granulate | 0.5-1.7 mm | 320 | 82 |
| SAMBP030718A2 | Biphasic Granulate | 0.5-1.7 mm | 356 | 86 |

Autologous Bone Graft Substitute Composition Preparation

FIG. 1A illustrates a preparation steps of an Autologous Bone Graft Substitute Composition implant preparation and graphs illustrating a distribution of bioceramics particle size fraction. Steps of the ABGS implant preparation are marked with numbers 1 to 4. Blood sample was collected from rabbit marginal ear vein into tube without an anticoagulant substance in a volume of 2.5 mL per implant—step 1. Afterwards blood sample was transferred to the tube with aliquoted solution of rhBMP6—step 2. In step 3 blood sample with rhBMP6 was drawn into the syringe containing the CRM and was left on room temperature to coagulate. Step 4 illustrates a final product (ABGS containing CRM) that is ready for implantation.

Figure 1B:
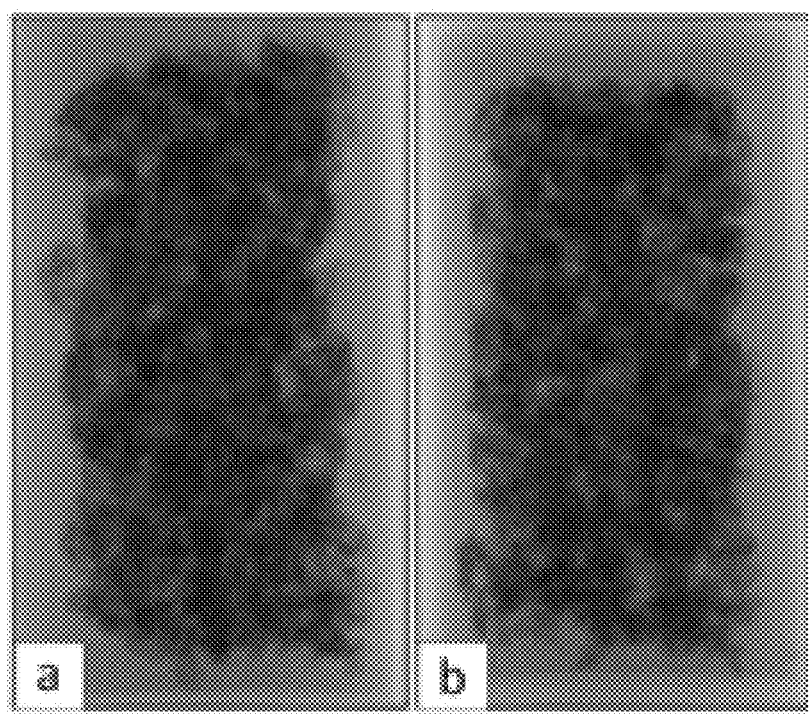
FIG. 1B shows front (a) and lateral (b) CT scan of an Autologous Bone Graft Substitute Composition implant illustrating a distribution of a compression resistant matrix.

Blood samples were collected from rabbit marginal ear vein into tubes without an anticoagulant substance in a volume of 2.5 mL (FIG. 1A). In the first experiment rhBMP6 (125 µg) was mixed with blood and bioceramics, while in the second experiment rhBMP6 (125 µg) was either mixed with blood and bioceramics (group A and C) or lyophilized on bioceramics and then mixed with blood (group B and D). After blood and bioceramics were mixed, the implant was rotated until blood coagulated in order to achieve a uniform distribution of the bioceramic particles. Uniformity of particles distribution was confirmed using x-ray images (FIG. 1B-a and b).

Surgical Procedure and X-Ray Monitoring

The surgery was carried out under general anesthesia and was performed by the same surgical team. The space between transverse processes of the lumbar L5-L6 vertebrae was exposed, and followed by bone decortication. Implants were then placed bilaterally between the transverse processes.

Radiological Monitoring and Analysis

X-ray images of rabbit lumbar spine were taken immediately after surgery (day 0) and at the end of experiments. Lumbar transverse processes and newly formed bone between them were scanned using 1076 SkyScan µCT machine to visualize new ectopic bone formation and to analyze osseointegration on µCT sections. Scanning resolution was set at 18 µm spatial resolution with 0.5 mm aluminium filter and frame averaging set to a value of 2. Due to larger size of specimens the scanning width was set to 68 mm. Acquired images were reconstructed using NRecon software (SkyScan, Belgium). Further assessment and analysis of ectopic bone was done using CTAn software (SkyScan, Belgium). µCT analyses were done on reconstructed µCT images to evaluate the amount of newly formed bone and the amount of unresorbed CRM.

Biomechanical Testing

Following µCT scanning, the region of interest was dissected and lumbar spine was palpated and the mobility of fused transverse processes was tested. After that, three-point bending test was conducted to determine biomechanical parameters (maximum force, work-to-fracture and elasticity) of fusion mass consisting of newly formed bone and adjacent transverse processes. Three-point bending instrument (TA.HDPlus, Stable Micro Systems) used in this study was set with a 50 kg load cell. The fusion mass was placed on the two supports and the measured amount of force was applied perpendicular to the midpoint. Speed was adjusted at 0.5 mm/s, and the force was applied using a single-pronged loading device with flat-tipped wedge.

Histology

Undecalcified histological processing was conducted on selected samples (2 per group) following µCT scanning and fixation in 10% neutral buffered formalin. Specimens were cut by saw in the frontal plane to expose transverse processes and newly formed bone between them. Dehydration of specimens was done in graded solutions of ethyl alcohol (70%/80%/95%/100%) using an automated tissue processing system (ASP300S, Leica Biosystems, Buffalo Grove, Ill., USA). Following dehydration, specimens were cleared manually with methyl salicylate and xylenes before being polymerized into hardened acrylic resin blocks (MMA). Semi-thin microtomed sections (thickness of 5 µm) were collected in the frontal plane using tungsten-carbide knives (D-profile, Delaware Diamond Knives, Wilmington, Del., USA), and an automated sledge microtome (SM2500, Leica Biosystems, Buffalo Grove, Ill., USA). Each section cut was mounted on custom prepared gelatin coated (Haupt's Adhesive) glass microscope slides. Prior to staining, sections were deplasticized and hydrated. Finally, sections were stained with hematoxylin-eosin (H&E), and modified Goldner's trichrome.

Histomorphometry

Quantitative analysis of bone architecture was achieved using histomorphometry which provided valuable information on the amount and the structure of newly formed bone, distribution of compression resistant matrix (CRM) and bone marrow. Histology sections were stained by hematoxylin & eosin (HE), staining the bone light purple, while CRM was colored dark purple. Images were taken using an Olympus microscopy system—Olympus BX53 Upright Microscope equipped with a DP27 camera (5 megapixels, 15 fps) and operated by cellSens Dimension software (Olympus, Japan). HE stained sections were imaged at 10× (1.83 pixel/μm) magnification. The whole area of histological section, the bone area and the area of CRM particles were selected manually and masked with the distinctive color (black) in Photoshop software (Adobe Systems, San Jose, Calif.) in order to be recognized by the measuring software. Masked areas (bone, CRM, whole area) were converted to RGB stacks that were further thresholded and measured in Fiji ImageJ software (version 1.51r; NIH, Maryland, USA). Bone marrow area was calculated as remaining pixels—bone area and CRM area were subtracted from the whole area. Results were expressed as the area percentage.

Data Analysis

Data distribution were analyzed with Kolmogorov-Smirnov test and according to the results and the small sample size appropriate non-parametric tests and data description were used. Differences between groups were processed with Kruskall-Wallis test (all groups together) followed with post-hoc Mann-Whitney U test (comparison between the two groups). The data have been shown in Box and Whisker's plots. P value below 0.05 was considered significant. Statistical software IBM SPSS Statistics, version 25.0 has been used in all statistical procedures.

Results

Selection of Bioceramics Particle Size

Figure 2:
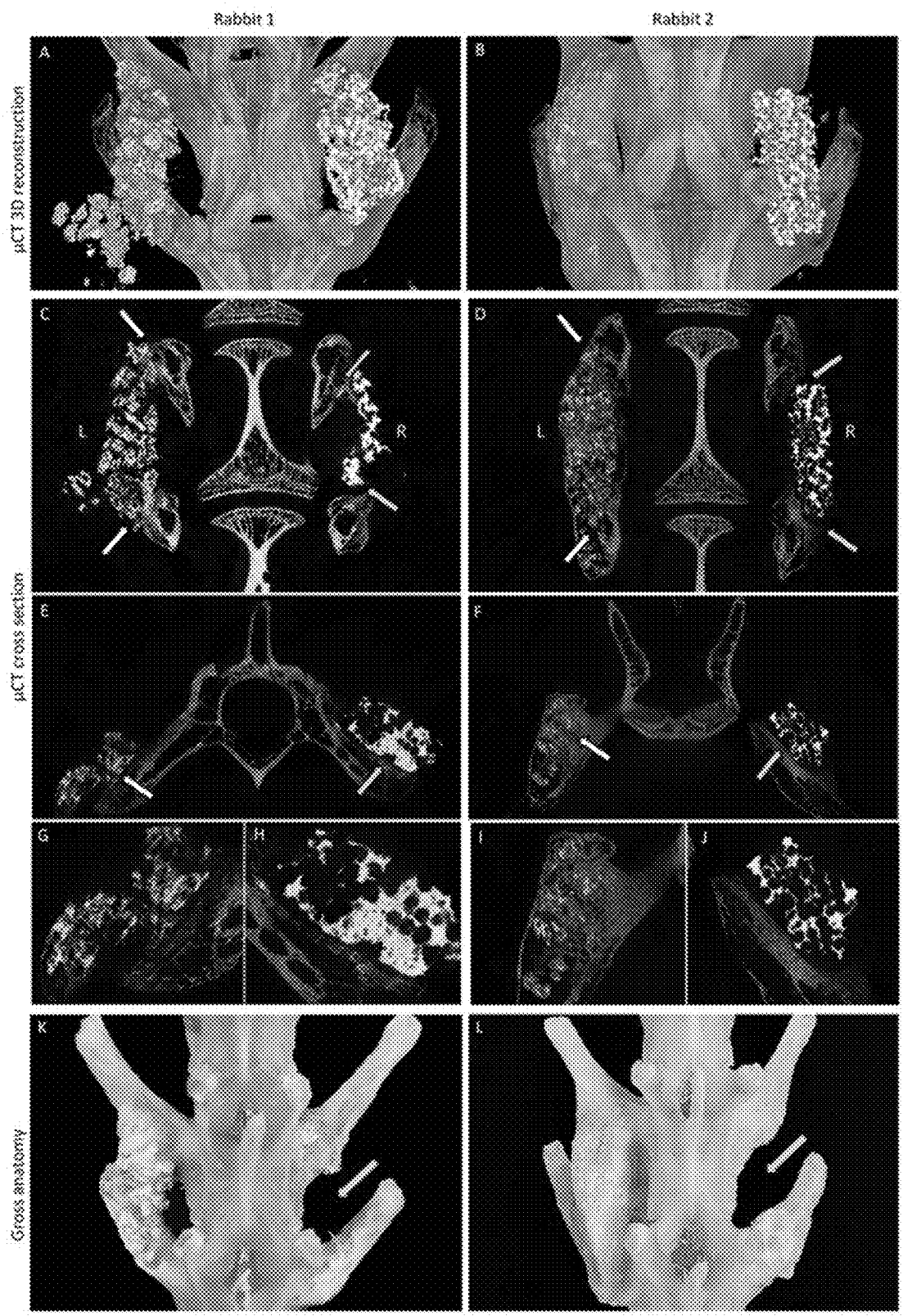
FIG. 2 shows a pCT 3D reconstruction and a gross anatomy of a rabbit spinal fusion (L5-L6).

FIG. 2A-L illustrates results of the rabbit spinal fusion conducted with the ABGS comprising CRM in forms of different bioceramics particle sizes. Rabbit spinal fusion (L5-L6) was conducted with ABGS containing CRM in forms of different size bioceramics particles (500-1700 μm, 1700-2500 μm) of same composition (BCP) and TCP slabs sintered on the same temperature (1175° C.) with different porosity FIGS. 2 A and B illustrate μCT 3D reconstruction indicated successful fusion on the left side, while on the right side where bioceramic slabs were used, the fusion failed. FIGS. 2 C, D and E illustrate μCT cross sections showing successful (white arrow) and failed (yellow arrow) integration of newly formed bone with transverse processes. FIGS. 2G, H, I and J show successful and failed integration showing subject at higher magnification. FIGS. 2 K and L show Gross anatomy of the same specimen. During the bone maceration process, bioceramics slabs on the right side detached (yellow arrows) from the transverse processes since they were not integrated.

In the first experiment rhBMP6 induced bone in all tested formulations containing ABC and synthetic bioceramics. However, the degree of osseointegration of the newly formed bone with the transverse processes was different (FIG. 2A-L). In the implant with BCP 500-1700 μm particles the osseointegration was complete (FIG. 2D, 2F, 2L), in the implant containing BCP 1700-2500 μm particles it was moderate (FIG. 2C, 2E, 2G), while in implants containing TCP slabs the osseointegration did not occur (FIG. 2C-F, 2H, 2J). Moreover, the volume of newly formed bone was highest when 500-1700 μm particles were used.

The obtained results described below refer to the second rabbit experiment.

Spinal Fusion Success Rate and Segmental Mobility Testing

Figure 3A:
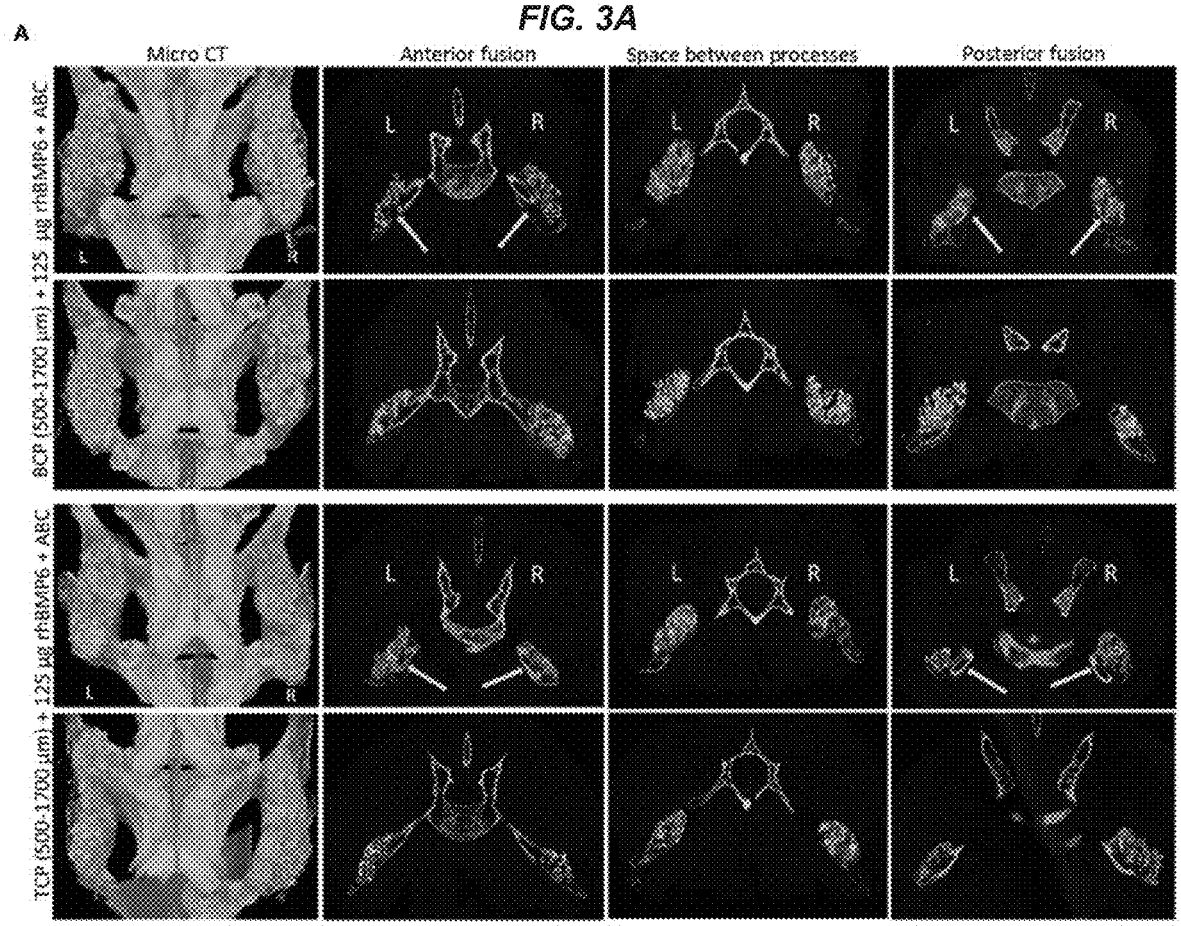
FIG. 3A shows a pCT 3D reconstruction of PLF in rabbits.
Figure 3B:
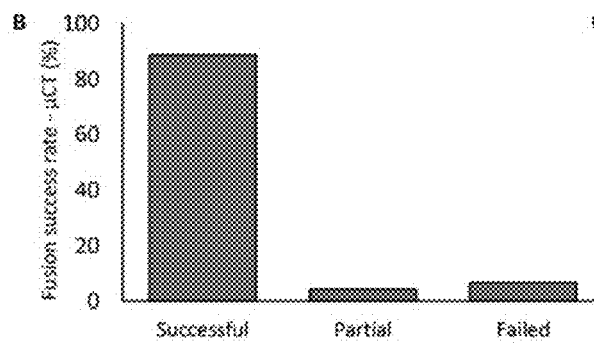
FIG. 3B is a graph illustrating a fusion success rate (%) determined on pCT cross sections through anterior and posterior transverse processes of the rabbits.
Figure 3C:
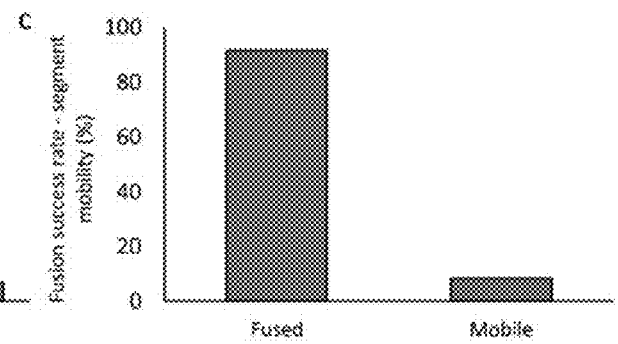
FIG. 3C is a graph illustrating a fusion success rate (%) determined by segmental mobility testing of the rabbits.

FIG. 3A illustrates μCT 3D reconstruction of PLF in rabbits showed successful integration with transverse processes. μCT cross sections through anterior transverse process, space between transverse processes and posterior transverse process of rabbits. L—left side (rhBMP6 applied directly in autologous blood); R—right side (rhBMP6 lyophilized on bioceramics particles); yellow arrows point at fusion site between newly formed bone and the transverse process. FIG. 3B illustrates a fusion success rate (%) determined on μCT cross sections through the anterior and posterior transverse processes, and FIG. 3C illustrates the fusion success rate (%) determined by the segmental mobility testing.

Figures 4A, 4B:
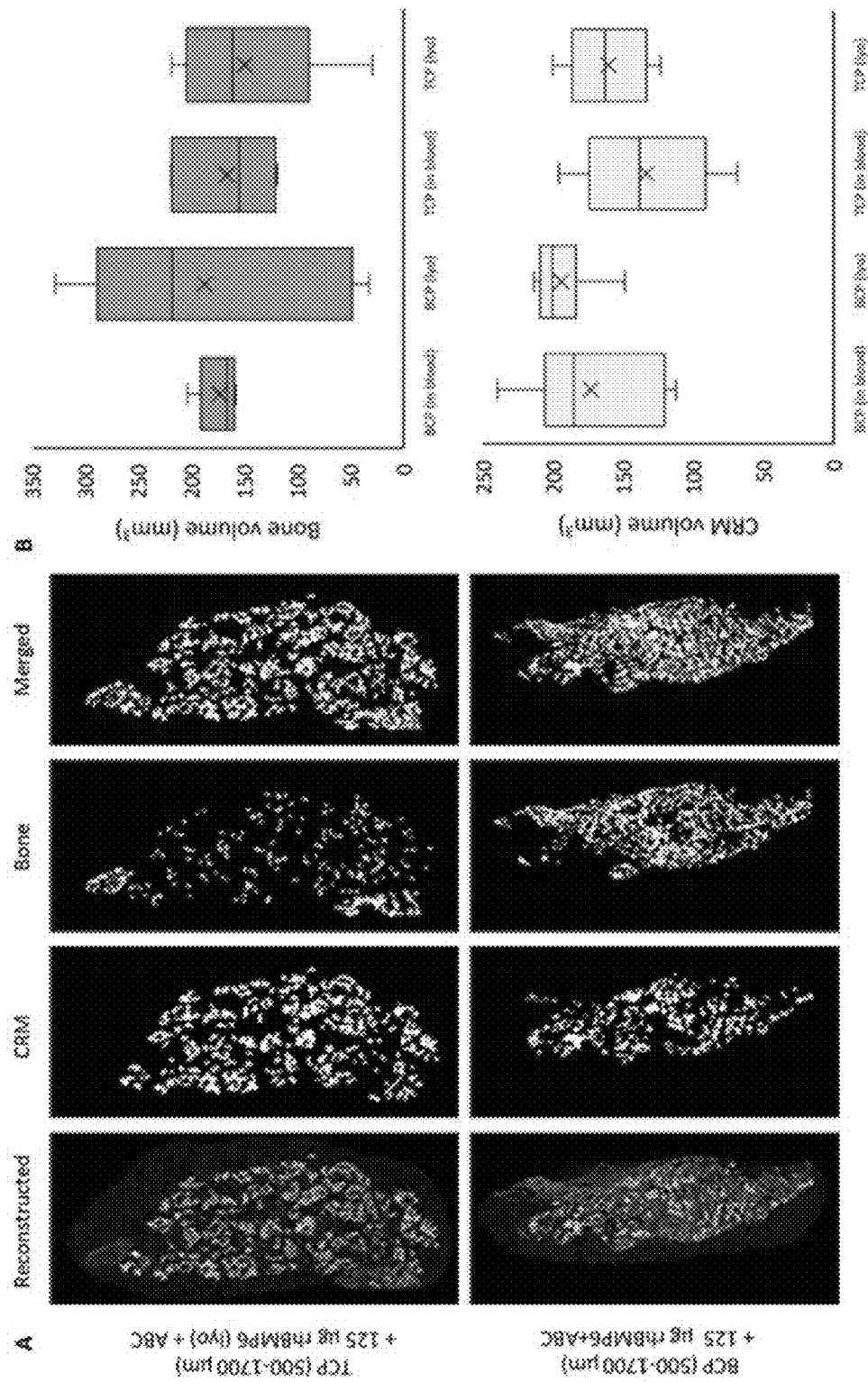
FIG. 4A shows separation of the newly formed bone and CRM on reconstructed µCT images.
FIG. 4B shows graph illustrating a bone volume and CRM volume (mm³) among experimental groups on day 50.

The success of spinal fusion was analyzed by μCT analyses of the anterior and posterior transverse processes in conjunction with the newly formed ectopic bone connecting them into a new columnar ectopic bone structure (FIG. 3A). The success rate of the spinal fusion observed by μCT analyses was in total 90.9% (39 successful, 3 failed and 2 partially fused) (FIG. 3B). The segmental mobility was tested by individual segment palpation. Spinal fusion/segment immobility was found in 90.9% cases confirming the successful fusion rate as determined by μCT analyses (FIG. 3C).

μCT Analyses of Newly Formed Bone

μCT analyses of PLF in rabbits is shown in FIG. 4, where FIG. 4A shows a separation of the newly formed bone and CRM on reconstructed μCT images, and FIG. 4B shows a bone volume and CRM volume (mm3) among experimental groups on day 50. Results are shown as median with interquartile range (IQR). Non-parametric Kruskal Wallis test was used with post hoc Mann Whitney U-test.

The new bone was quantitatively separated from the CRM (FIG. 4A) and then the bone volume (FIG. 4B), unresorbed CRM volume (FIG. 4B) and trabecular parameters (data not shown) were calculated. The new bone volume was robust in all treated animals. The highest average amount of bone formed in implants containing rhBMP6 lyophilized on the BCP, while less bone formed in implants containing rhBMP6 lyophilized on TCP bioceramics. However, the differences in the bone volume, CRM volume, and trabecular parameters (data not shown) among the experimental animals were not significant neither regarding the bioceramic type (BCP vs TCP) nor the rhBMP6 delivered directly in blood vs priorly lyophilized on the bioceramic particles for the duration of the experiment (FIG. 4).

Biomechanical Testing

Figure 5:
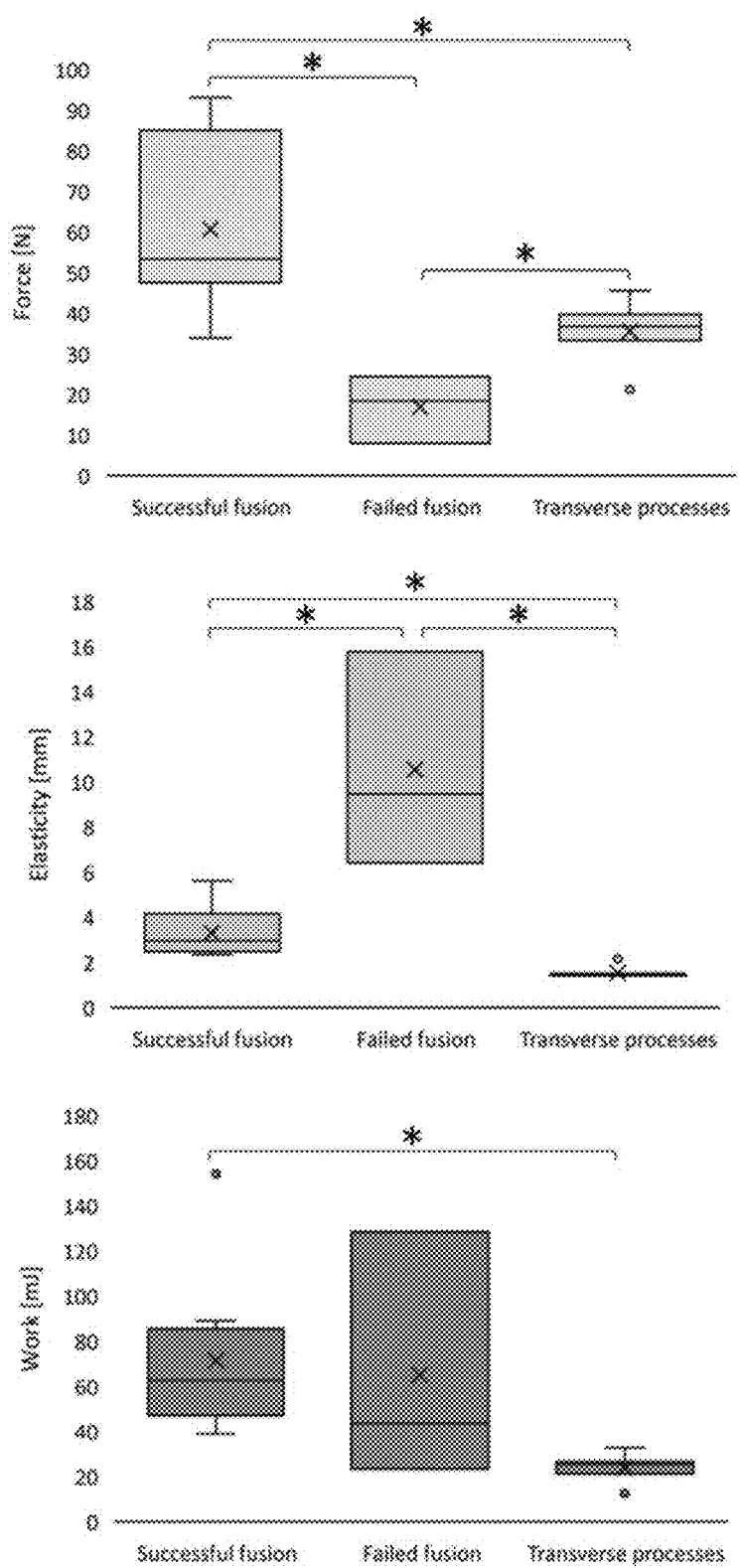
FIG. 5 shows graphs illustrating a three-point bending test of newly formed bone and adjacent transverse processes.

FIG. 5 shows a three-point bending test of newly formed bone and adjacent transverse processes. Test was performed using Texture Analyser TA.HD Plus (Texture Technologies, Hamilton, Mass., USA). Force (N), elasticity (mm) and work (mJ) measured on samples grouped based on the fusion success (successful/failed fusion) and isolated transverse processes. Results are shown as median with interquartile range (IQR). Non-parametric Kruskal Wallis H-test was used with post hoc Mann Whitney U-test. Asterisk indicates P<0.05.

Samples were grouped according to the success rate of the spinal fusion (successful/failed fusion) and obtained results are shown in FIG. 5. Force needed to break the new bone forming a successful fusion was significantly higher compared to adjacent transverse processes used as control samples and specimens with failed fusion. On the other hand, elasticity of the successfully fused implants and of transverse processes was significantly lower than in specimens with a failed fusion. Work needed to break the newly formed bone in successfully fused samples was significantly higher when compared to transverse processes (FIG. 5).

Histology

Figure 6A:
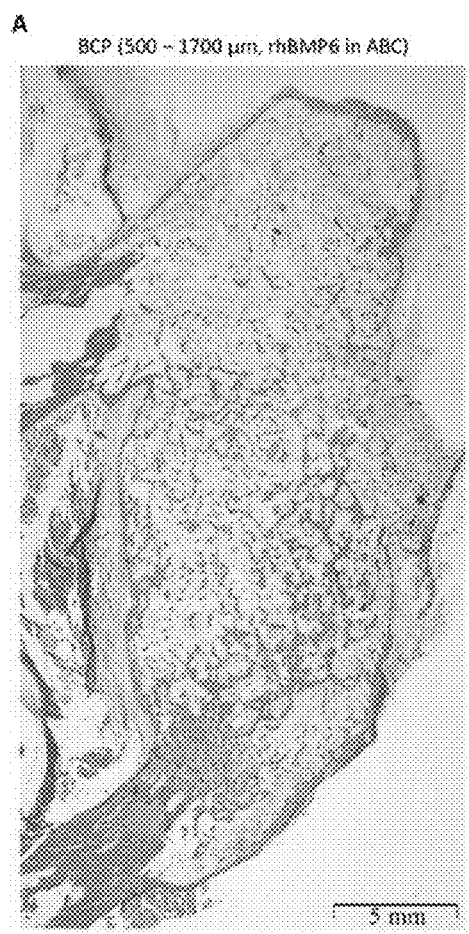
FIG. 6A shows histology sections of new ectopic bone and adjacent transverse processes.
Figure 6A:
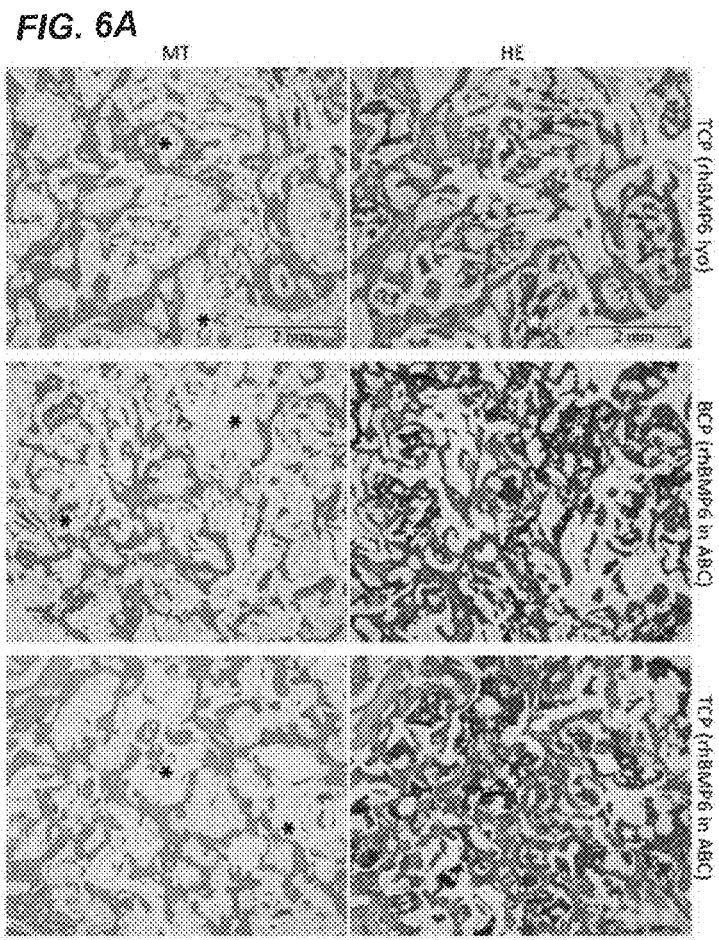
Figure 6B:
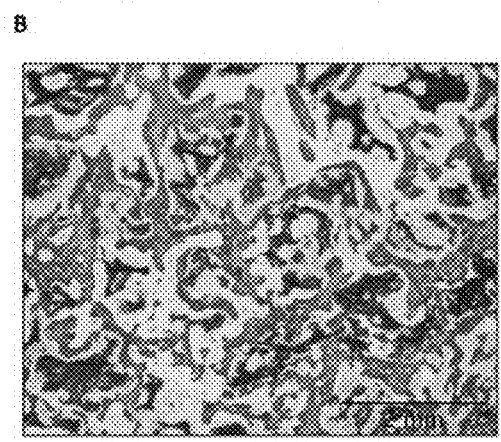
FIG. 6B shows a static histomorphometry analysis done on the histology sections stained by HE.
Figure 6C:
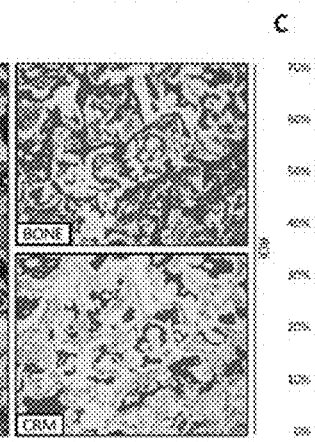
FIG. 6C shows a graph illustrating an area of interest (%)—bone, CRM and bone marrow among histology sections between two experimental groups containing TCP and BCP.
Figure 6C:
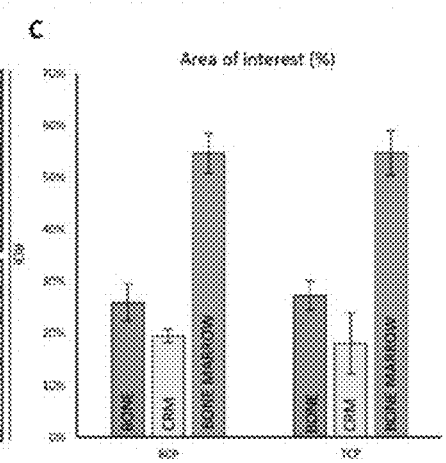

FIG. 6A shows histology sections of new ectopic bone and adjacent transverse processes. ABGS implants contained rhBMP6, ABC and CRM (TCP or BCP). Sections were stained either by Masson's trichrome (MT) or hematoxylin & eosin (HE). Black (MT) and white (HE) asterisks indicated bioceramic particles; yellow arrows indicated newly formed bone on HE stained sections; newly formed bone on MT sections was stained green. FIG. 6B shows a static histomorphometry analysis done on the histology sections stained by HE, where bone was light purple while CRM was dark purple. Regions of interest (bone, CRM) were masked with distinctive color (red) which were further thresholded and measured. FIG. 6C are graphs are showing area of interest (%)—bone, CRM and bone marrow among histology sections between two experimental groups containing TCP and BCP. Results are shown as mean±SD. Scale bars are showed in lower right corner indicating lower (5 mm) and higher magnification (2 mm).

Formation and osseointegration of newly formed bone were analyzed on frontal sections of undecalcified samples stained by trichrome Goldner and hematoxylin-eosin (FIG. 6A). Newly formed bone was present around and between the bioceramic particles. On histological sections there was no difference regarding the resorption rate between BCP and TCP particles. The fusion and complete osseointegration of newly formed bone with the adjacent transverse processes was presented in histological sections and in the μCT analyses. Importantly, bioceramic particles were integrated as well into the transverse processes supporting a uniform distribution of bone and biomechanical properties of the novel bone construction (FIG. 6).

Histomorphometry

The proportion of newly formed bone ectopic bone, CRM and bone marrow on histological sections in the central part of the fusion mass was measured. Samples were grouped according to the chemical composition of particles (TCP/BCP) regardless of the method of rhBMP6 application. Proportion of observed components was similar in both ABGS formulations; with the bone marrow as a predominant component in more than half of the analyzed area followed by the areas containing bone and CRM (FIG. 6B).

Conclusion

In Example 1 it is demonstrated that ABGS (rhBMP6/ABC/CRM) prepared with a synthetic ceramic (TCP or BCP) as a compression resistant matrix (CRM) is capable of inducing new bone formation and to promote spinal fusion in rabbit PLF model. The newly formed bone underwent a typical physiological bone remodeling establishing osseointegration with the trabeculae of native transverse processes containing functional bone marrow elements. The salient features of the present invention are that TCP or BCP may be used as a CRM substitute for devitalized allograft with ABGS. The surprising effect of the present invention is that a specific particle size of the ceramics is of critical importance to induce new bone uniformly within the ABGS implant and to promote the osseointegration. Both TCP and BCP yielded a complete fusion as there is no difference in the quality and quantity of bone formed. Moreover, according to the present invention, the ABGS may be prepared by adding rhBMP6 in the blood prior to coagulation, or lyophilizing it onto ceramics then adding blood to achieve the autologous blood coagulum.

Synthetic ceramics as the CRM in the ABGS provided better handling properties and avoided the disadvantages that allograft possesses, including the potential for transmission of infectious diseases and rejection due to its immunogenicity (4, 5). Moreover, ceramics underwent creeping substitution more orderly in time than allograft which was rapidly replaced in a short period of time resulting eventually in biomechanical disfunction (15). Synthetic ceramics composites could also be engineered if needed to offer a better biomechanical stability. TCP is a more biodegradable and soluble bioceramics, while HA provides a more stable phase, therefore TCP/HA in 80:20 or 60:40 ratio may be used in conjunction with BMP to promote a long-term sustainability and provide a compressive resistance as required for certain spine fusion indications. The effects of rhBMP6 at one dose (50 μg/mL of ABC) was examined and this dose was chosen based on previous dose ranging studies with the ABGS with or without allograft (15). The success rate in the tested dose in combination with ceramics and ABC were above 90%. In previous studies when rhBMP6 was used in the combination with ABC without CRM or with allograft as CRM, the optimal rhBMP6 dose was around 250 μg (100 μg/mL of ABC), while the dose of 125 μg (50 μg/mL of ABC) was only moderately successful (fusion in two out of four rabbits) (15). This suggested that the use of synthetic ceramics as the CRM shifted the rhBMP6 amount required to achieve the successful fusion to the lower range when compared to a previous study with the allograft as CRM (15).

It has been previously described that ABC serves as a physiological native BMP carrier (15, 22, 26) and provided binding for rhBMP6 with plasma proteins within the fibrin meshwork, allowing a sustained release of rhBMP6 and suppressed inflammation when implanted with CRM to improve the handling properties.

In addition to chemical properties, the physical attributes of ceramics like surface area, pore volume and particle size are known to play a significant role as carrier for BMP in bone induction (21, 28). It has been observed for the first time the geometry of bioceramics plays a critical role in achieving a complete fusion and promoting osseointegration between the transverse processes and new bone when implanted with the ABGS of the present invention. Calcium phosphate bioceramics are engineered into preformed granules or blocks (24) in order to provide osteoconductivity for bone in-growth on to its surface or down into pores, channels or pipes (29). Interconnected pores within the bioceramics allow vascularization, cell migration and nutrient diffusion required for sustained cell viability and tissue function (30). The most critical property for bioceramics in the preparation of the ABGS is the particle size and subsequently the surface area. RhBMP6 is bound tightly within fibrin mesh work and plasma proteins when added directly to ABC or upon release from the lyophilized rhBMP6-bioceramics composite. Examination of BCP ceramic in two different particle sizes (BCP 500-1700 μm and 1700-2500 μm) and TCP ceramic in two different slabs (high and low pore volume) as the CRM in the ABGS (rhBMP6/ABC/CRM) suggested that although bone formation was observed in all implants, successful fusion and osteointegration with adjacent transverse processes was observed only in implants containing properly selected ceramic particles. Namely, the volume of newly formed bone was higher and the osseointegration successful only in implants containing the ceramics of 500-1700 μm particle size.

Example 2

Example 2 describes three different performed experiments: in the first it has been varied both the chemical composition of particles and the particle size; in the second experiment it has been varied the method of rhBMP6 application and the particle size, while in the third experiment has been varied CRM/ABC ratio by increasing the bioceramic amount keeping the blood volume unchanged.

Material and Methods in Rat Subcutaneous Implant Assay

Rat subcutaneous implant assay was chosen as a method to evaluate osteconductivity and osteoinductivity of various ABGS compositions containing rhBMP6, ABC and bioceramic particles. The bioceramic particle features tested are shown in Table 3.

TABLE 3

| Lot Number | Material | Particle Size (mm) | Average Pore Diameter (microns) | Total Porous Volume (%) |
|---|---|---|---|---|
| SAMTCP030618A2 | β-TCP Granulate | 0.5-1.7 mm | 320 | 82 |
| SAMTCP030618A5 | β-TCP Granulate | 1-4 mm | 444 | 86 |
| SAMBP030718A2 | Biphasic Granulate | 0.5-1.7 mm | 356 | 86 |
| SAMBP030718A5 | Biphasic Granulate | 1-4 mm | 544 | 89 |
| SAMHA031218A2 | HA Granulate | 0.5-1.7 mm | | 76 |
| SAMHA031218A5 | HA Granulate | 1-4 mm | | 77 |

Three different experiments were performed: in the first both the chemical composition of particles and the particle size were varied; in the second experiment the method of rhBMP6 application and the particle size were varied; while in the third the CRM/ABC ratio was varied by increasing the bioceramic amount, but keeping the blood volume unchanged. All experiments were terminated at day 21. Number of implants in the first and third experiment was 10 per group while in the second experiment it was 6 per group. Experimental design is presented in Table 4.

Table 4 shows the experimental design of Example 2. In the first experiment bioceramics chemical composition and size of the particles was varied, in the second experiment method of rhBMP6 application and size of the particles was varied, and in the third experiment CRM/ABC ratio was varied.

TABLE 4

| Experiment | | |
|---|---|---|
| Chemical composition and particle size | Method of rhBMP6 application and particle size | Bioceramic mass/Autologous blood coagulum volume ratio |
| TCP 74-420 + ABC + BMP6 | BCP 74-420 μm + ABC + rhBMP6 | 25 mg BCP 1000-4000 μm + ABC + BMP6 |
| HA 74-420 + ABC + BMP6 | BCP 74-420 μm + ABC + rhBMP6 (lyophilized on BCP) | 50 mg BCP 1000-4000 μm + ABC + BMP6 |
| BCP 74-420 + ABC + BMP6 | BCP 1000-1700 μm + ABC + rhBMP6 | 75 mg BCP 1000-4000 μm + ABC + BMP6 |
| TCP 500-1500 + ABC + BMP6 | BCP 1000-1700 μm + ABC + rhBMP6 (lyophilized on BCP) + ABC | 100 mg BCP 1000-4000 μm + ABC + BMP6 |
| HA 500-1500 + ABC + BMP6 | BCP 1000-4000 μm + ABC + rhBMP6 | 125 mg BCP 1000-4000 μm + ABC + BMP6 |
| BCP 500-1500 + ABC + BMP6 | BCP 1000-4000 μm + ABC + rhBMP6 (lyophilized on BCP) | |
| TCP 1000-4000 + ABC + BMP6 | | |
| HA 1000-4000 + ABC + BMP6 | | |
| BCP 1000-4000 + ABC + BMP6 | | |

Test Items

Figure 7A:
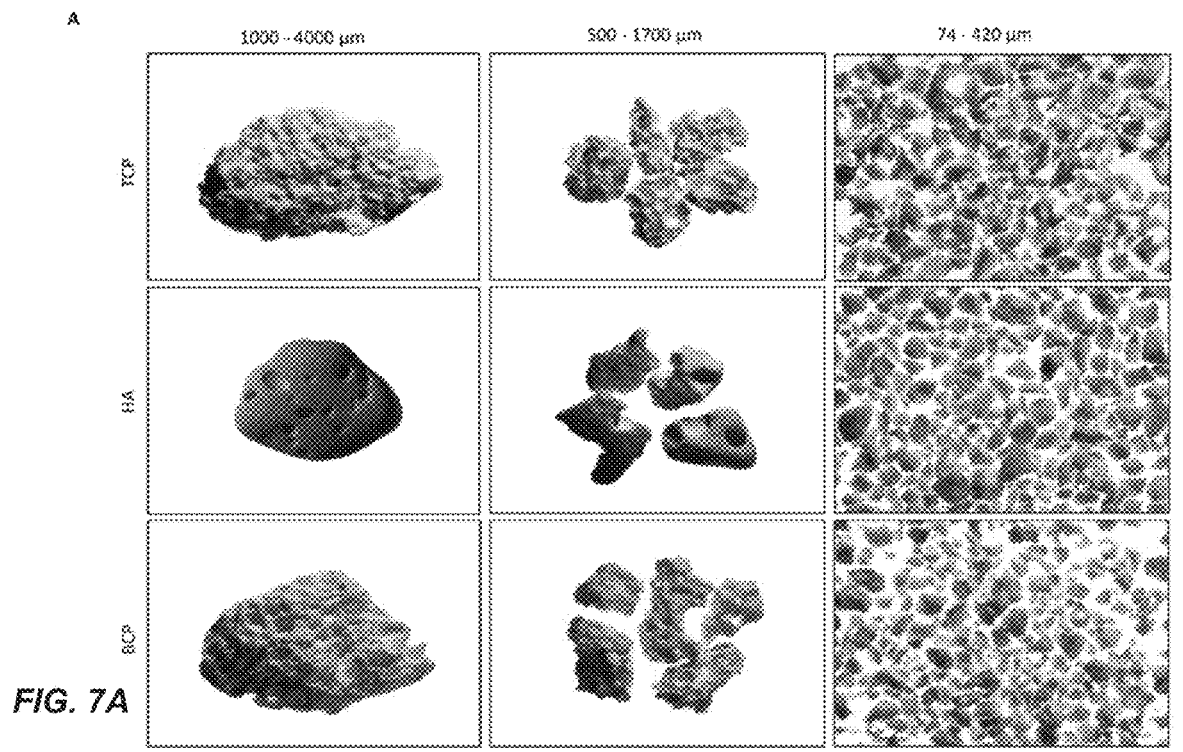
FIG. 7A shows various bioceramic particles which differ in chemical composition (tricalcium phosphate (TCP), hydroxyapatite (HA), and biphasic bioceramics (BCP)) and a particle size (74-420 µm, 500-1700 µm and 1000-4000 µm).
Figure 7B:
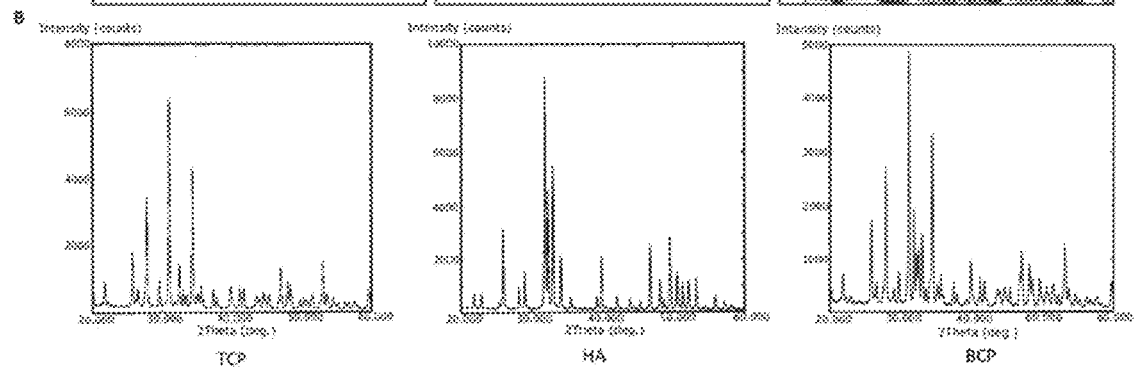
FIG. 7B shows an X-ray diffractogram pattern of TCP, HA and BCP in a particle size from 500-1700 µm.

FIG. 7A shows various bioceramic particles which differ in chemical composition (tricalcium phosphate (TCP), hydroxyapatite (HA), and biphasic bioceramics (BCP)) and particle size (74-420 μm, 500-1700 μm and 1000-4000 μm). FIG. 7B shows an X-ray diffractogram pattern of TCP, HA and BCP in particle size from 500-1700 μm. rhBMP6 produced by Genera Research (Zagreb, Croatia) and bioceramic particles produced by CaP BioMaterials (East Troy, Wis., USA) were used. The chemical composition of bioceramic particles was β-tricalcium phosphate (TCP), hydroxyapatite (HA), and biphasic bioceramics (BCP) containing 80% TCP and 20% HA with particle size of 74-420 μm (small particles), 500-1700 μm (medium particles) and 1000-4000 μm (large particles) (FIG. 7A-B). The dose of rhBMP6 was 20 μg/per implant in all experiments.

Autologous Bone Graft Substitute Composition Preparation

Steps of the ABGS preparation are marked with numbers: 1—blood is withdrawn in volume 500 μL per implant and it is transferred to the tube with aliquoted solution of rhBMP6 and gently mixed 2—blood with rhBMP6 is drawn into the syringe containing CRM; 3—final product (ABGS containing CRM) left on room temperature to coagulate; 4—subcutaneous implantation in axillary region of rat.

Figure 7C:
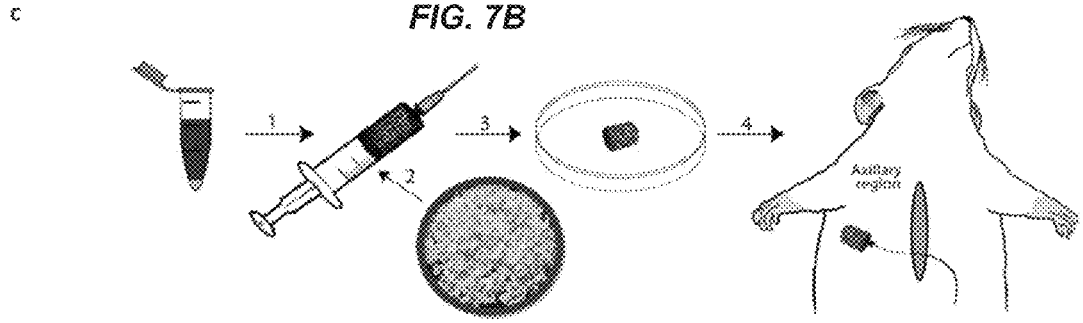
FIG. 7C schematically illustrates a preparation steps of an Autologous Bone Graft Substitute Composition implant and subcutaneous implantation in axillary region of rat.

In the first and third experiment 20 μg of rhBMP6 was added to 500 μL blood, mixed with bioceramic particles as specified in Table 4 and left to coagulate (FIG. 7C). In the second experiment implants were prepared either as described above, or rhBMP6 (20 μg) was lyophilized on the bioceramic particles, mixed with blood and left to coagulate. In the first and second experiment each implant contained 0.1 g of bioceramic particles, while in the third experiment the amount varied between the experimental groups (Table 4).

Experimental Animals

Male and female laboratory rats (Sprague Dawley strain, body weight between 200-300 g, 8 weeks old, in house bred-animal facility, Laboratory for mineralized tissue—School of Medicine, Zagreb Croatia) were used in all in vivo experiments. Rats were housed in PS (poly sulfonic) cages in conventional laboratory conditions at the temperature of 20-24° C., relative humidity of 40 70% and noise level 60 DCB. Fluorescent lighting provided illumination 12 hours per day. Standard GLP diet and fresh water was provided ad libitum, with environmental enrichment. Animal care complied with SOPs of the Animal facility; the European convention for the protection of vertebrate animals used for experimental and other scientific purposes (ETS 123). Ethical principles of the study ensured compliance with European Directive 010/63/E, the Law on Amendments to Animal Protection Act (Official Gazette 37/13, the Animal Protection Act (official Gazette 102/17), Ordinance on the protection of animals used for scientific purposes (Official Gazette 55/13), FELASA recommendations and recommendations of the Ethics Committee School of Medicine, University of Zagreb.

Rat Subcutaneous Implant Assay

Prior to surgery rats were anesthetized by a combination of dexmedetomidine at 0.5 mg/kg and ketamine 75 mg/kg and butorphanol 1 mg/kg. A vertical incision (1 cm) was made under sterile conditions in the skin over the thoracic region, and the pockets were prepared by a blunt dissection on both sides of the incision (FIG. 7C). The implant was inserted deep into the pockets, and the incision was closed with a surgical clip. The day of implantation was designated as day 0 of the experiment. In the postoperative period during the first 72 hours, analgesia was monitored using a pain scale. If the animal was in pain, an additional dose of buprenorphine was administered intramuscularly. Implants were removed on day 21 after implantation for analysis and surrounding tissue was examined for the possible presence of inflammation and oedema.

µCT Scan and Analysis

To follow and visualize new ectopic bone formation, 1076 SkyScan µCT machine was used. Implants were scanned after explantation. Scanning resolution was set at 18 µm spatial resolution with 0.5 mm aluminium filter and frame averaging set to a value of 2. The scanning width was set to 34 mm. Acquired images were reconstructed using NRecon software (SkyScan, Belgium). Further assessment and analysis of ectopic bone was done using CTAn software (SkyScan, Belgium) as previously described (22).

Histology

Following implant explantation, samples were fixed in 4% formalin for 10 days. After fixation, all samples were decalcified using 14% EDTA in 4% formalin solution for 20 days (solution was changed every 2 days). All samples were embedded in paraffin and cut at 5-µm thickness. Samples were stained by Goldner's trichrome stain. Histological examination was used to assess the extent and structure of osteogenesis in the implant.

Histomorphometry

Quantitative analysis of bone architecture was conducted by histomorphometry to reveal the amount and the structure of newly formed tissues including bone, distribution of CRM, bone-ceramic structure and the bone marrow distribution among the ectopic explant on day 21. Histology sections were stained by Goldner's trichrome stain, staining the bone green/turquoise, while CRM remained white. Images were taken using an Olympus microscopy system-Olympus SZX10 Stereo Microscope and Olympus BX53 Upright Microscope equipped with a DP27 camera (5 megapixels, 15 fps) and operated by cellSens Dimension software (Olympus, Japan). Goldner's trichrome stained sections were imaged at 1.25× (0.24 pixel/µm) and 10× (1.83 pixel/µm) magnification. The bone area was selected automatically due to its distinct color(green/turquoise), while whole area of histological section and the area of CRM particles were selected manually and masked with the distinctive color (black) in Photoshop software (Adobe Systems, San Jose, Calif.) in order to be recognized by measuring software. Masked areas (bone, CRM, whole area) were converted to RGB stacks which were further thresholded and measured in Fiji ImageJ software (version 1.51r; NIH, Maryland, USA). Bone marrow area was calculated as remaining pixels—bone area and CRM area were subtracted from the whole area. Results are expressed as area percentages.

With additional segmentation of the bone area, the amount of cortical bone was measured among experimental groups.

Distance measurements between bioceramic particles were determined with cellSens Dimension software (Olympus, Japan) using Count & Measure tools. Three histology sections were measured per group and each section was measured six times. A general rule was to measure the longest distances between particles.

Data Analysis

Data distribution had been checked with Kolmogorov-Smirnov test and according to the results and the sample size appropriate non-parametric tests and data description have been used. Differences between groups regarding bone volume, trabecular thickness and trabecular number were analyzed with Kruskall-Wallis test (all groups together) followed with post-hoc Mann-Whitney U test (comparison between each two groups). All data have been shown in Box and Whisker's plots. The P values below 0.05 was considered significant. Statistical software IBM SPSS Statistics, version 25.0 has been used in all statistical procedures.

Results

Bone Quantity

ABGS containing rhBMP6 in ABC combined with bioceramic particles, implanted subcutaneously in the axillary region of rats induced formation of new bone which along with bioceramic particles formed unique, vascularized, complex tissue engineered bone-ceramic structure (BCS). The amount of new bone was extensive in all BCS regardless of the particle size, chemical composition of particles, method of rhBMP6 application and CRM/ABC ratio used in tested ABGS formulations (FIGS. 8-10).

Figure 8:
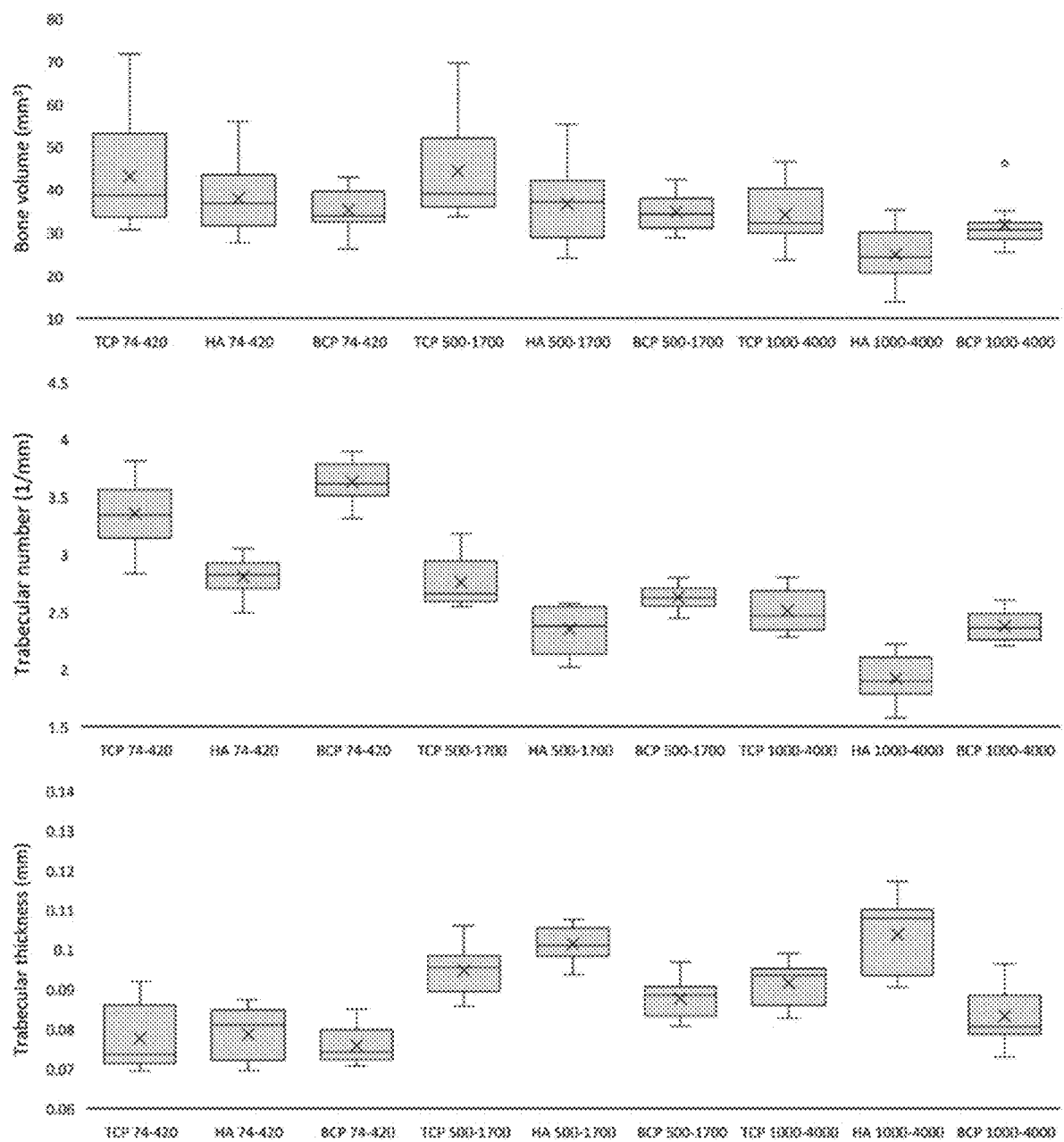
FIG. 8 shows a µCT analyses of bone/bioceramic construct containing various size particles.

FIG. 8 shows µCT analyses of bone/bioceramic construct containing various size particles. Bone volume (mm3) trabecular number (1/mm) and trabecular thickness (mm) among experimental groups on day 21. Results are shown as median with interquartile range (IQR). Non-parametric Kruskal Wallis test was used (P<0.05) with post hoc Mann Whitney U-test. Detailed statistical analysis is presented in Table 5.

Figure 9A:
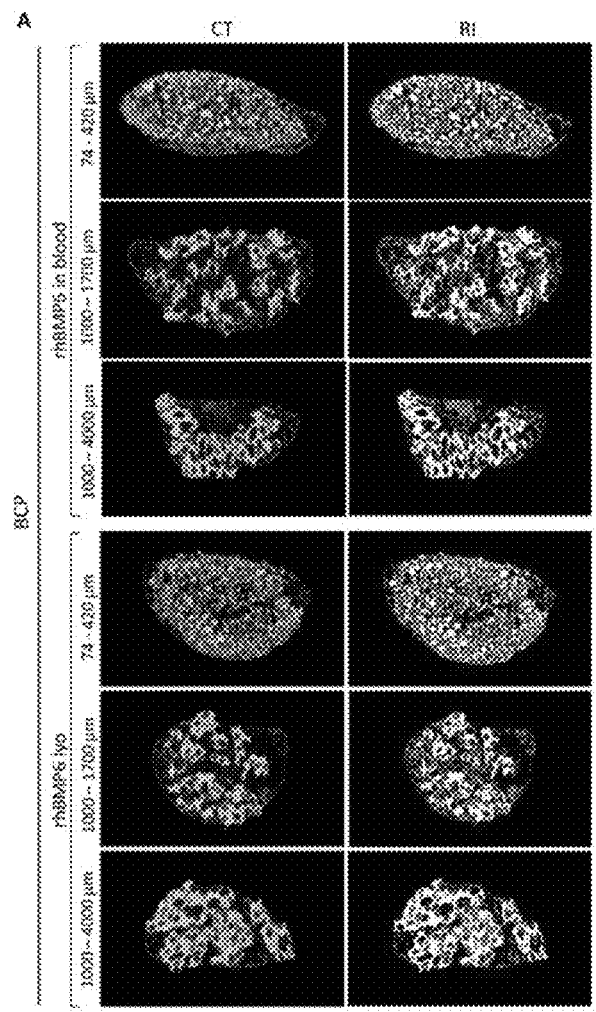
FIG. 9A shows a µCT sections and reconstructed images (RI) of BCS showing newly formed bone.
Figure 9B:
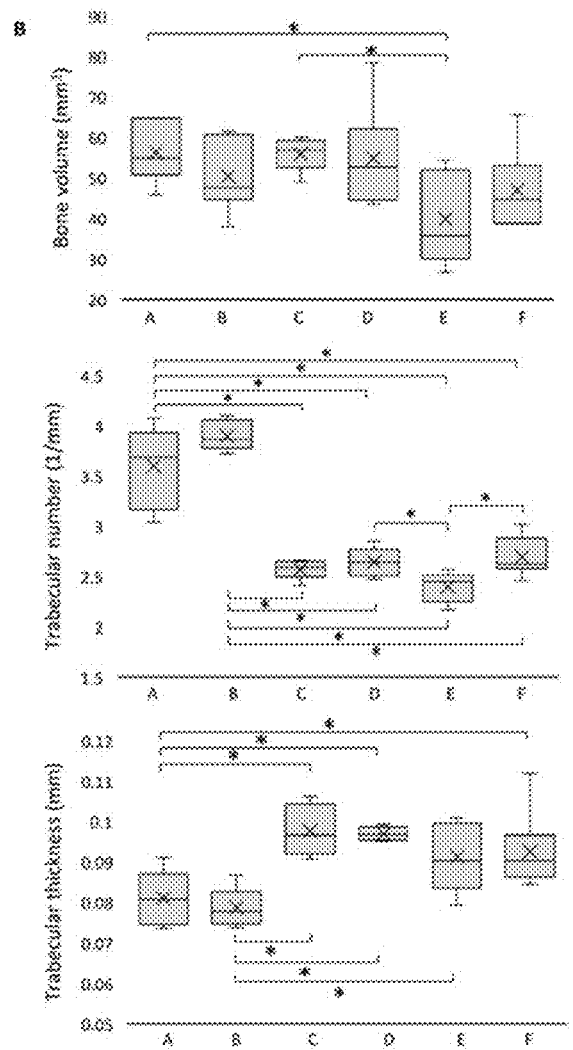
FIG. 9B shows graphs illustrating a bone volume (mm³), trabecular number (1/mm) and trabecular thickness (mm) among experimental groups: A (74-420 µm, in blood); B (74-420 µm, lyophilized); C (500-1700 µm, in blood); D (500-1700 µm, lyophilized); E (1000-4000 µm, in blood); F (500-1700 µm, lyophilized) on day 21 shown as median with interquartile range (IQR).

FIG. 9A shows a µCT sections and reconstructed images (RI) of BCS showing newly formed bone (green) and CRM (white). µCT sections and RI are showing various particle size (74-420 µm, 500-1700 µm, 1000-4000 µm) of BCP with different methods of rhBMP6 application—directly into the blood or pre-lyophilized. FIG. 9B are graphs illustrating a bone volume (mm3), trabecular number (1/mm) and trabecular thickness (mm) among experimental groups: A (74-420 µm, in blood); B (74-420 µm, lyophilized); C (500-1700 µm, in blood); D (500-1700 µm, lyophilized); E (1000-4000 µm, in blood); and F (500-1700 µm, lyophilized) on day 21 shown as median with interquartile range (IQR). Non-parametric Kruskal Wallis test was used with post hoc Mann Whitney U-test.

Figures 10A, 10B:
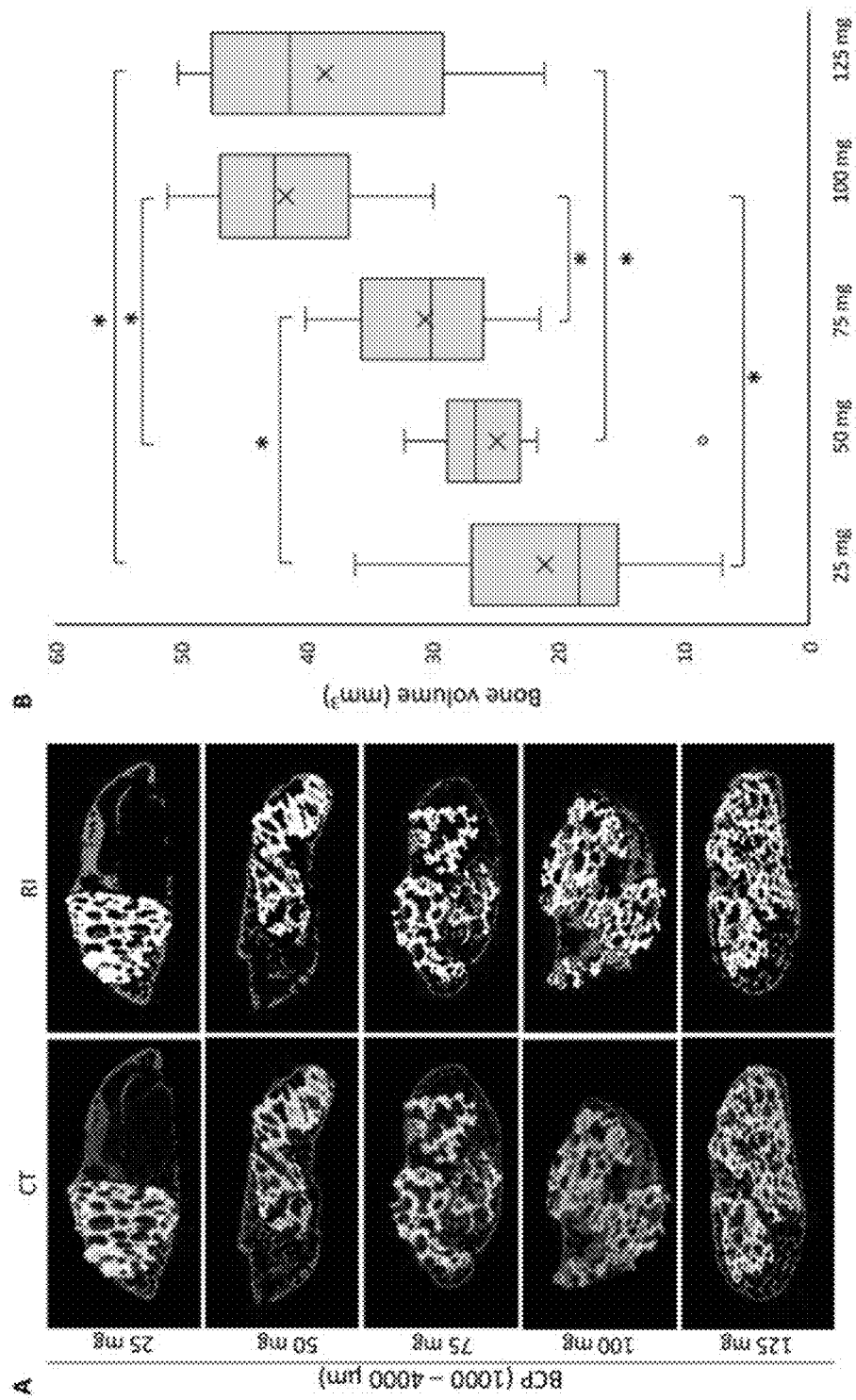
FIG. 10A shows a µCT sections and reconstructed images (RI) of BCS showing newly formed bone.
FIG. 10B shows graphs illustrating a bone volume (mm³), trabecular number (1/mm) and trabecular thickness (mm) among experimental groups (from 25 to 125 mg BCP per implant) on day 21 shown as median with interquartile range (IQR).

FIG. 10A shows µCT sections and reconstructed images (RI) of bone/bioceramic construct showing newly formed bone (green) and CRM (white). µCT sections and RI are showing increasing mass of the same bioceramic particles (BCP, 1000-4000 µm) in same blood volume. FIG. 10B is graph illustrating a bone volume (mm3) among experimental groups (from 25 to 125 mg BCP per implant) on day 21 shown as median with interquartile range (IQR). Nonparametric Kruskal Wallis test was used with post hoc Mann Whitney U-test.

Analyses revealed that both TCP and HA (used individually or in combination as BCP) possessed appropriate osteoconductive properties (FIG. 8). Although there were some significant differences among experimental groups regarding bone volume and trabecular parameters (FIG. 8; Table 4), the current ABGS formulations were comparable regarding their osteoconductive properties.

Table 5 shows statistical significance of the differences between the groups in the first experiment. Differences between groups regarding bone volume, trabecular thickness and trabecular number were analyzed with Kruskall-Wallis test (all groups together) followed with post-hoc Mann-Whitney U test (comparison between each two groups). P values are shown for all comparisons between the experimental group. Statistically significant values (p<0.05) as well as group with higher values in each comparison are in bold.

TABLE 5

| Parameter | Comparison - Chemical Composition | P Value | Comparison - Particle Size | P Value |
|---|---|---|---|---|
| Bone Volume (mm³) | TCP 74-420 vs. HA 74-420 | 0.496 | TCP 74-420 vs. TCP 500-1700 | 0.597 |
| | CP 74-420 vs. BCP 74-420 | 0.199 | TCP 74-420 vs TCP 1000-4000 | 0.142 |
| | HA 74-420 vs. BCP 74-420 | 0.496 | TCP 500-1700 vs. TCP1000-4000 | 0.027* |
| | TCP 500-1700 vs. HA 500-1700 | 0.174 | HA 74-420 vs. HA 500-1700 | 0.762 |
| | TCP 500-1700 vs. BCP 500-1700 | 0.028* | HA 74-420 vs. HA 1000-4000 | 0.003* |
| | HA 500-1700 vs. BCP 500-1700 | 0.821 | HA 500-1700 vs. HA 1000-4000 | 0.014* |
| | TCP 1000-4000 vs. HA 1000-4000 | 0.015* | BCP 74-420 vs. BCP 500-1700 | 0.762 |
| | TCP 1000-4000 vs. BCP 1000-4000 | 0.288 | BCP 74-420 vs. BCP 1000-4000 | 0.041* |
| | HA 1000-4000 vs. BCP 1000-4000 | 0.014* | BCP 500-1700 vs. BCP 1000-4000 | 0.070 |
| Trabecular Thickness (mm) | TCP 74-420 vs. HA 74-420 | 0.705 | TCP 74-420 vs. TCP 500-1700 | 0.001* |
| | TCP 74-420 vs. BCP 74-420 | 0.940 | TCP 74-420 vs. TCP 1000-4000 | 0.002* |
| | HA 74-420 vs. BCP 74-420 | 0.450 | TCP 500-1700 vs. TCP 1000-4000 | 0.253 |
| | TCP 500-1700 vs. HA 500-1700 | 0.023* | HA 74-420 vs. HA 500-1700 | 0.000* |
| | TCP 500-1700 vs. BCP 500-1700 | 0.028* | HA 74-420 vs. HA 1000-4000 | 0.000* |
| | HA 500-1700 vs. BCP 500-1700 | 0.000* | HA 500-1700 vs. HA 1000-4000 | 0.327 |
| | TCP 1000-4000 vs. HA 1000-4000 | 0.015* | BCP 74-420 vs. BCP 500-1700 | 0.001* |
| | TCP 1000-4000 vs. BCP 1000-4000 | 0.034* | BCP 74-420 vs. BCP 1000-4000 | 0.016* |
| | *HA 1000-4000* vs. BCP 1000-4000 | 0.001* | BCP 500-1700 vs. BCP 1000-4000 | 0.082 |
| Trabecular Number (1/mm) | TCP 74-420 vs. HA 74-420 | 0.001* | TCP 74-420 vs. TCP 500-1700 | 0.001* |
| | TCP 74-420 vs. BCP 74-420 | 0.023* | TCP 74-420 vs. TCP 1000-4000 | 0.000* |
| | HA 74-420 vs. BCP 74-420 | 0.000* | TCP 500-1700 vs. TCP 1000-4000 | 0.050 |
| | TCP 500-1700 vs. HA 500-1700 | 0* | HA 74-420 vs. HA 500-1700 | 0.000* |
| | TCP 500-1700 vs. BCP 500-1700 | 0.326 | HA 74-420 vs. HA 1000-4000 | 0.000* |
| | HA 500-1700 vs. BCP 500-1700 | 0.001* | HA 500-1700 vs. HA 1000-4000 | 0.001* |
| | TCP 1000-4000 vs. HA 1000-4000 | 0.000* | BCP 74-420 vs. BCP 500-1700 | 0.000* |
| | TCP 1000-4000 vs. BCP 1000-4000 | 0.142 | BCP 74-420 vs. BCP 1000-4000 | 0.000* |
| | HA 1000-4000 vs. BCP 1000-4000 | 0.000* | BCP 500-1700 vs. BCP 1000-4000 | 0.002* |

Although histological and histomorphometrical analyses revealed that small, medium and large particles significantly influenced with the ABC carrier and rhBMP signal the structural pattern of newly formed ectopic organs (discussed in following sections), μCT analyses revealed that they did not necessarily differ in the amount of new bone on day 21 (FIGS. 8 and 9; Table 5 and 4). However, ABGS containing smaller ceramic particles had a more favorable structural properties as compared to implants with larger particles sizes (FIGS. 8 and 9; Table 5 and 6).

Table 6 shows statistical significance of the differences between the groups in the second experiment. Differences between groups regarding bone volume, trabecular thickness and trabecular number were analyzed with Kruskall-Wallis test (all groups together) followed with post-hoc Mann-Whitney U test (comparison between each two groups). P values are shown for all comparisons between the experimental group. Statistically significant values (p<0.05) as well as group with higher values in each comparison are in bold.

TABLE 6

| Parameter | Comparison - Method of rhBMP6 application | P Value (Mann-Whitney U test) |
|---|---|---|
| Bone Volume (mm3) | 74-420 (in blood) vs. 74-420 (lyo) | 0.262 |
| | 1000-1700 (in blood) vs. 1000-1700 (lyo) | 0.262 |
| | 1000-4000 (in blood) vs. 1000-4000 (lyo) | 0.361 |
| Trabecular thickness (mm) | 74-420 (in blood) vs. 74-420 (lyo) | 0.631 |
| | 1000-1700 (in blood) vs. 1000-1700 (lyo) | 1.000 |
| | 1000-4000 (in blood) vs. 1000-4000 (lyo) | 1.000 |
| Trabecular number (1/mm) | 74-420 (in blood) vs. 74-420 (lyo) | 0.109 |
| | 1000-1700 (in blood) vs. 1000-1700 (lyo) | 0.423 |
| | 1000-4000 (in blood) vs. 1000-4000 (lyo) | 0.018* |
| Bone Volume (mm3) | 74-420 (in blood) vs. 500-1700 (in blood) | 0.873 |
| | 74-420 (in blood) vs. 1000-4000 (in blood) | 0.045* |
| | 74-420 (lyo) vs. 500-1700 (lyo) | 0.749 |
| | 74-420 (lyo) vs. 1000-4000 (lyo) | 0.749 |
| | 1000-1700 (in blood) vs. 1000-4000 (in blood) | 0.028* |
| | 1000-1700 (lyo) vs. 1000-4000 (lyo) | 0.150 |

TABLE 6-continued

| Parameter | Comparison - Method of rhBMP6 application | P Value (Mann-Whitney U test) |
|---|---|---|
| Trabecular thickness (mm) | 74-420 (in blood) vs. 500-1700 (in blood) | 0.006* |
| | 74-420 (in blood) vs. 1000-4000 (in blood) | 0.100 |
| | 74-420 (lyo) vs. 500-1700 (lyo) | 0.004* |
| | 74-420 (lyo) vs. 1000-4000 (lyo) | 0.006* |
| | 1000-1700 (in blood) vs. 1000-4000 (in blood) | 0.144 |
| | 1000-1700 (lyo) vs. 1000-4000 (lyo) | 0.055 |
| Trabecular number (1/mm) | 74-420 (in blood) vs. 500-1700 (in blood) | 0.004* |
| | 74-420 (in blood) vs. 1000-4000 (in blood) | 0.006* |
| | 74-420 (lyo) vs. 500-1700 (lyo) | 0.004* |
| | 74-420 (lyo) vs. 1000-4000 (lyo) | 0.004* |
| | 1000-1700 (in blood) vs. 1000-4000 (in blood) | 0.068 |
| | 1000-1700 (lyo) vs. 1000-4000 (lyo) | 0.749 |

When the same particle size was used, rhBMP6 added in blood or priorly lyophilized on the bioceramics and mixed with blood, did not really influence the new ectopic formed organ parameters on day 21 (FIG. 9; Table 6).

Importantly, ABGS compositions containing higher CRM/ABC ratios induced more bone than compositions containing lower CRM/ABC ratios. The most optimal ratio seemed to be in a range from 0.1 to 0.125 g CRM per 500 µL of ABC. (FIG. 10; Table 7).

Table 7 shows statistical significance of the differences between the groups in the third experiment. Differences between groups regarding bone volume, trabecular thickness and trabecular number were analyzed with Kruskall-Wallis test (all groups together) followed with post-hoc Mann-Whitney U test (comparison between each two groups). P values are shown for all comparisons between the experimental group. Statistically significant values (p<0.05) as well as group with higher values in each comparison are in bold.

TABLE 7

| Comparison | Bone Volume |
| --- | --- |
| 25 mg vs. 50 mg | 0.233 |
| 25 mg vs. 75 mg | 0.018 |
| 25 mg vs. 100 mg | <0.001 |
| 25 mg vs. 125 mg | 0.004 |
| 50 mg vs. 75. mg | 0.072 |
| 50 mg vs. 100 mg | <0.001 |
| 50 mg vs. 125 mg | 0.031 |
| 75 mg vs. 100 mg | 0.003 |
| 75 mg vs. 125 mg | 0.060 |
| 100 mg vs. 125 mg | 0.624 |

Bone-Ceramic Structure

BCS analysis on µCT and histology sections revealed that there are three structural patterns of the newly formed BCS determined by the geometry and particle size of bioceramic particles used as CRM. The main geometrical determinants of bioceramic particles include the particle size, the surface area of particles, the distance between particles and the presence of pores which increased the surface area and allowed bone ingrowth. Particle size and geometry played the main role in determining the pattern of the newly formed organ and in the particular the bone-ceramic structure in relationships with the accompanying soft tissues. There was no significant difference in new BCS and accompanying tissue neither between BCS of different chemical composition nor methods of rhBMP6 application within the similar CRM size range.

Figure 11:
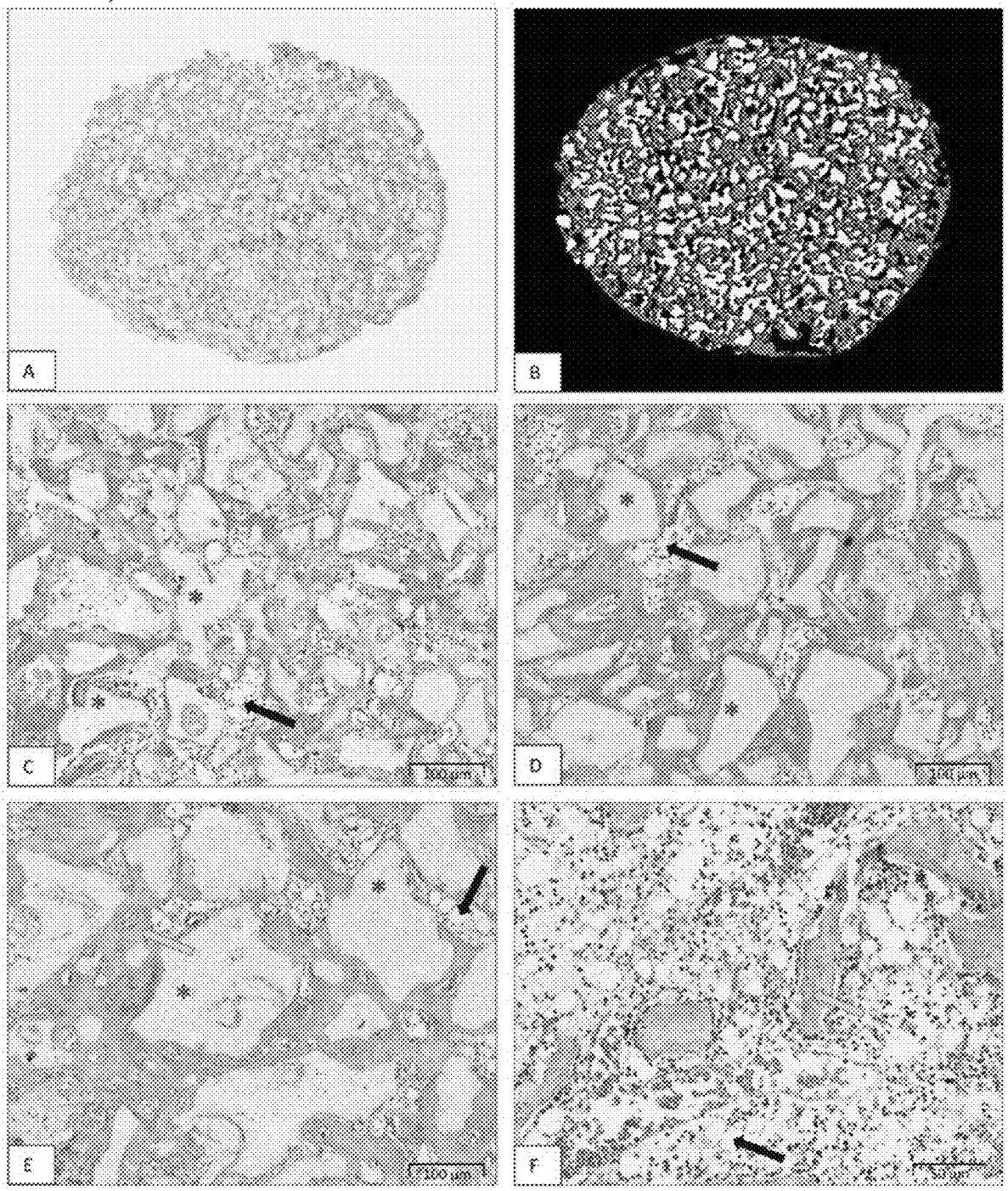
FIG. 11 shows bioceramic particles in a size range from 74 to 420 µm (small); (A)—Whole histology section of BCS with small particles; (B)—Reconstructed image showing newly formed bone (green) and CRM (white); and (C, D, E, F)—Goldner trichrome stained histology sections.

Small Particles (74-420 µm) BCS Consisted of a Dense Bone Network with a Higher Bone/Bone Marrow Ratio FIG. 11 relate to bioceramic particles in size range from 74 to 420 µm (small): (A)—Whole histology section of BCS with small particles, (B)—Reconstructed image showing newly formed bone (green) and CRM (white), (C, D, E, F)—Goldner trichrome stained histology sections. Red asterisk indicates bioceramic particles. Yellow arrow indicates newly formed bone, while black arrow shows bone marrow.

Figure 14A:
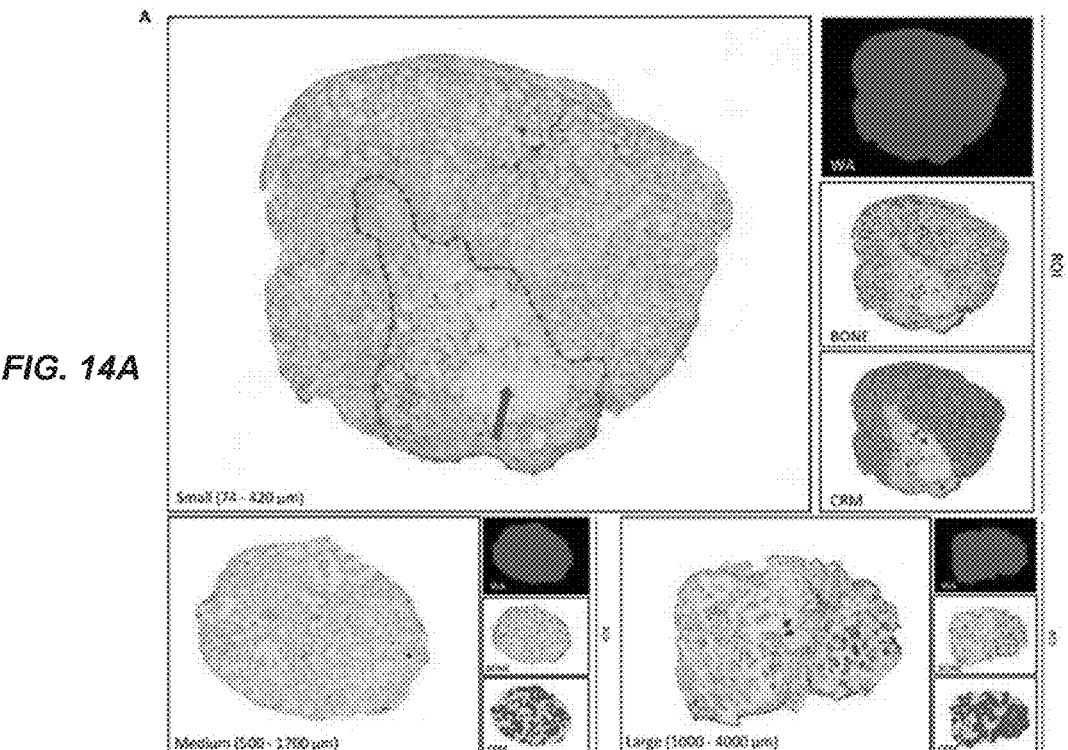
FIG. 14A is a group of histology sections of whole BCS containing different particle size stained by Mason's trichrome stain.
Figure 14B:
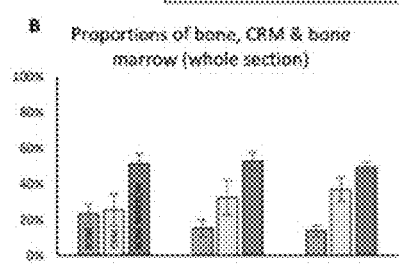
FIG. 14B is a chart showing the percentage (%) amount of newly formed bone in the whole histology sections (among different experimental groups.
Figure 14D:
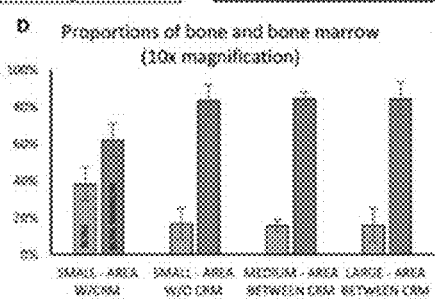
FIG. 14D is a chart showing the percentage (%) amount of newly formed bone among experimental groups containing small bioceramic particles (area with CRM, area without CRM), medium and large (area between particles).
Figure 14F:
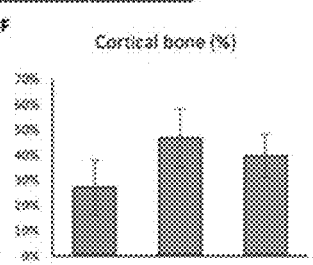
FIG. 14F is a chart showing the amount of cortical bone among experimental groups containing small, medium and large bioceramic particles.
Figure 14C:
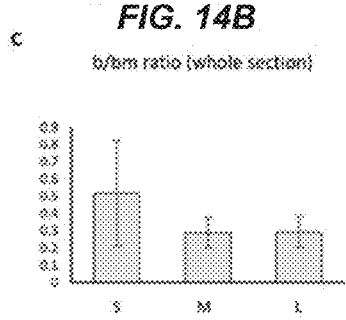
FIG. 14C is a chart showing a bone/bone marrow ratio of whole histology sections among different experimental groups.
Figure 14E:
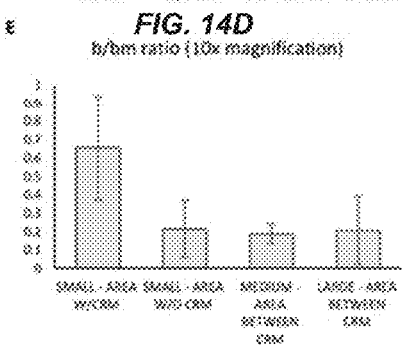
FIG. 14E is a chart showing a Bone/bone marrow ratio among experimental groups containing small bioceramic particles (area with CRM, area without CRM), medium and large (area between particles).

FIG. 14 shows a static histomorphometry analysis: FIG. 14A is a Histology section of whole BCS containing different particle size stained by Mason's trichrome stain. BCS containing small bioceramic particles (74-420 µm) usually consists of area with (yellow arrow) and without (blue arrow) CRM. Regions of interest (ROI)—bone, CRM and whole histology section area was masked (red color) and measured; FIG. 14B is an Amount (%) of newly formed bone (green), CRM (gray) and bone marrow (red) on whole histology section (magnification 1.25×) among different experimental groups; FIG. 14C is a Bone/bone marrow ratio of whole histology sections among different experimental groups, FIG. 14D is an Amount (%) of newly formed bone (green) and bone marrow (red) seen on 10× magnification—among experimental groups containing small bioceramic particles (area with CRM, area without CRM), medium and large (area between particles);

FIG. 14E is a Bone/bone marrow ratio among experimental groups containing small bioceramic particles (area with CRM, area without CRM), medium and large (area between particles); FIG. 14F is an Amount of cortical bone among experimental groups containing small, medium and large bioceramic particles; and (G)—Distance (µm) between particles among different experimental groups. Results are shown as mean±SD.

Figure 14G:
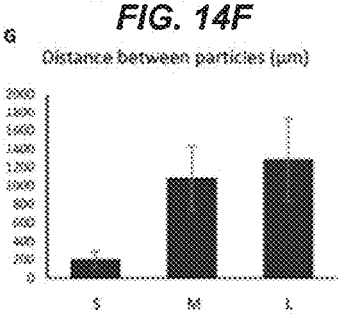
FIG. 14G is a chart showing a distance (μm) between particles among different experimental groups.

The main geometrical property of small particles was a large CRM surface and shorter distances between the particles (198 µm; FIG. 14G). The new bone was present on the surfaces and between bioceramic particles forming a dense bone network (FIG. 11). However, with the CRM/ABC ratio used BCS contained as well an area without bioceramic particles containing trabeculae, bone marrow and blood vessels (FIG. 11). The number of trabeculae was lower and the bone marrow occupied larger space than in the part containing bioceramic particles. The proportion of tissue components in BCS containing small particles is shown in FIGS. 14B and 14D. Histomorphometry revealed that in the part of BCS containing small particles proportion of bone was 38% and proportion of bone marrow 62%, while in the part without particles the proportion of bone was around 17% and proportion of bone marrow was almost 83% (FIG. 14D). Therefore bone/bone marrow ratio in the part with smallest particles was 0.65 compared to 0.21 in the part without particles (FIG. 14E). The overall bone/bone marrow ratio determined on the whole section was in between these two values (0.51). In the BCS containing particles the cortical bone was very discrete and in general formed only 27% of the total bone volume (FIG. 14F).

Figure 12:
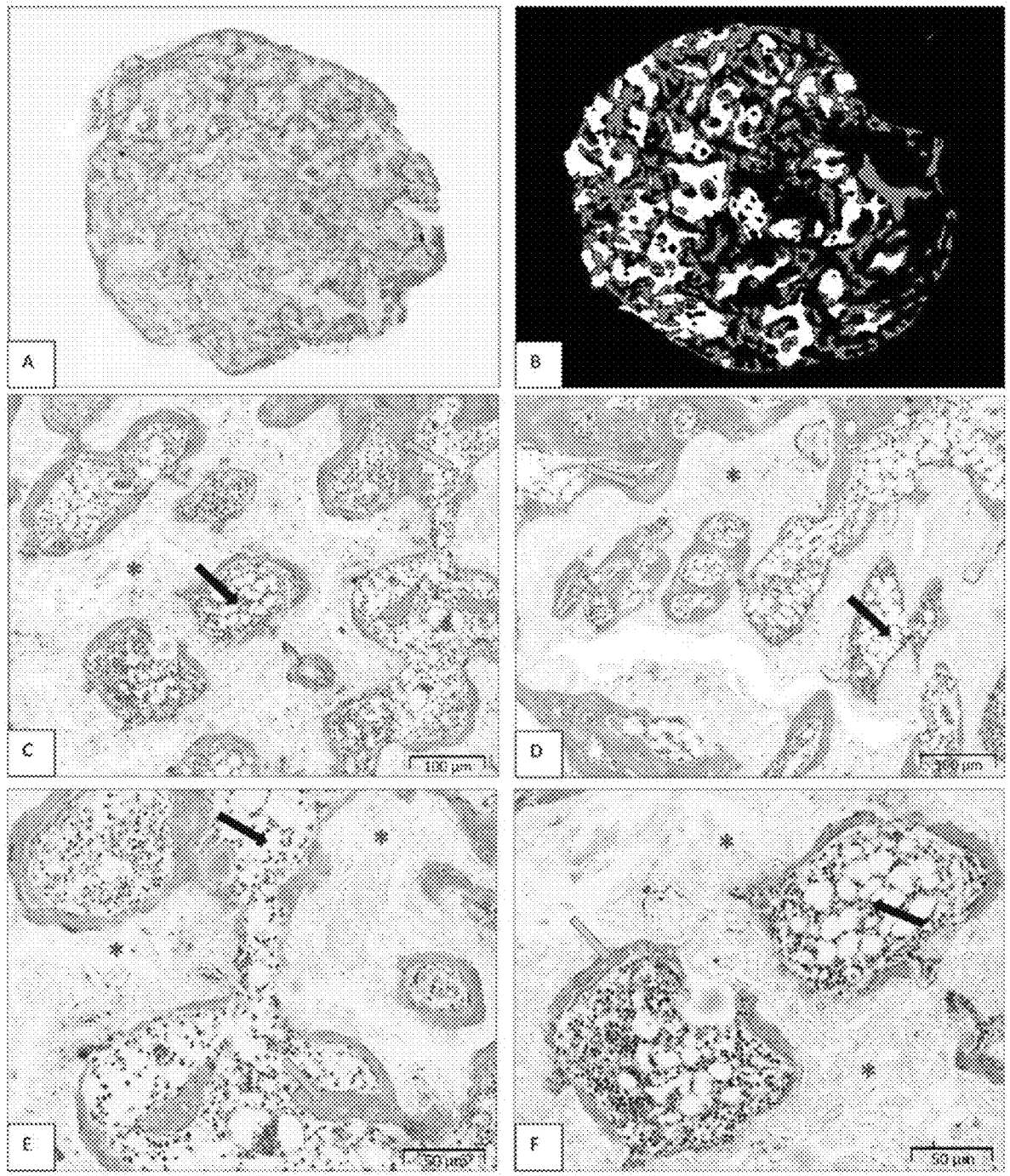
FIG. 12 shows bioceramic particles in a size range from 500 to 1700 µm (medium); (A)—Whole histology section of BCS with medium particles; (B)—Reconstructed image showing newly formed bone (green) and CRM (white); and (C, D, E, F)—Goldner trichrome stained histology sections.

Medium Particle (500-1700 µm) BCS Consisted of Pronounced Cortical Bone Outside, Trabecular Structure Between Particles and Abundant Bone Marrow Area Key geometrical properties of medium particles were a relatively smaller CRM surface area and larger distances between the particles (1075 µm; FIG. 14G) as compared to smaller particles. FIG. 12 shows bioceramic particles in size range from 500 to 1700 µm (medium): (A)—Whole histology section of BCS with medium particles; (B)—Reconstructed image showing newly formed bone (green) and CRM (white); and (C, D, E, F)—Goldner trichrome stained histology sections. Red asterisk indicates bioceramic particles. Yellow arrow indicates newly formed bone, while black arrow shows bone marrow. Another important feature of the medium size particles was the presence of large pores. BCS containing medium particles consisted of the cortical bone outside the new organ, bone covering the surfaces of bioceramic particles, and the bone trabeculae between bioceramic particles (FIG. 12). The cortical bone was pronounced and formed around 47% of the total bone volume. New bone around the bioceramic particles was separated on the bone present outside and inside the particles. The bone outside encircled the bioceramic particles and continued either as a cortical bone or as trabeculae connecting adjacent ceramic particles. Inside the pores, newly formed bone covered the bioceramic surfaces and encircled the pores containing bone marrow. Bone trabeculae and bone marrow were present both between bioceramic particles and in the area between particles and the cortical bone. The proportion of tissue components is shown in FIGS. 14B and 14D. Bone/bone marrow ratio was similar when determined in the entire area (0.29) and between the particles (0.20) (FIG. 14C and FIG. 14E).

Figure 13:
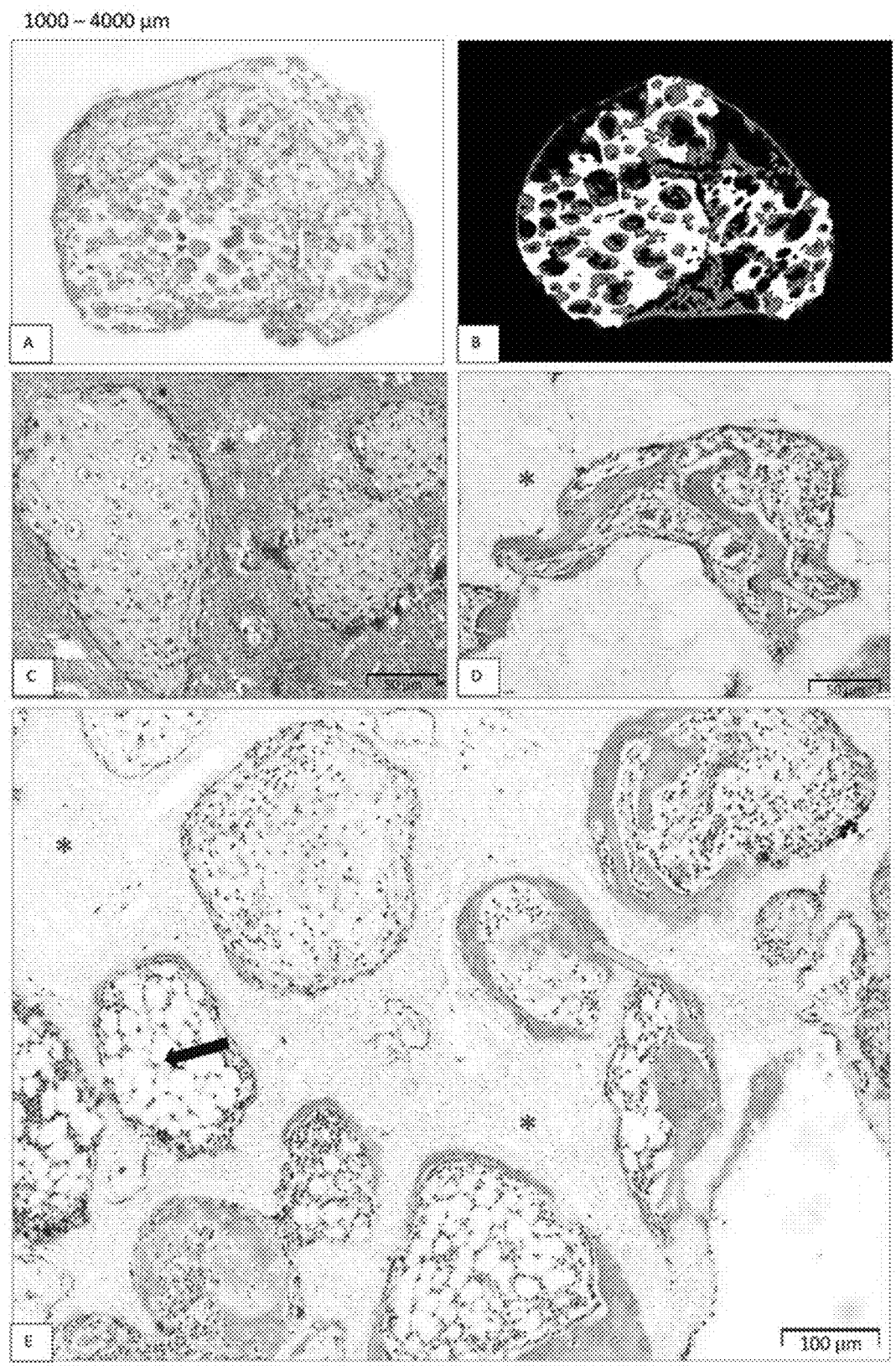
FIG. 13 shows bioceramic particles in size range from 1000 to 4000 µm (large); (A)—Whole histology section of BCS with medium particles; (B)—Reconstructed image showing newly formed bone (green) and CRM (white), (C)—Hematoxylin and eosin and (D, E)—Goldner trichrome stained histology.

Large Particles (1000-4000 μm) BCS had Similar Tissue Pattern as BCS Containing Medium Particles with Unsynchronized Ossification in the Pores FIG. 13 shows bioceramic particles in a size range of from 1000 to 4000 μm (large): (A)—Whole histology section of BCS with medium particles; (B)—Reconstructed image showing newly formed bone (green) and CRM (white); (C)—Hematoxylin and eosin and (D, E)—Goldner trichrome stained histology sections. Black (HA), red (TCP) and blue (BCP) asterisk indicated different chemical composition of bioceramic particles. Yellow arrow indicates newly formed bone, while white arrow shows bone marrow.

Bioceramic particles in this group were significantly larger than medium particles and contained more pores forming a complex pore network within the particles. However, the geometrical properties of large particles were similar to medium particles: overall CRM surface area was smaller while the distances between the large particles (1279 μm) was significantly higher than the distances between smaller particles (198 μm). Therefore, the tissue pattern of BCS containing large particles was more similar to the appearance of BCS containing medium particles (FIG. 13). Thus, the new bone was divided into cortical bone forming BCS boundaries, bone at the surfaces and in the pores of particles and the bone trabeculae between bioceramic particles. Similar to BCS containing medium particles, cortical bone was more pronounced and formed around 40% of the total bone volume. On μCT and histology sections, newly formed bone was present in the majority of pores while few of them contained fibrocartilaginous tissue and remnants of ABC. Interestingly, in several specimens a unique tissue differentiation pattern was discovered: namely, different large pores within the same section contained different stages of ossification from chondrocytes resembling similar areas as on day 7 of the endochondral ossification in the rat assay to newly formed bone and bone marrow with predominance of hematopoietic cells and new bone and bone adipocytic marrow (FIG. 13). The proportion of tissue components is shown in FIG. 14B and FIG. 14D. Bone/bone marrow ratio was determined both on whole section (0.29) and between the particles (0.19) and was comparable with the one in BCS containing the medium particles (FIGS. 14C and 14E).

Histomorphometrical Analysis

Histomorphometrical analysis was conducted to analyze the proportions of bone, CRM and bone marrow tissue components in BCS, to analyze distances between bioceramic particles and to analyze proportion of the cortical bone in the total bone volume. Moreover, in order to describe relations between bone and bone marrow a bone/bone marrow index was introduced. Results of histomorphometry are summarized in FIG. 14.

First, the proportions of tissue components in BCS on histological sections through the entire implant (FIG. 14A) were analyzed. Regardless of different sizes and the chemical composition of particles in newly induced organs the different organizational tissue patterns, bone marrow was the most prevalent tissue in all groups, followed by bioceramic particles and then by the bone (FIG. 14B). The proportion of bone as well as bone/bone marrow ratio was higher in tissue patterns containing small particles than in medium and large particles (0.51 compared to 0.29 and 0.29, respectively; FIG. 14C).

Due to nonhomogeneous distribution of the small particles, the proportion of bone and bone marrow between the particles and in the part without ceramic particles was analyzed. In the part containing particles, bone/bone marrow ratio was 0.65. On the other hand, in the part without particles it was 0.21 which was comparable with bone/bone marrow ratio between medium and large particles (0.20 and 0.19, respectively) (FIG. 14E).

The inter-particle distance (FIG. 14G) was significantly higher in BCS containing large (1279 μm) and medium (1075 μm) particles than the small particles (198 μm).

The proportion of cortical bone in the total bone volume (FIG. 14H) was significantly higher in BCS containing large and medium particles (40 and 47% of total bone volume, respectively) than in BCS containing small particles (27% of total bone volume).

Conclusion

In Example 2, in parallel in vivo response to ectopic implantation of rhBMP6 in autologous blood coagulum (ABC) containing various bioceramic particles which differed in chemical composition (TCP, HA and BCP) and particle size (74-420 μm, 500-1700 μm and 1000-4000 μm) was tested. Moreover, two methods of BMP6 application in implant and various CRM/ABC implant ratios were tested. The preclinical safety and efficacy of rhBMP6 in ABC has been explored in various animal species and orthopaedic models without and with allograft as compression resistant matrix (15, 22, 27).

Although previous research focused on osteoconductivity of bioceramic which differs in chemical composition (TCP, HA and BCP with different TCP/HA ratios) it is still unclear if chemical composition of bioceramics affects osteoconductivity because obtained results so far were not consistent (3, 21, 33). In the present invention, it has been demonstrated that TCP and HA as well as BCP possess excellent osteoconductive properties. However, results indicate that neither of them might be considered as more osteoconductive. Although TCP and HA provide similar osteoconductivity it is well known that they significantly differ regarding the resorption rates.

There are only few publications focused on the influence of particle size on bone induction and it is unknown whether the particle size affects osteogenesis, the amount of newly formed bone and the resorption rate of bioceramic particles (23) (Jung, 2006). Moreover, in the previous studies osteoconductivity of only smaller particles (<1000 μm) were compared. In an investigation comparing two different particle size (50-150 μm and 150-500 μm) with added rhBMP4 there was no significant difference in the amount of new bone (23) (Jung, 2006) while in the study comparing osteoconductive capability of two groups of deproteinized bone particles (300-500 μm and 850-1000 μm), the use of smaller particles showed higher bone density (34) (Xu, 2002). In the present invention, ABGS containing all tested particle size ranges induced extensive amount of bone. When the differences between groups were significant they were always in favor of smaller particles regarding bone volume and trabecular number, while the trabecular thickness was in favor of larger particles. Moreover, the particle size and geometry of particles determined the structure of newly formed bone. Small particles possessed a large surface area and the distances between particles were smaller. Therefore, small particles guided formation of a dense bone network surrounding bioceramic particles. On the other hand, medium and large particles possess smaller surface area and larger distance between particles as compared to smallest particles. Larger distances between medium and large particles correlated with significantly lower bone/bone marrow ratio than in BCS containing small particles. However, BCS with medium and large particles contained pronounced cortical bone while in BCS containing small particles cortical bone was discreet. Moreover, large and medium particles possess large pores which increase the surface area and allowed bone ingrowth.

Small, medium and large particles significantly differed in bone-ceramic structure, and in the engineered constitutive tissues comprising different patterns of newly formed ectopic organs with eventually different function and biomechanical properties on day 21. Thus, the function of such ABGS may be different from these containing smaller particles due to significant differences in tissue pattern and composition influencing potentially the maintenance of long term biomechanical properties.

Bone induction by rhBMPs lyophilized on bioceramics has been previously demonstrated (21, 23, 21) (Alam, 2001; Jung, 2006; Kim, 2011). In the present invention, it has been demonstrated bone formation induced by rhBMP6 lyophilized on various bioceramic particles and compared the amount and bone properties of newly formed bone with the bone induced by the same amount of rhBMP6 added in blood and mixed with bioceramics. Efficacy of ABGS containing rhBMP6 without CRM has been shown in preclinical rabbit ulnar segmental defect while efficacy with and without allograft as CRM was shown in rabbit and ovine posterolateral spinal fusion study (15, 22) (Grgurevic, Vukicevic). Results of the present invention indicate that lyophilizing rhBMP6 on bioceramics is an equally efficient alternative and that both methods of BMP6 application may be used Ratio between bioceramic mass and autologous blood coagulum volume (CRM/ABC ratio) is an important feature while defining osteoinductive device containing rhBMP6, bioceramics and ABC. µCT analyses revealed that volume of newly formed bone was significantly higher in BCS derived from ABGS containing higher CRM/ABC ratio (0.1-0.125 g/500 µL). Explanation of observed trend lies in the increase in overall surface area following increase in the volume/number of bioceramic particles. Moreover, another advantage of aforementioned CRM/ABC ratio is the uniform distribution of particles (>1000 µm) in ABC and therefore it may be considered the preferred ratio.

Example 3—OPS-20190529/Subcutaneous Implant Assay/Rats

Example 3 describes a time course of ectopic bone formation induced by ABGS containing rhBMP6 in ABC with various compression resistant matrices (BCP 74-420 µm, BCP 500-1700 µm, BCP 1000-4000 µm). Ectopic bone formation was analysed using MicroCT (FIGS. 15-16) and on histological sections (FIG. 17).

Materials & Methods

Subcutaneous implant assay was conducted in Sprague Dawley rats to determine time course of ectopic bone formation and bone remodeling which occur after implantation of autologous bone graft substitute (ABGS) containing recombinant human Bone Morphogenetic Protein 6 (rhBMP6) in autologous blood coagulum (ABC) combined with various-size (74-420 µm, 500-1700 µm and 1000-4000 µm) biphasic (80% TCP/20% HA) bioceramic particles. In this example 75 Sprague Dawley rats (lat. *Rattus norvegicus*, male and female, 6-8 weeks old) were used, which were assigned to 3 experimental groups with 5 different follow-up periods (7, 14, 21, 35 and 50 days) according to the experimental design presented in Table 8.

Blood samples were collected into tubes without an anticoagulant substance in a volume of 500 µL. rhBMP6 (20 µg) was put in blood and mixed with bioceramics. A vertical incision (1 cm) was made under sterile conditions in the skin over the thoracic region, and the pockets were prepared by a blunt dissection on both sides of the incision (in the left and right axillary region). ABGS implants were implanted deep into the pockets (two implants per animal), and the incision was closed with a surgical clip. At the end of the follow-up period animals were euthanized and implants were removed for further analyses.

Results

Figure 15:
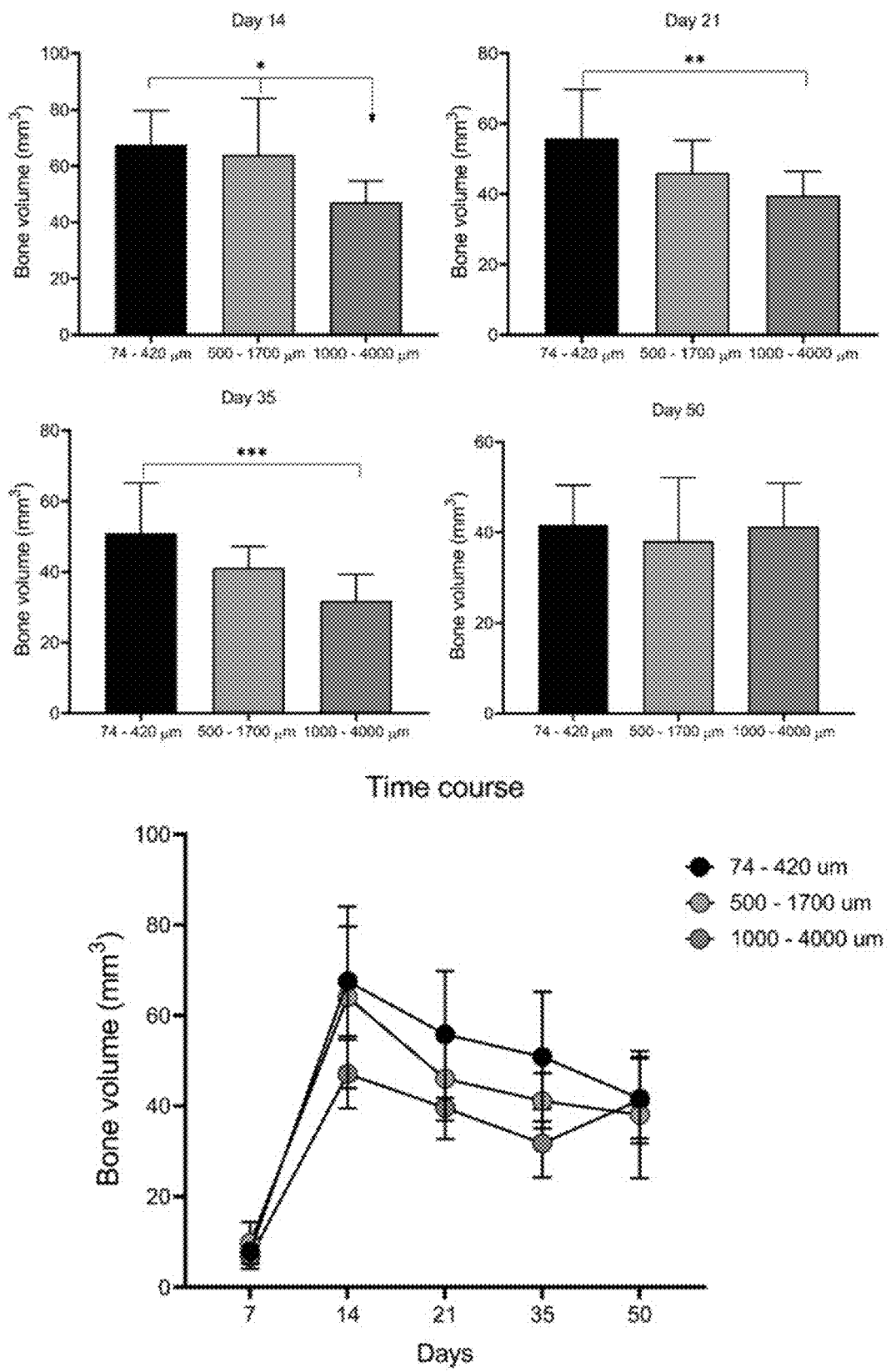
FIG. 15 is a series of charts showing a bone volume over time when using different particle sizes.
Figure 16:
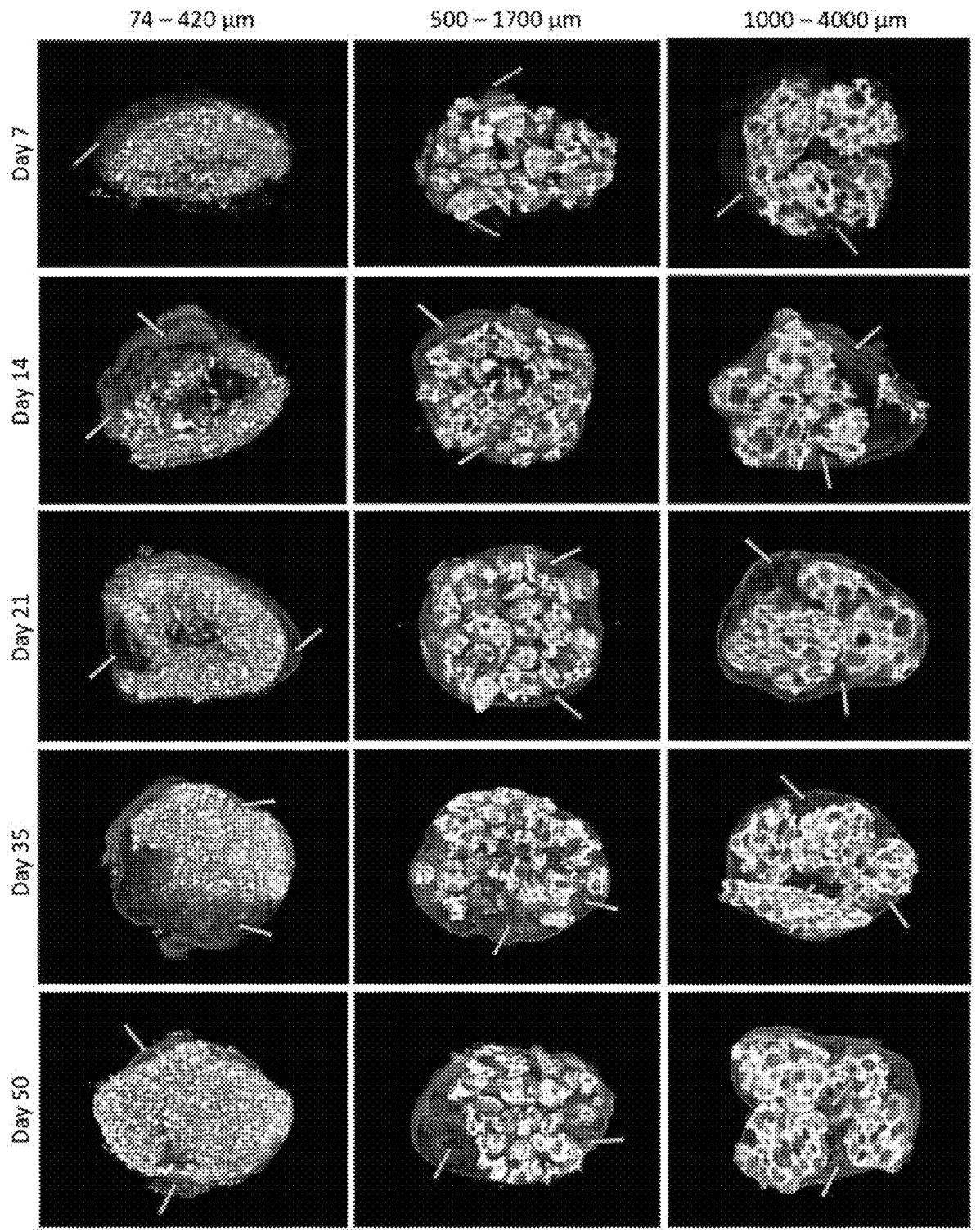
FIG. 16 is a series of MicroCT images on day 7, 14, 24, 35 and 50 showing newly formed bone in the BCS for different particle sizes.
Figure 17:
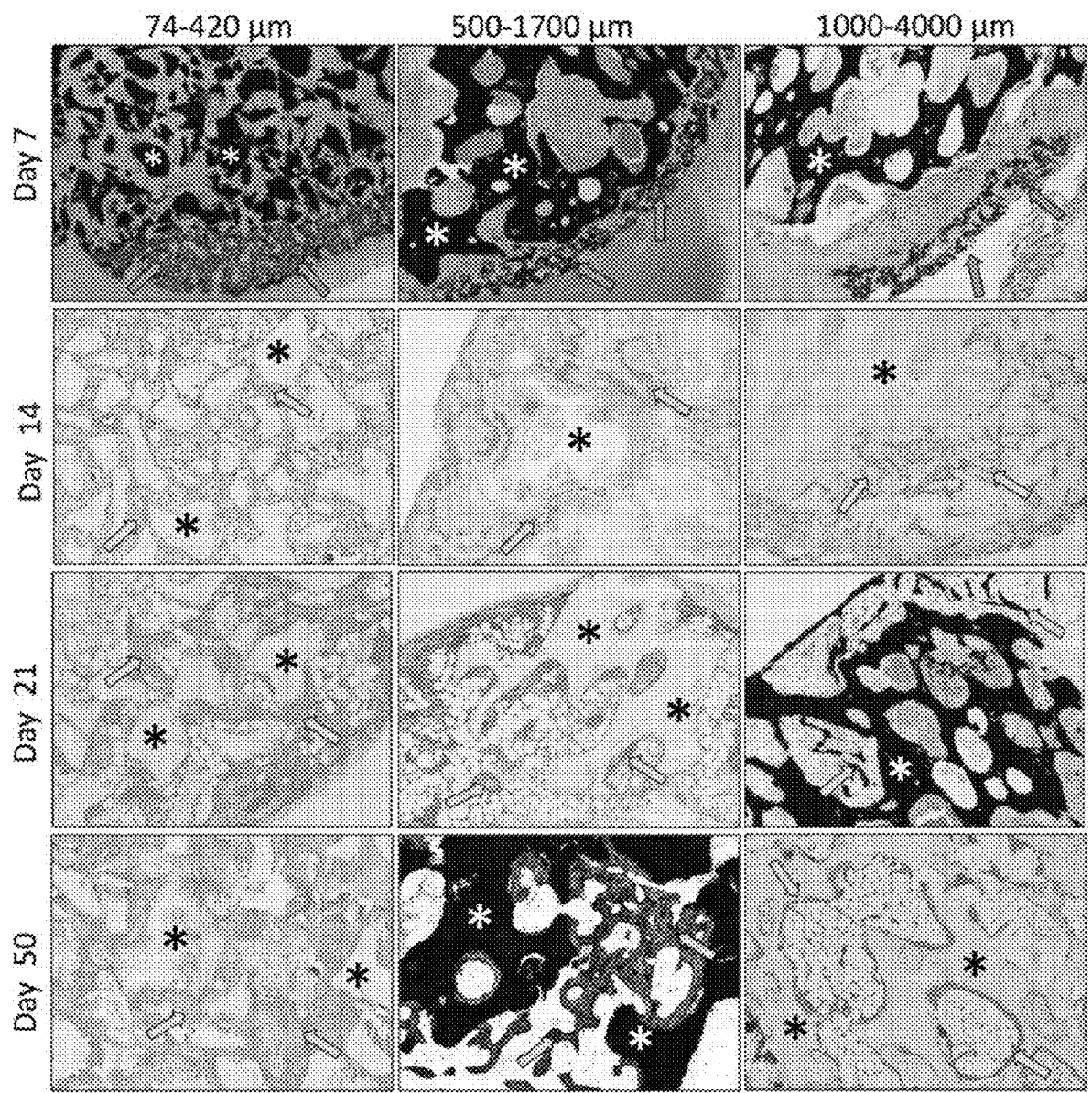
FIG. 17 are images of histological sections on day 7, 14, 21, and 50 showing newly formed bone in the BCS for different particle sizes.

Results are presented in Table 8 and FIGS. 15-17.

TABLE 8

Example 3 - OPS-20190529 Groups and results

| Group | Group description | Time point | Result |
|---|---|---|---|
| A | BCP (TCP/HA 80/20) 74-420 µm + ABGS (20 µg rhBMP6 in 500 µL ABC) (n = 10) | 7 days | Endochondral ossification was present in the peripheral areas of all ABGS implants while central part contained bioceramic particles and osteogenic cells which were present on the surfaces and between the particles. |
| B | BCP (TCP/HA 80/20) 500-1700 µm + ABGS (20 µg rhBMP6 in 500 µL ABC) (n =10) | | |
| C | BCP (TCP/HA 80/20) 1000-4000 µm + ABGS (20 µg rhBMP6 in 500 µL ABC) (n = 10) | | |
| A | BCP (TCP/HA 80/20) 74-420 µm + ABGS (20 µg rhBMP6 in 500 µL ABC) (n = 10) | 14 days | Newly formed bone was induced in all ABGS implants (30/30). Newly formed bone along with bioceramic particles formed bone-ceramic structure (BCS). BCS with small particles contained dense bone network between the particles while BCS with large and medium particles contained cortical bone, bone on the surfaces and trabeculae between the particles. |
| B | BCP (TCP/HA 80/20) 500-1700 µm + ABGS (20 pg rhBMP6 in 500 µL ABC) (n = 10) | | |
| C | BCP (TCP/HA 80/20) 1000-4000 µm + ABGS (20 µg rhBMP6 in 500 µL ABC) (n = 10) | | |
| A | BCP (TCP/HA 80/20) 74-420 pm + ABGS (20 µg rhBMP6 in 500 µL ABC) (n = 10) | 21 days | Newly formed bone was present in all ABGS implants (30/30). Newly formed bone along with bioceramic particles formed bone-ceramic structure (BCS). A substantial number of adipocytes was present in bone marrow. |
| B | BCP (TCP/HA 80/20) 500-1700 µm + ABGS (20 µg rhBMP6 in 500 µL ABC) (n = 10) | | |
| C | BCP (TCP/HA 80/20) 1000-4000 µm + ABGS (20 µg rhBMP6 in 500 µL ABC) (n =10) | | |
| A | BCP (TCP/HA 80/20) 74-420 µm + ABGS (20 µg rhBMP6 in 500 µL ABC) (n = 10) | 35 days | Newly formed bone was present in all ABGS implants (30/30). Newly formed bone along with bioceramic particles formed bone-ceramic structure (BCS). Adipocytes were predominant cells in bone marrow. |
| B | BCP (TCP/HA 80/20) 500-1700 µm + ABGS (20 µg rhBMP6 in 500 µL ABC) (n =10) | | |
| C | BCP (TCP/HA 80/20) 1000-4000 µm + ABGS (20 µg rhBMP6 in 500 µL ABC) (n = 10) | | |

TABLE 8-continued

Example 3 - OPS-20190529 Groups and results

| Group | Group description | Time point | Result |
|-------|-------------------|------------|--------|
| A | BCP (TCP/HA 80/20) 74-420 μm + ABGS (20 μg rhBMP6 in 500 μL ABC) (n = 10) | 50 days | Newly formed bone was present in all ABGS implants (30/30). Newly formed bone along with bioceramic particles formed bone-ceramic structure (BCS). Adipocytes were predominant cells in bone marrow. |
| B | BCP (TCP/HA 80/20) 500-1700 μm + ABGS (20 μg rhBMP6 in 500 μL ABC) (n = 10) | | |
| C | BCP (TCP/HA 80/20) 1000-4000 μm + ABGS (20 μg rhBMP6 in 500 μL ABC) (n = 10) | | |

On MicroCT images newly formed bone was present in all samples. MicroCT analyses revealed that the amount of newly formed bone in all groups was highest on day 14 and later decreased in time (FIG. 15). The amount of newly formed bone was highest in group which contained small bioceramic particles (BCP 74-420 μm) compared to groups which contained large and medium particles (1000-4000 μm and 500-1700 μm) (FIG. 15).

On day 7 after implantation large zones of endochondral ossification were present in the peripheral parts on histological sections of ABGS implants containing rhBMP6 in ABC mixed with compression resistant matrix (BCP 74-420 μm, BCP 500-1700 μm or BCP 1000-4000 μm) (FIG. 17). Importantly, osteogenic cells were lined on the surfaces of bioceramic particles regardless their size.

On day 14 following implantation newly formed bone was present in all ABGS implants containing rhBMP6 in ABC combined with various bioceramic particles (FIG. 17). In group containing small particles newly formed BCS consisted of the part with particles and part without particles. On histological sections of samples containing large and medium bioceramic particles newly formed bone was present around and between particles and also in the pores. Osteoblasts on the surfaces of bioceramic particles formed bone intramembranously on the surfaces of bioceramic particles. Bone between large and medium particles was formed endochondraly and intramembranously. Intramembranous ossification was still ongoing both between and on the surfaces of bioceramic particles. Bone marrow was present between trabeculae of bone and there were only few adipocytes in bone marrow.

On day 21 after implantation, ectopic bone formation has finished and newly formed bone with bioceramic particles formed complex construct which in this application is referred to as bone-ceramic structure (BCS) (FIG. 16-17). Uneven particle distribution in the BCS led to a BCS having a part with bioceramic particles and a part without bioceramic particles. In the part with bioceramic particles, newly formed bone formed dense network surrounding particles and limited bone marrow while part without particles consisted of few trabeculae and extensive bone marrow. BCS containing large and medium bioceramic particles consisted of pronounced cortical bone forming boundaries, bone present on the surfaces and in the pores of bioceramic particles and trabeculae between the particles.

Histological finding on day 35 and day 50 following implantation revealed that BCS was formed in all ABGS implants containing rhBMP6 in autologous blood coagulum combined with various bioceramic particles (FIG. 17). BCS containing small particles consisted of a part containing particles and a part without particles. In a part with particles dense bone surrounded and connected bioceramic particles while in the part without particles, there were only few trabeculae. Areas of bone marrow were significantly larger in the part of BCS without particles than in the part with particles. In both compartments, adipocytes were predominant cells in bone marrow.

On histological sections of BCS containing large and medium bioceramic particles bone was divided into bone on the surfaces of particles and inside the pores, cortical bone and trabeculae between the particles. However, trabecular bone was partially resorbed and replaced with adipocytes which were predominant cells in bone marrow.

Example 4—OPS-20191119/Subcutaneous Implant Assay/Rats

Example 4 describes a time course of ectopic bone formation following subcutaneous implantation of ABGS implants containing rhBMP6 in ABC with bioceramic macropous blocks in a form of a cylinder. In this example 30 Sprague Dawley rats (lat. *Rattus norvegicus*, male and female, 6-8 weeks old) were used, which were assigned to two experimental groups with five different follow-up period (7, 14, 21, 35 and 50 days) according to the experimental design presented in Table 9.

Materials & Methods

Rat subcutaneous implant assay was conducted to determine time course of ectopic bone formation after implantation of autologous bone graft substitute (ABGS) containing recombinant human Bone Morphogenetic Protein 6 (rhBMP6) in autologous blood coagulum (ABC) combined with biphasic (80% TCP/20% HA) bioceramic macroporous blocks in the form of a cylinder.

Blood samples were collected into tubes without an anticoagulant substance in a volume of 500 μL. rhBMP6 (20 μg) was put in blood and mixed with bioceramics. A vertical incision (1 cm) was made under sterile conditions in the skin over the thoracic region, and the pockets were prepared by a blunt dissection on both sides of the incision (in the left and right axillary region). ABGS implants were implanted deep into the pockets (two implants per animal), and the incision was closed with a surgical clip. At the end of the follow-up period animals were euthanized and implants were removed for further analyses.

Results

Results are presented in Table 9 and FIG. 18.

TABLE 9

Example 4—OPS-20191119 Groups and results

| Group | Group description | Time point | Result |
|-------|-------------------|------------|--------|
| A | BCP (TCP/HA 80/20) cylinder (30:1) + ABGS (20 μg rhBMP6 in 500 μL ABC) (n = 6) | 7 days | Endochondral ossification was present in the peripheral areas of all ABGS implants while central part contained bioceramic blocks and osteogenic cells which were present on the bioceramic surfaces and inside the pores. |
| B | BCP (TCP/HA 80/20) cylinder (35:1) + ABGS (20 μg rhBMP6 in 500 μL ABC) (n = 6) | | |
| A | BCP (TCP/HA 80/20) cylinder (30:1) + ABGS (20 μg rhBMP6 in 500 μL ABC) (n = 6) | 14 days | Newly formed bone was induced in all ABGS implants (12/12). Newly formed bone along with |

TABLE 9-continued

Example 4—OPS-20191119 Groups and results

| Group | Group description | Time point | Result |
|---|---|---|---|
| B | BCP (TCP/HA 80/20) cylinder (35:1) + ABGS (20 μg rhBMP6 in 500 μL ABC) (n = 6) | | macroporous bioceramic blocks formed bone-ceramic structure (BCS). |
| A | BCP (TCP/HA 80/20) cylinder (30:1) + ABGS (20 pg rhBMP6 in 500 μL ABC) (n = 6) | 21 days | Newly formed bone was induced in all ABGS implants (12/12). Newly formed bone along with |
| B | BCP (TCP/HA 80/20) cylinder (35:1) + ABGS (20 μg rhBMP6 in 500 μL ABC) (n = 6) | | macroporous bioceramic blocks formed bone-ceramic structure (BCS). |
| A | BCP (TCP/HA 80/20) cylinder (30:1) + ABGS (20 μg rhBMP6 in 500 μL ABC) (n = 6) | 35 days | Newly formed bone was induced in all ABGS implants (12/12). Newly formed bone along with |
| B | BCP (TCP/HA 80/20) cylinder (35:1) + ABGS (20 μg rhBMP6 in 500 μL ABC) (n = 6) | | macroporous bioceramic blocks formed bone-ceramic structure (BCS). Adipocytes were predominant cell population in bone marrow. |
| A | BCP (TCP/HA 80/20) cylinder (30:1) + ABGS (20 μg rhBMP6 in 500 μL ABC) (n = 6) | 50 days | Newly formed bone was induced in all ABGS implants (12/12). Newly formed bone along with |
| B | BCP (TCP/HA 80/20) cylinder (35:1) + ABGS (20 μg rhBMP6 in 500 μL ABC) (n = 6) | | macroporous bioceramic blocks formed bone-ceramic structure (BCS). Adipocytes were predominant cell population in bone marrow. |

FIG. 18 illustrates MicroCT analysis and microCT/histological sections through the implants. FIG. 18A is MicroCT analyses and reconstructed images (RI) of autologous bone graft substitute (ABGS) with ceramic blocks showing ceramics (white) on day 7 and then newly formed bone (green) and ceramics (white) on days 14, 21, 35, and 50. Newly formed bone was uniformly present inside the cylinder while the cortical bone encircled the cylinder outside. FIG. 18B is Bone volume (mm3) among experimental groups throughout the follow-up period. The amount of newly formed bone reached its peak on day 14 and then decreased towards day 50. Two-way analysis of variance with Tukey's multiple comparisons test was performed. Values are expressed as mean±SD. P values are marked with asterisk; *P≤0.05, P≤0.01, *P≤0.001. FIG. 18C illustrates Histological sections through bone-ceramic structure (BCS) consisting of newly formed bone and various cylindrical ceramic blocks (yellow asterisk) containing pores (red asterisk) on day 35. Pronounced cortical bone (green arrow) formed boundaries of newly formed BCS.

MicroCT analyses revealed that ABGS implants induced formation of bone-ceramic structure (BCS) in all animals (FIG. 18A). The amount of newly formed bone was highest on day 14 and then decreased towards day 50 (FIG. 18B).

On day 7 after implantation areas of endochondral ossification were present in the peripheral part of the implants while the central part contained porous cylinder containing ABC remnants in pores.

On day 14 after implantation newly formed bone was present on all histological sections of ABGS implants. Newly formed bone and cylinders together formed complex, vascularized, tissue engineered construct which is referred to in this application as bone-ceramic structure (BCS). Newly formed bone was divided into cortical bone, bone on the outer and inner surfaces of cylinder and bone trabeculae inside the pores. Cortical bone was present outside the cylinder forming boundaries of the newly formed BCS. Inside the cylinder, bone was uniformly present in the pores regardless of pore position inside the cylinder. In the pores, bone covered the surface of the bioceramics encircling pores with bone. Moreover, pores contained dense trabecular network. Bone marrow was present between trabeculae of bone. There were only few adipocytes in bone marrow.

On day 21 following implantation, the microarchitecture of BCS was similar as on day 14. However, outside the cylinder cortical bone was more pronounced, while inside the pores number and thickness of trabeculae decreased. There were more adipocytes in bone marrow compared to day 14.

Histological findings on day 35 and day 50 were very similar and it seems that ectopic osteogenesis reached its final stage. Outside the cylinder, pronounced cortical bone formed the boundaries of BCS while inside the cylinder, in the pores, bone completely covered the surface of the bioceramics encircling pores with bone (FIG. 18C). Inside the osseus circle, there were few trabeculae and bone marrow with predominance of adipocytes.

Example 5—OPS-20190205/Subcutaneous Implant Assay/Rats

The present example describes how addition of various amount of bioceramic particles to ABGS (rhBMP6 in autologous blood coagulum) affects the amount and the structure of the newly formed bone. In this example 30 Sprague Dawley rats (lat. *Rattus norvegicus*, male and female, 6-8 weeks old) were used, which were assigned to 6 experimental groups according to the experimental design presented in Table 10.

Materials & Methods

Subcutaneous implant assay was conducted in Sprague Dawley rats to investigate how addition of various amount of bioceramic particles to ABGS (rhBMP6 in autologous blood coagulum) affects the amount and the structure of the newly formed bone.

Blood samples were collected into tubes without an anticoagulant substance in a volume of 500 μL rhBMP6 (20 μg) was put in blood and mixed with the amount of bioceramics as specified in Table 10. A vertical incision (1 cm) was made under sterile conditions in the skin over the thoracic region, and the pockets were prepared by a blunt dissection on both sides of the incision (in the left and right axillary region). ABGS implants were implanted deep into the pockets (two implants per animal), and the incision was closed with a surgical clip. After 21 day animals were euthanized and implants were removed for further analyses.

Results

Results are presented in Table 10 and FIG. 19.

TABLE 10

Example 5 - OPS-20190205 Groups and results

| Group | Group description | Result |
|---|---|---|
| A | ABGS (rhBMP6 in ABC) (n = 10) | Newly formed bone was induced in all (60/60) ABGS implants. |
| B | 25 mg BCP (TCP/HA 80/20) 1000-4000 μm + ABGS (20 μg rhBMP6 in 500 μL ABC) (n = 10) | The addition of bioceramic particles in the ABGS |

TABLE 10-continued

Example 5 - OPS-20190205 Groups and results

| Group | Group description | Result |
|---|---|---|
| C | 50 mg BCP (TCP/HA 80/20) 1000-4000 µm + ABGS (20 µg rhBMP6 in 500 µL ABC) (n = 10) | significantly increased the amount of newly formed bone. The amount of newly formed bone in bone-ceramic structure (BCS) correlated with the increase in amount of used bioceramics. The optimal CRM/ABC ratio was found to be 100-125 mg/500 µL ABC. |
| D | 75 mg BCP (TCP/HA 80/20) 1000-4000 µm + ABGS (20 µg rhBMP6 in 500 µL ABC) (n = 10) | |
| E | 100 mg BCP (TCP/HA 80/20) 1000-4000 µm + ABGS (20 µg rhBMP6 in 500 µL ABC) (n = 10) | |
| F | 125 mg BCP (TCP/HA 80/20) 1000-4000 µm + ABGS (20 µg rhBMP6 in 500 µL ABC) (n = 10) | |

Figures 19A, 19B, 19C:
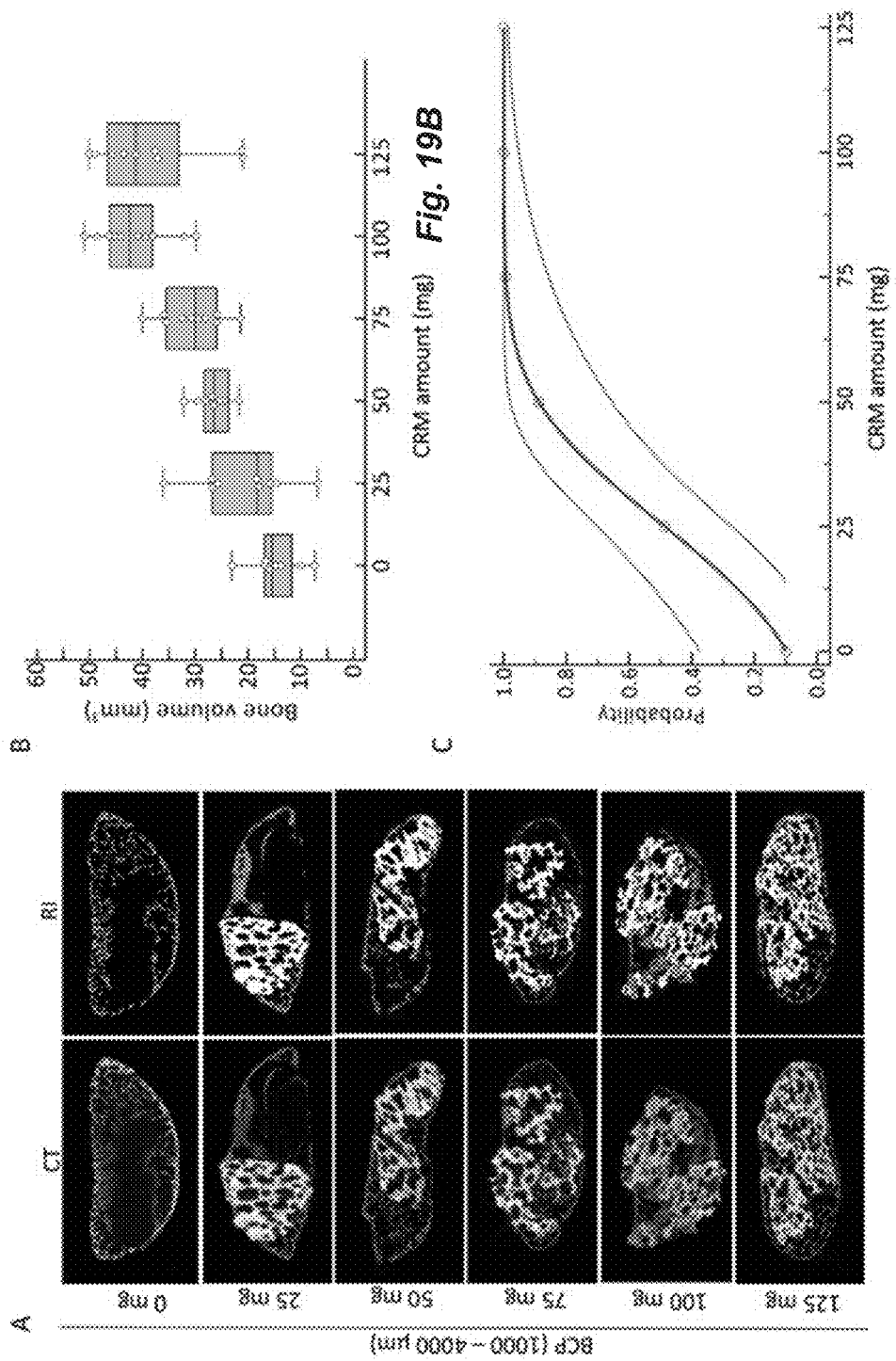
FIG. 19A shows MicroCT images of ABGS showing an increasing mass of the similar ceramic particles in equal blood volume.
FIG. 19B is a graph illustrating Bone volume ($mm^3$) among experimental groups (from 0 to 125 mg BCP per implant) on day 21 shown as median with interquartile range (IQR).
FIG. 19C is graph illustrating Probit regression (Dose-Response) analysis with the value defined as a satisfactory bone volume fixed at 20 $mm^3$ as measured by MicroCT.

FIG. 19A shows MicroCT images of ABGS showing an increasing mass of the similar ceramic particles in equal blood volume. Reconstructed images (RI) of ABGS showing newly formed bone (green) and ceramics (white). FIG. 19B is a graph illustrating Bone volume (mm3) among experimental groups (from 0 to 125 mg BCP per implant) on day 21 shown as median with interquartile range (IQR). Non-parametric Kruskal Wallis test was used with post hoc Mann Whitney U-test. FIG. 19C is graph illustrating Probit regression (Dose-Response) analysis with the value defined as a satisfactory bone volume fixed at 20 mm3 as measured by MicroCT. Overall regression model fit was statistically significant (Null model −2 Log Likelihood=60.15; Full model −2 Log Likelihood=24.92; Chi-squared=35.22; DF=1; P<0.0001) with Nagelkerke R2=71.12%; n=10 per group.

MicroCT analyses revealed that the addition of bioceramic particles in the ABGS significantly increased the amount of newly formed bone (FIG. 19) with highest bone volume in groups containing 100-125 mg of bioceramics in 500 µL of ABC (FIGS. 19B-C).

On histological sections of implants containing bioceramics newly formed bone was present both outside the particles and in the pores inside. Newly formed bone connected different particles forming cortical bone in the peripheral parts of implants and osseous trabeculae and bone marrow in the central parts of implants.

The optimal CRM/ABC ratio was found to be 100-125 mg/500 µL ABC and this ratio was used in all subsequent experiments.

Example 6—OPS-20190402/Subcutaneous Implant Assay/Rats

The present example describes a Rat subcutaneous implant assay which was conducted to investigate whether the size and chemical composition of the bioceramic particles affect the amount and the structure of newly induced bone by autologous bone graft substitute (ABGS) comprised of rhBMP6 in autologous blood coagulum with bioceramics as compression resistant matrix (CRM). In this example 45 Sprague Dawley rats (lat. *Rattus norvegicus*, male and female, 6-8 weeks old) were used, which were assigned to 9 experimental groups according to the experimental design presented in Table 11.

Materials & Methods

Tested bioceramic particles differed in particle size (1000-4000 µm, 500-1500 µm and 74-420 µm) and chemical composition of particles (hydroxyapatite-HA, tricalcium phosphate-TCP and biphasic bioceramics-BCP).

Blood samples were collected into tubes without an anticoagulant substance in a volume of 500 µl. rhBMP6 (20 µg) was put in blood and mixed with bioceramics. A vertical incision (1 cm) was made under sterile conditions in the skin over the thoracic region, and the pockets were prepared by a blunt dissection on both sides of the incision (in the left and right axillary region). ABGS implants were implanted deep into the pockets (two implants per animal), and the incision was closed with a surgical clip. After 21 day animals were euthanized and implants were removed for further analyses.

Results

Results are presented in Table 11 and FIGS. 20-23.

TABLE 11

Example 6—OPS-20190402 Groups and results

| Group | Group description | Result |
|---|---|---|
| A | HA 1000-4000 µm + ABGS (20 µg rhBMP6 in 500 µL ABC) (n = 10) | Newly formed bone was induced in all (90/90) ABGS implants. The amount and structure of newly formed bone induced by ABGS implants were dependent on the particle size and not on chemical composition of bioceramics. Significantly higher amount of newly formed bone was formed in ABGS implants containing small (74-420 µm) and medium (500-1700 µm) than large (1000-4000 µm) particles. Bone-ceramic structure (BCS) with small particles consisted of a dense bone network between the particles while BCS with medium and large particles consisted of cortical bone, bone on the bioceramic surfaces and trabeculae surrounded with abundant bone marrow between the particles. |
| B | HA 500-1500 µm + ABGS (20 µg rhBMP6 in 500 µL ABC) (n =10) | |
| C | HA 74-420 µm + ABGS (20 µg rhBMP6 in 500 µL ABC) (n = 10) | |
| D | TCP 1000-4000 µm + ABGS (20 µg rhBMP6 in 500 µL ABC) (n = 10) | |
| E | TCP 500-1500 µm + ABGS (20 µg rhBMP6 in 500 µL ABC) (n = 10) | |
| F | TCP 74-420 µm + ABGS (r20 µg rhBMP6 in 500 µL ABC) (n = 10) | |
| G | BCP (TCP/HA 80/20) 1000-4000 µm + ABGS (20 µg rhBMP6 in 500 L ABC) (n =10) | |
| H | BCP (TCP/HA 80/20) 500-1500 µm + ABGS (20 µg rhBMP6 in 500 µL ABC) (n = 10) | |
| I | BCP (TCP/HA 80/20) 74-420 µm + ABGS (20 µg rhBMP6 in 500 µL ABC) (n = 10) | |

Figure 20:
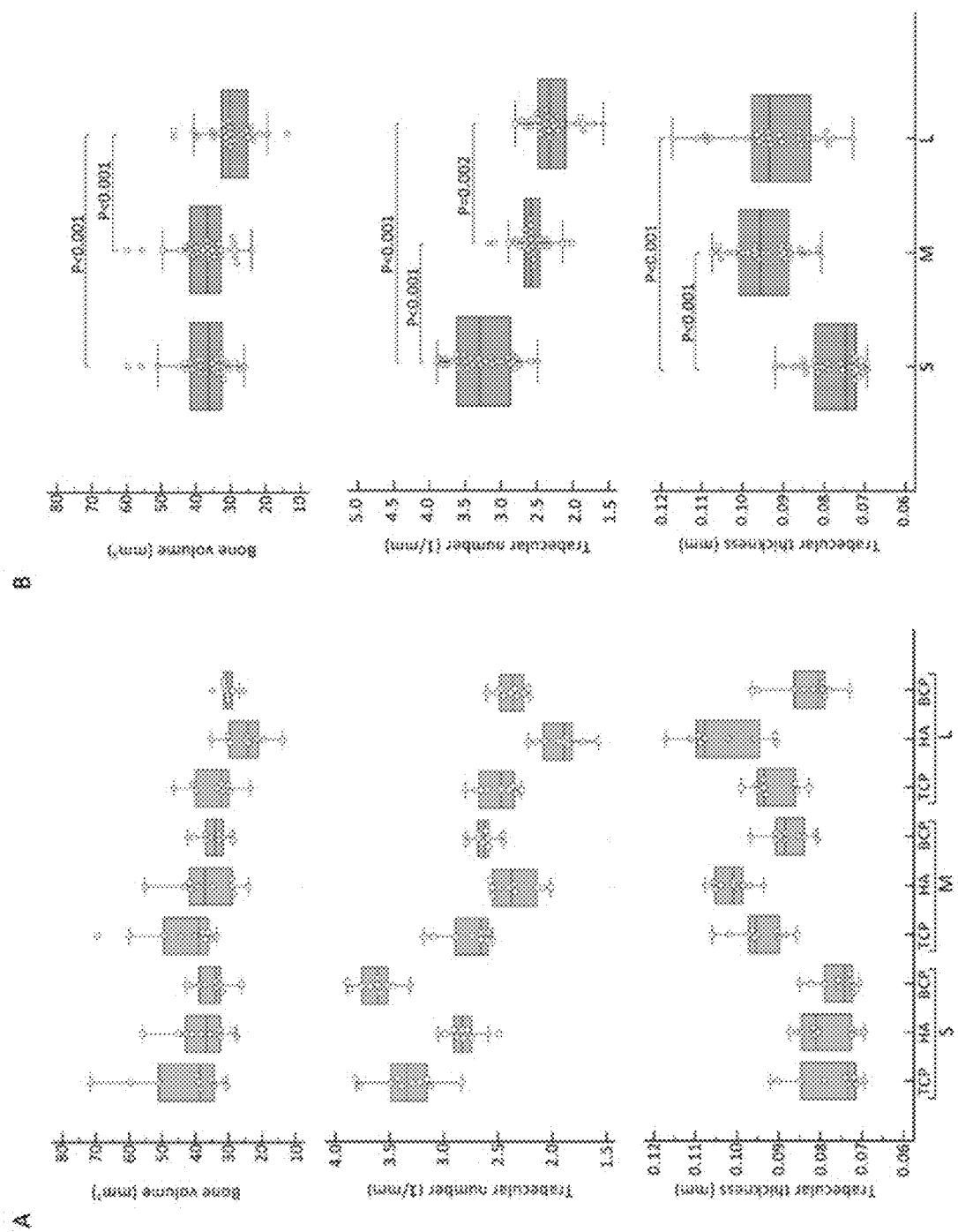
FIG. 20 shows MicroCT analyses of ABGS containing bioceramics with different particle size and chemical composition.
Figure 21:
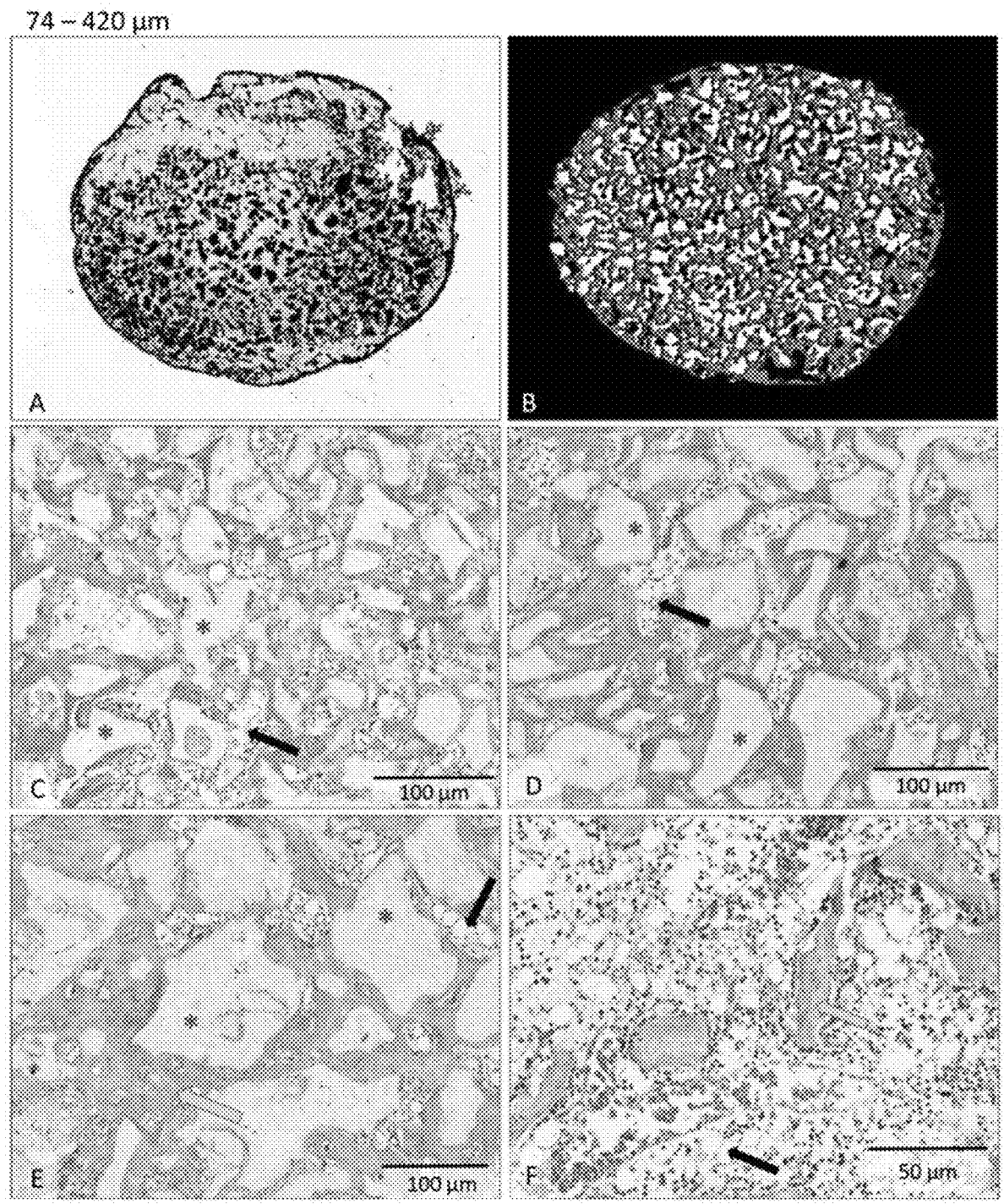
FIG. 21 illustrates Small size ceramic particles in range from 74 to 420 μm, where Panel (A) illustrates Whole histology section of BCS containing small particles (Von Kossa stain), Panel (B) illustrates Reconstructed MicroCT image showing newly formed bone (green) and CRM (white), and Panels (C, D, E, F) illustrate Modified Goldner's stained histology sections of BCS containing small ceramic particles of various chemical composition.

FIG. 20 shows MicroCT analyses of ABGS containing bioceramics with different particle size and chemical composition. Panel (A) illustrates Bone volume (mm3), trabecular number (1/mm) and trabecular thickness (mm) among experimental groups. Panel (B) illustrates Aforementioned bone parameters presented according to the particle size regardless of the chemical composition. S—small size particles (74-420 µm), M—medium size particles (500-1700 µm), L—large size particles (1000-4000 µm). Results are shown as median with interquartile range (IQR). Non-parametric Kruskal Wallis test was used with post hoc Mann Whitney U-test. n=10 per group FIG. 21 illustrates Small size ceramic particles in range from 74 to 420 µm. Panel (A) illustrates Whole histology section of BCS containing small particles (Von Kossa stain). Panel (B) illustrates Reconstructed MicroCT image showing newly formed bone (green) and CRM (white). Panels (C, D, E, F) illustrate Modified Goldner's stained histology sections of BCS containing small ceramic particles of various chemical composition. Red asterisks indicate ceramic particles. Yellow arrows indicate newly formed bone, while black arrows mark the bone marrow. Scale bars are indicated in lower right corners.

Figure 22:
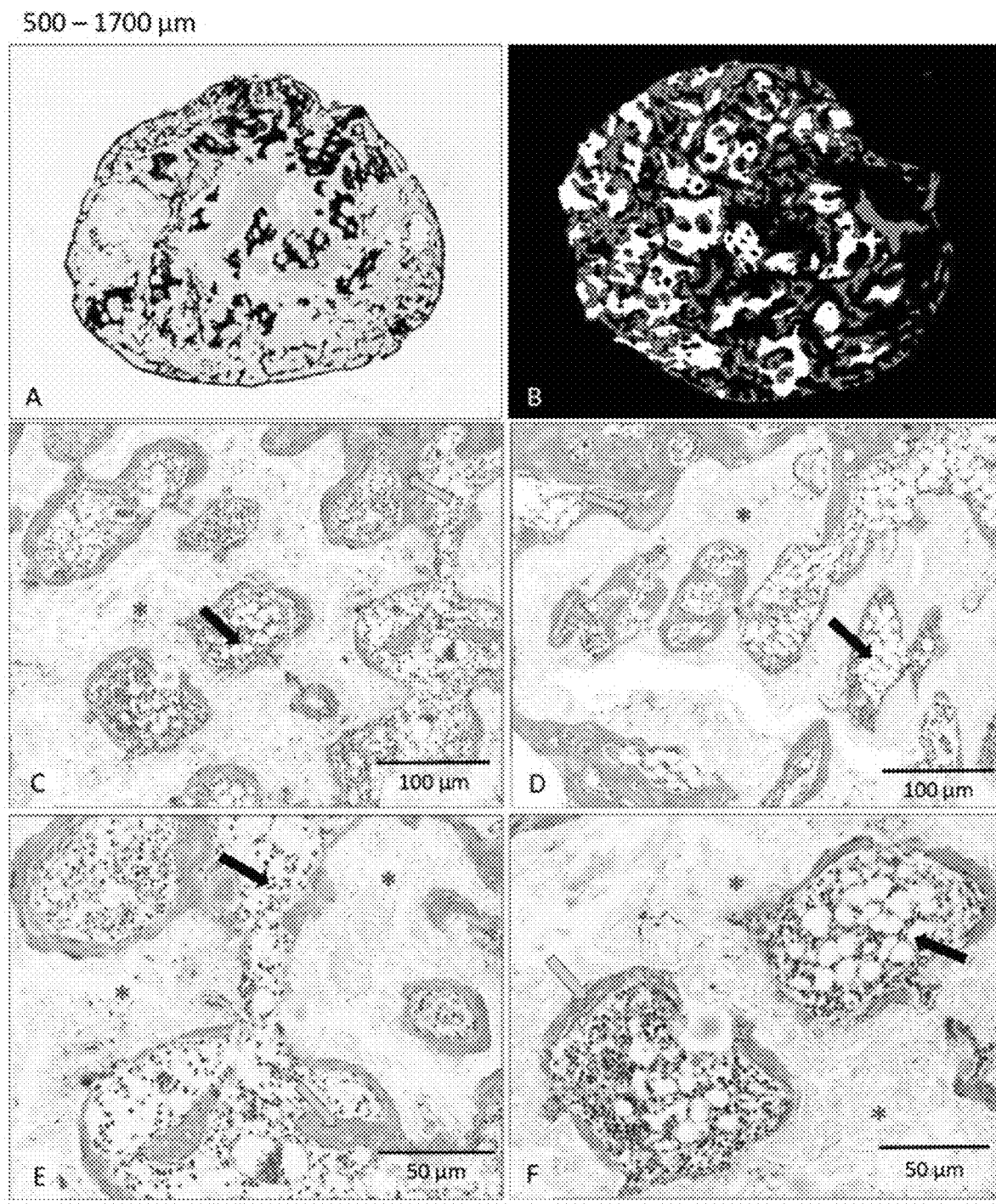
FIG. 22 illustrate Medium size ceramic particles in range from 500 to 1700 μm, where Panel (A) is Whole histology section of BCS containing medium particles (Von Kossa stain), Panel (B) is Reconstructed MicroCT image showed newly formed bone (green) and CRM (white), and Panels (C, D, E, F) are Modified Goldner's stained histology sections of BCS containing medium ceramic particles of a various chemical composition.

FIG. 22 illustrate Medium size ceramic particles in range from 500 to 1700 μm. Panel (A) is Whole histology section of BCS containing medium particles (Von Kossa stain). Panel (B) is Reconstructed MicroCT image showed newly formed bone (green) and CRM (white). Panels (C, D, E, F) are Modified Goldner's stained histology sections of BCS containing medium ceramic particles of a various chemical composition. Red asterisks indicate ceramic particles. Yellow arrows indicate newly formed bone, while black arrows mark the bone marrow. Scale bars are indicated in lower right corners.

Figure 23:
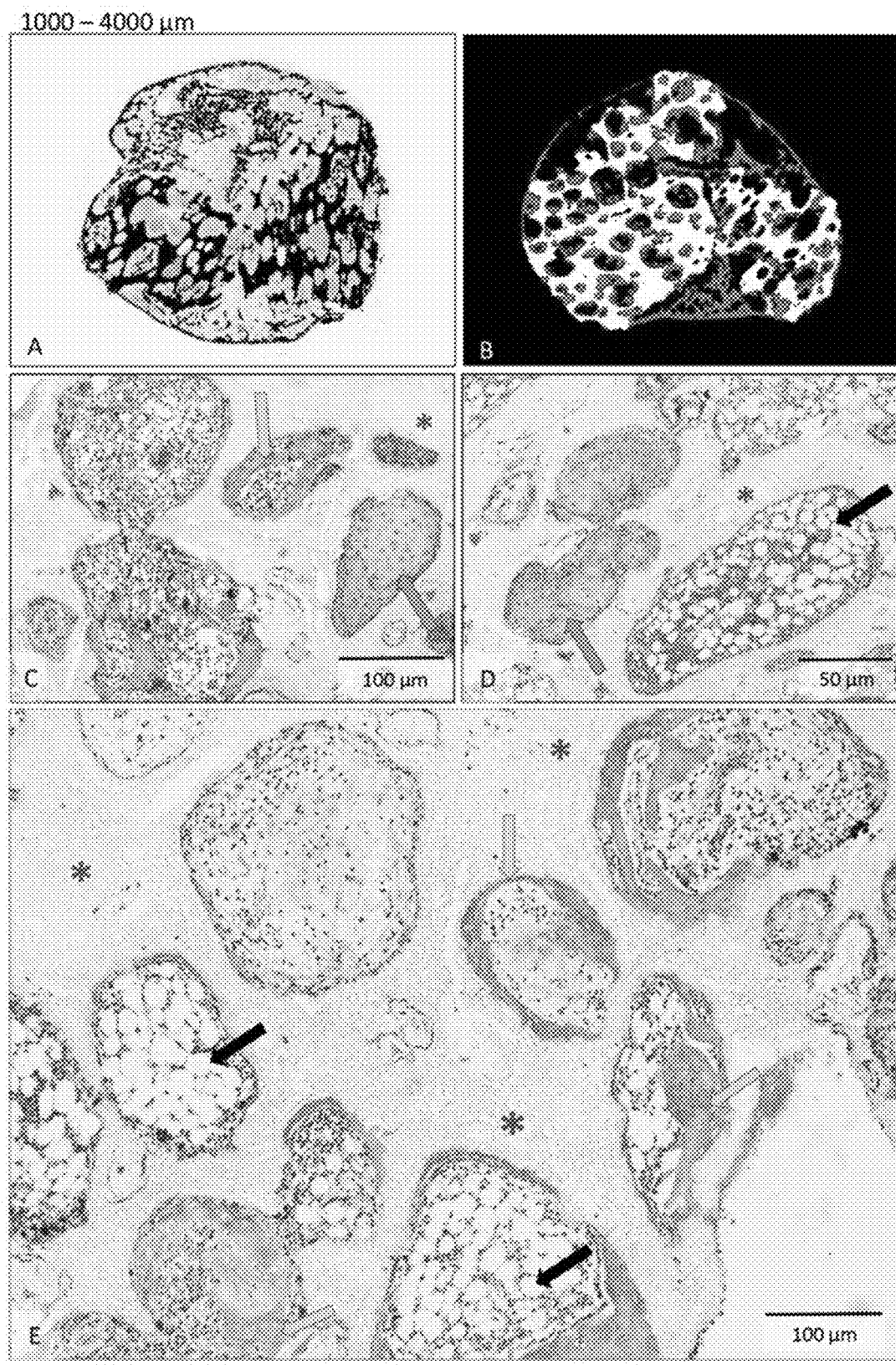
FIG. 23 illustrates Large size ceramic particles in range from 1000 to 4000 μm, where Panel (A) is Whole histology section of BCS containing large size particles (Von Kossa stain), Panel (B) is Reconstructed MicroCT image showed newly formed bone (green) and CRM (white), and Panels (C, D, E) are Modified Goldner's stained histology sections of BCS containing large ceramic particles of various chemical composition.

FIG. 23 illustrates Large size ceramic particles in range from 1000 to 4000 μm. Panel (A) is Whole histology section of BCS containing large size particles (Von Kossa stain). Panel (B) is Reconstructed MicroCT image showed newly formed bone (green) and CRM (white). Panels (C, D, E) are Modified Goldner's stained histology sections of BCS containing large ceramic particles of various chemical composition. Red asterisks indicate ceramic particles. Yellow arrows indicate newly formed bone, green arrows indicate endochondral ossification and black arrows show bone marrow. Scale bars are indicated in lower right corners.

Both MicroCT and histological analysis confirmed that the amount of newly formed bone was extensive in all tested formulation of osteoinductive device containing rhBMP6, autologous blood coagulum and bioceramic particles regardless of the size and chemical composition of bioceramic particles. However, significantly higher amount of newly formed bone was formed in ABGS implants containing small (74-420 μm) and medium (500-1700 μm) than large (1000-4000 μm) particles (FIG. 20). Moreover, size of the bioceramic particles determined the structural properties of newly formed bone-ceramic structure (BCS) which consisted of newly formed bone and bioceramic particles (FIGS. 21-23).

Implants containing smallest bioceramic particles (74-420 μm) consisted of two portions: one initially containing bioceramic particles and autologous blood coagulum and other initially containing only autologous blood coagulum. In portion containing bioceramic particles newly formed bone was very dense, present around and between particles (FIG. 21) while in portion without bioceramic particles newly formed bone consisted of trabeculae and bone marrow between them (FIG. 21F). In implants containing large (1000-4000 μm) and medium (500-1500 μm) bioceramic particles, cortical bone was present in the peripheral parts of the implants. Newly formed bone was present between the particles and inside the pores (FIGS. 22-23). Bone marrow containing both hematopoetic cells and adipocytes was present between trabeculae. On the other hand, there was no difference in the histological features of bone-ceramic structures with different chemical composition of particles but the same size.

To sum up, the architecture and the amount of newly formed bone was influenced by the particle size and not chemical composition of the bioceramic particles.

Example 7—OPS-20191107/Subcutaneous Implant Assay/Rats

Example 7 describes a Rat subcutaneous implant assay which was conducted to rats to compare the amount of newly induced bone between autologous bone graft substitute (ABGS) formulation which rhBMP6 differ in method of rhBMP6 application (rhBMP6 added in blood and mixed with bioceramics or prelyophilized on bioceramics prior to mixing with blood).

Materials & Methods

In this example 18 Sprague Dawley rats (lat. *Rattus norvegicus*, male and female, 6-8 weeks old) were used, which were assigned to 6 experimental groups according to the experimental design presented in Table 12. Blood samples were collected into tubes without an anticoagulant substance in a volume of 500 μL. In groups A, C and E rhBMP6 (20 μg) was put in blood and mixed with bioceramics. In groups B, D and F rhBMP6 (20 μg) was prelyophilized on bioceramics and mixed with blood. A vertical incision (1 cm) was made under sterile conditions in the skin over the thoracic region, and the pockets were prepared by a blunt dissection on both sides of the incision (in the left and right axillary region). ABGS implants were implanted deep into the pockets (two implants per animal), and the incision was closed with a surgical clip. After 21 day animals were euthanized and implants were removed for further analyses.

Results

Figure 24:
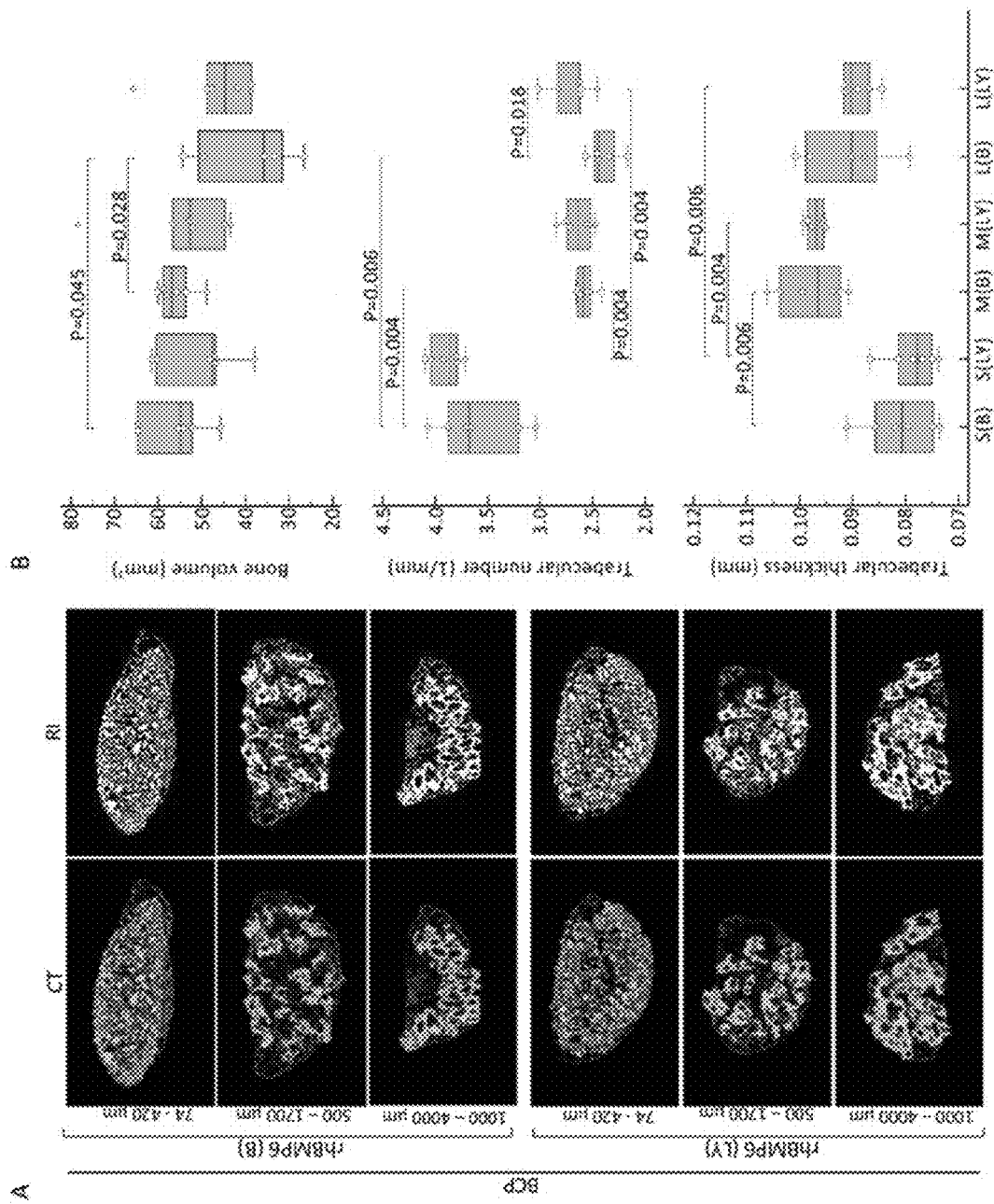
FIG. 24, Panel (A) are MicroCT images of ABGS containing various particle size of BCP ceramics with different methods of rhBMP6 application-directly into the blood (B) or pre-lyophilized (LY), and Panel (B) is Bone volume ($mm^3$), trabecular number (1/mm) and trabecular thickness (mm) among experimental groups: S(B) (74-420 μm, in blood); S(LY) (74-420 μm, lyophilized); M(B) (500-1700 μm, in blood); M(LY) (500-1700 μm, lyophilized); L(B) (1000-4000 μm, in blood); L(LY) (1000-4000 μm, lyophilized) on day 21 shown as median with interquartile range (IQR).

Results are presented in Table 12 and FIG. 24.

TABLE 12

Example 7—OPS-20191107 Groups and results

| Group | Group description | Result |
|---|---|---|
| A | BCP (TCP/HA 80/20) 74-420 μm + ABGS (20 μg rhBMP6 in 500 μL ABC) (n = 6) | Newly formed bone was induced in all (36/36) ABGS implants. |
| B | BCP (TCP/HA 80/20) 74-420 μm + 20 μg rhBMP6 (lyo) + 500 μL ABC (n = 6) | Two tested methods of rhBMP6 application in ABGS implants (rhBMP6 added directly to blood or rhBMP6 prelyophilized on bioceramic particles) had equivalent outcome regardless of the used particle size of bioceramics. |
| C | BCP (TCP/HA 80/20) 1000-1700 μm + ABGS (20 μg rhBMP6 in 500 μL ABC) (n = 6) | |
| D | BCP (TCP/HA 80/20) 1000-1700 μm +20 μg rhBMP6 (lyo) + 500 μL ABC (n = 6) | |
| E | BCP (TCP/HA 80/20) 1000-4000 μm + ABGS (20 μg rhBMP6 in 500 μL ABC) (n = 6) | |
| F | BCP (TCP/HA 80/20) 1000-4000 μm +20 μg rhBMP6 (lyo) + 500 μL ABC (n = 6) | |

FIG. 24, Panel (A) are MicroCT images of ABGS containing various particle size of BCP ceramics with different methods of rhBMP6 application—directly into the blood (B) or pre-lyophilized (LY). Reconstructed images (RI) of ABGS showing newly formed bone (green) and ceramics (white). Panel (B) is Bone volume (mm3), trabecular number (1/mm) and trabecular thickness (mm) among experimental groups: S(B) (74-420 μm, in blood); S(LY) (74-420 μm, lyophilized); M(B) (500-1700 μm, in blood); M(LY) (500-1700 μm, lyophilized); L(B) (1000-4000 μm, in blood); L(LY) (1000-4000 μm, lyophilized) on day 21 shown as median with interquartile range (IQR). Nonparametric Kruskal Wallis test was used with post hoc Mann Whitney U-test. P values (P<0.05) were indicated in the Figure; n=6 per group.

At the end of the follow-up period (21 days) all ABGS implants induced formation of extensive amount of bone which along with bioceramic particles formed bone-ceramic structure (BCS) (FIG. 24 Panel A). MicroCT analyses revealed that there was no significant difference neither in the amount of newly formed bone nor BCS structure among two tested methods of rhBMP6 application (FIG. 24 Panel B).

Example 8—OPS-20200201/Subcutaneous Implant Assay/Rats

Example 8 describes a Rat subcutaneous implant assay which was conducted to compare the amount of ectopic bone induced by various ABGS formulations containing different doses (5, 20 and 50 μg) of rhBMP2 and rhBMP6 in autologous blood coagulum (ABC) mixed with bioceramic particles (BCP 1000-1700 μm).

Materials & Methods

In this example 18 Sprague Dawley rats (lat. *Rattus norvegicus*, male and female, 6-8 weeks old) were used which were assigned to 6 experimental groups according to the experimental design presented in Table 13.

Blood samples were collected into tubes without an anticoagulant substance in a volume of 500 μL. rhBMP2 or rhBMP6 in doses defined in Table 13 (5, 20 or 50 μg) was put in blood and mixed with bioceramics. A vertical incision (1 cm) was made under sterile conditions in the skin over the thoracic region, and the pockets were prepared by a blunt dissection on both sides of the incision (in the left and right axillary region). ABGS implants were implanted deep into the pockets (two implants per animal), and the incision was closed with a surgical clip. After 14 days animals were euthanized and implants were removed for further analyses.

Results

Figure 25:
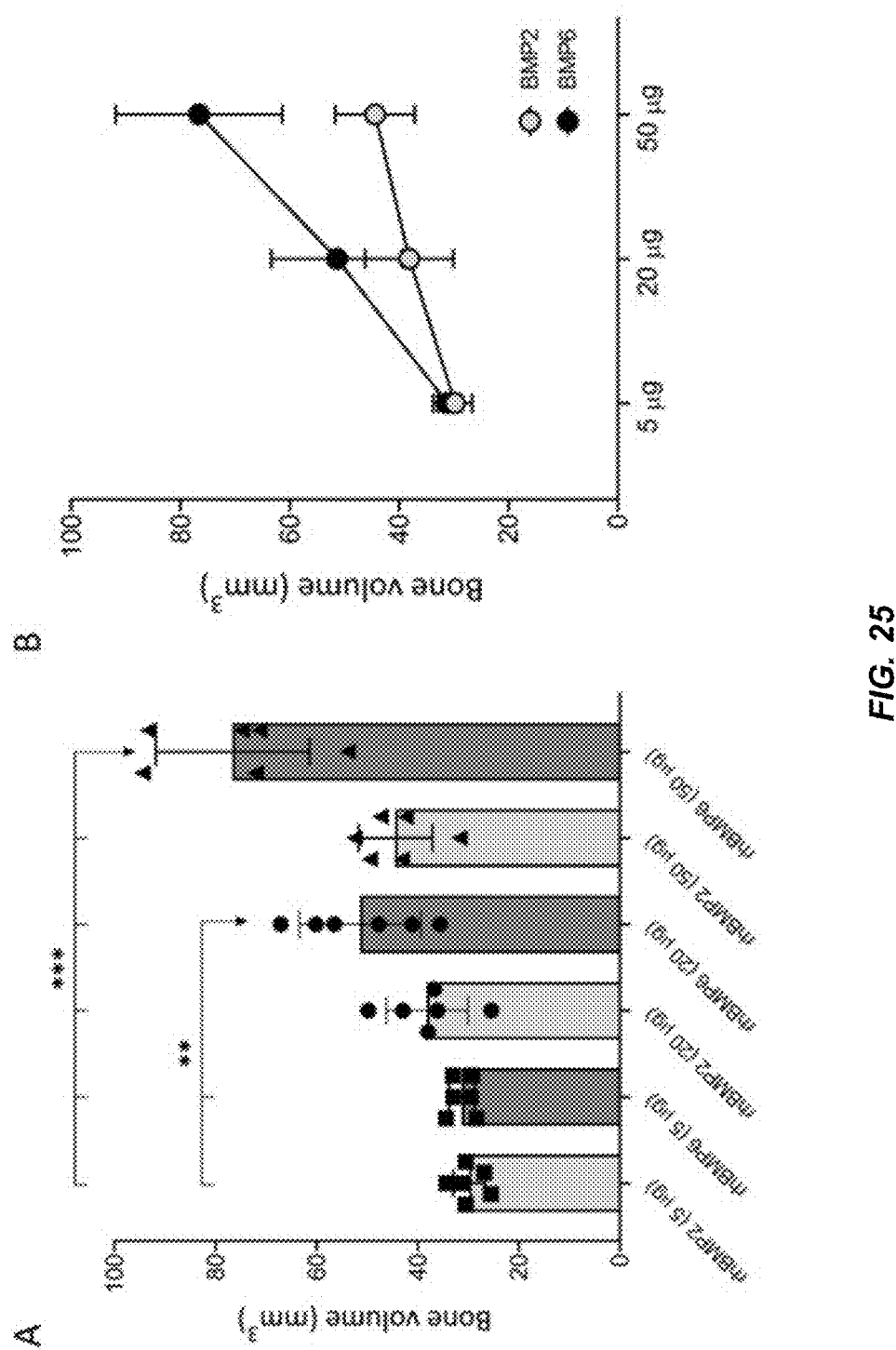
FIG. 25 Panels A and B illustrate Bone volume ($mm^3$) among experimental groups.

Results are presented in Table 13 and FIG. 25.

TABLE 13

Example 8—OPS-20200201 Groups and results

| Group | Group description | Result |
|---|---|---|
| A | BCP (TCP/HA 80/20) 1000-1700 μm + ABGS (5 μg BMP2 in 500 μL ABC) (n = 6) | Newly formed bone was induced in all (36/36) ABGS implants. |
| B | BCP (TCP/HA 80/20) 1000-1700 μm +ABGS (20 pg BMP2 in 500 μL ABC) (n = 6) | ABGS implants containing both rhBMP6 or rhBMP2 induced formation of extensive amount of newly formed bone which along the bioceramic particles formed bone-ceramic structure (BCS). However, when the highest dose (50 +82 g) was applied rhBMP6 was superior to rhBMP2 |
| C | BCP (TCP/HA 80/20) 1000-1700 μm + ABGS (50 μg BMP2 in 500 μL ABC) (n = 6) | |
| D | BCP (TCP/HA 80/20) 1000-1700 μm + ABGS (5 μg BMP6 in 500 μL ABC) (n = 6) | |
| E | BCP (TCP/HA 80/20) 1000-1700 μm +ABGS (20 μg BMP6 in 500 μL ABC) (n = 6) | |
| F | BCP (TCP/HA 80/20) 1000-1700 μm + ABGS (50 μg BMP6 in 500 μL ABC) (n = 6) | |

FIG. 25 Panels A and B illustrate Bone volume (mm3) among experimental groups. The amount of newly formed bone was highest in ABGS implants containing 20 and 50 μg of rhBMP6.

In this example it is demonstrated that ABGS containing both rhBMP6 or rhBMP2 in autologous blood coagulum with bioceramic particles induce formation of bone which along with bioceramic particles forms bone-ceramic structure (BCS). However, bone formation was dose dependent and formulations containing higher doses (20 and 50 μg) of both rhBMP2 and rhBMP6 induced significantly larger amount of bone than formulations containing lower dose (5 μg) (FIG. 25). Importantly, when the highest dose (50 μg) was applied rhBMP6 was superior to rhBMP2.

Example 9—OPS-20200703/Biomechanical Testing/Rabbits

Example 9 was conducted to determine biomechanical properties (stiffness, elasticity, work-to-break) of autologous bone graft substitute (ABGS) implants containing autologous blood coagulum (ABC) and bioceramics (in the form of particles or blocks) as compression resistant matrix and compare it with implants containing only ABC.

Materials & Methods

Blood was withdrawn from ear marginal vein into tubes without any anticoagulant substance. Bioceramics were placed in syringes (5 mL) and following blood withdrawal, blood (2.5 mL) was mixed with bioceramic particles or blocks.

Biomechanical properties of the implants (stiffness, elasticity and work) were evaluated performing cut test. Implants were cut in one point through the central part of implants.

Results

Figure 26:
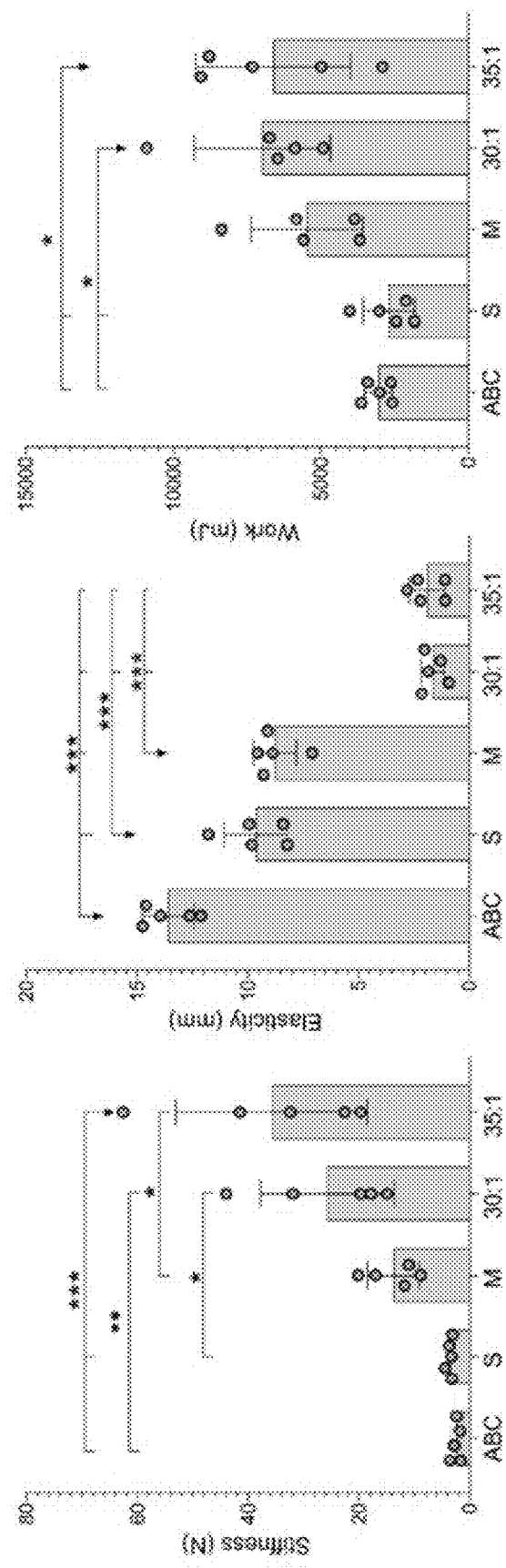
FIG. 26 illustrate Biomechanical properties (stiffness, elasticity, and work) of autologous bone graft substitute (ABGS) with cylindrical bioceramic block compared with ABGS with bioceramic particles (small, 74-420 μm (S) and medium, 500-1700 μm (M)) or without bioceramic particles (autologous blood coagulum—ABC).

Results are presented in Table 14 and FIG. 26.

TABLE 14

Example 9—OPS-20200703 Groups and results

| Group | Group description | Result |
|---|---|---|
| A | BCP (TCP/HA 40/60) 74-420 μm + 2.5 mL ABC (n = 5) | ABGS implants containing bioceramic blocks as CRM have higher stiffness and work but lower elasticity compared to implants with bioceramic particles as CRM orwithout CRM (ABC alone) |
| B | BCP (TCP/HA 40/60) 500-1700 μm + 2.5 mL ABC (n = 5) | |
| C | BCP (TCP/HA 80/20) macroporous blocks 30:1 + 2.5 mL ABC (n = 5) | |
| D | BCP (TCP/HA 80/20) macroporous blocks 35:1 + 2.5 mL ABC (n = 5) | |
| E | 2.5 mL ABC (n = 5) | |

FIG. 26 illustrate Biomechanical properties (stiffness, elasticity, and work) of autologous bone graft substitute (ABGS) with cylindrical bioceramic blocks (cylinders with 30:1 and 35:1 S/F ratio (Cyl 30:1, Cyl 35:1, respectively) compared with ABGS with bioceramic particles (small, 74-420 μm (S) and medium, 500-1700 μm (M)) or without bioceramic particles (autologous blood coagulum—ABC). All values were determined using the cut test and expressed as mean±SD as indicated. One-way analysis of variance with Tukey's multiple comparisons test was performed. Arrows at lines above graph bars indicate the experimental group statistically compared with other experimental groups marked by a vertical line. P values are marked with asterisk indicating *P≤0.05, P≤0.01, *P≤0.001.

Stiffness and work were significantly higher in ABGS formulations containing bioceramic blocks as a CRM compared to ABGS with bioceramic particles or ABC alone (FIG. 26). There was no significant difference neither in stiffness nor work-to-break between tested bioceramic blocks.

Elasticity was significantly lower in groups containing bioceramic blocks than in groups containing particles or without CRM (FIG. 26).

Example 10—OPS-20190321/Posterolateral Spinal Fusion/Rabbits

Example 10 was conducted to investigate ectopic bone formation and osseointegration in posterolateral spinal fusion (PLF) model in New Zealand white rabbits using autologous bone graft substitute (ABGS) containing rhBMP6 in autologous blood coagulum (ABC) with bioceramic particles and blocks as compression resistant matrix (CRM). In this example 2 New Zealand White Rabbits (lat. *Oryctolagus cuniculus*, male, 3-5 kg) were used, which were assigned to 4 experimental groups according to the experimental design presented in Table 15.

Materials & Methods

Blood samples were collected from rabbit ear marginal vein into tubes without an anticoagulant substance in a volume of 2.5 mL. rhBMP6 (125 µg) was put in blood and mixed with bioceramics. After blood and bioceramics were mixed, device was rotated until formation of coagulum to achieve uniform distribution of bioceramic particles in blood coagulum. Spaces between transverse processes of lumbar spine were exposed and following bone decortication implants were implanted bilateraly between transverse processes of lumbar vertebrae L5-L6. All animals were euthanized on day 60 after the date of surgery.

Results

Figure 27:
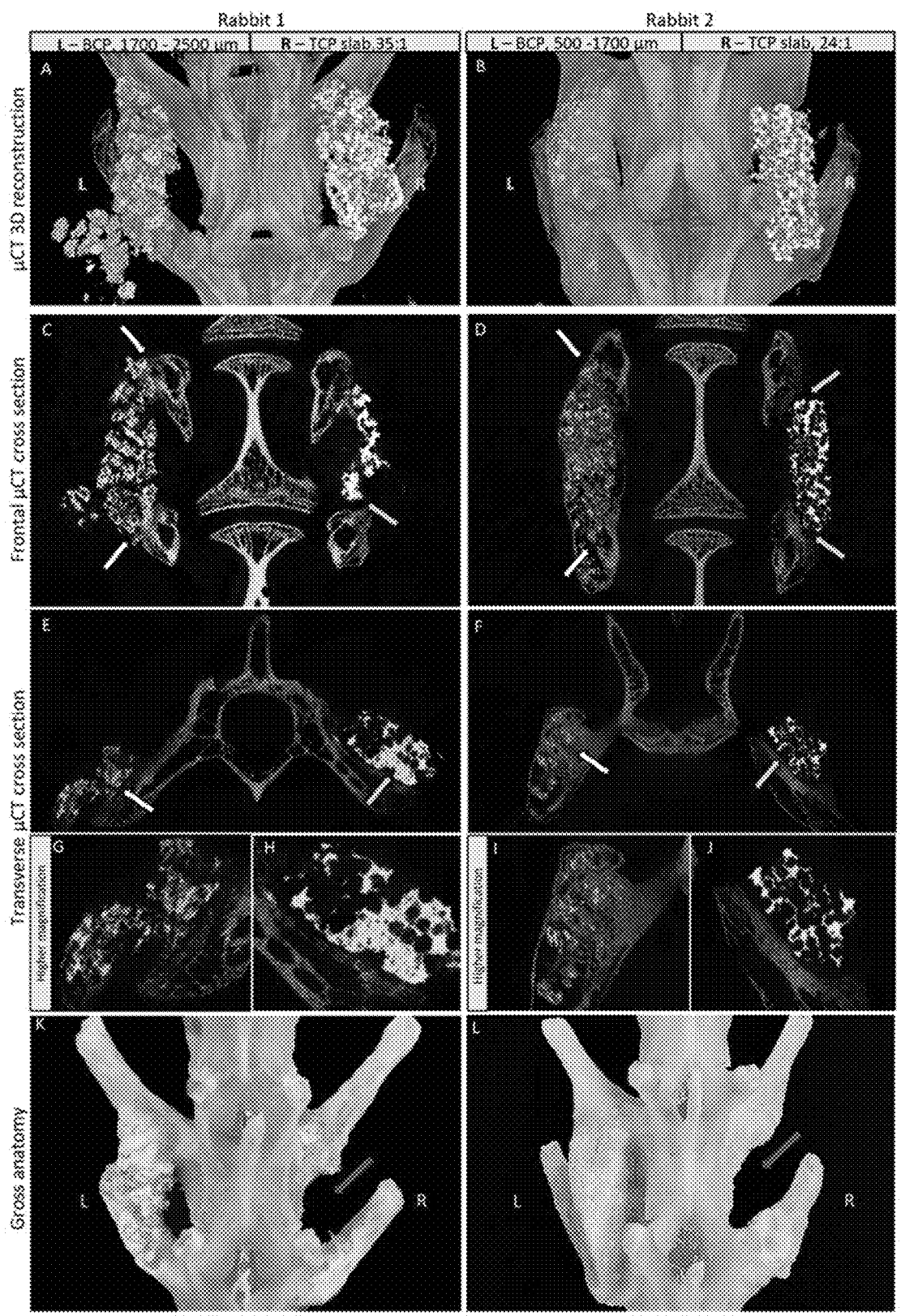
FIG. 27 illustrates a rabbit spinal fusion.

Results are presented in Table 15 and FIG. 27.

TABLE 15

Example 10—OPS-20190321 Groups and results

| Group | Group description | Result |
|---|---|---|
| A | BCP (TCP/HA 80/20) 1700-2500 µm + ABGS (125 µg rhBMP6 in 2.5 mL ABC) (n = 1) | Successful rebridgment and moderate osseointegration of newly formed bone with transverse processes |
| B | BCP (TCP/HA 80/20) 500-1700 µm + ABGS (125 µg rhBMP6 in 2.5 mL ABC) (n = 1) | Successful rebridgment and osseointegration of newly formed bone with transverse processes |
| C | TCP macroporous block (35:1) + ABGS (125 µg rhBMP6 in 2.5 mL ABC) (n = 1) | Unsuccessful fusion |
| D | TCP macroporous block (24:1) + ABGS (125 µg rhBMP6 in 2.5 mL ABC) (n = 1) | Unsuccessful fusion |

FIG. 27 illustrates the rabbit spinal fusion. The rabbit spinal fusion (L5-L6) was conducted with ABGS containing various types of CRM—different size ceramics particles (BCP) and slabs (TCP) with different porosity: Rabbit 1 (L=BCP, 1700-2500 µm, R=TCP slab, porosity—35:1); Rabbit 2 (L=BCP, 500-1700 µm, R=TCP slab, porosity—24:1). (A, B) µCT 3D reconstruction indicated a successful fusion on the left sides, while on the right sides the fusion of ceramic slabs failed. (C, D) Frontal µCT cross sections showing successful (white arrow) and failed (yellow arrow) integration of new bone with transverse processes. (E, F) Transverse µCT cross sections presenting successful (white arrow) and failed (yellow arrow) integration. (G, H, I, J) Successful and failed integration at higher magnification on transverse µCT cross sections. (K,L) Gross anatomy of the same specimen. During the maceration, ceramics slabs on the right side detached (red arrows) from the transverse processes since they were not integrated. L—left side; R—right side.

In this example, rhBMP6 induced bone in all tested formulations containing ABC and bioceramics. However, the degree of osseointegration of the newly formed bone with the transverse processes was different. In the implant with BCP 500-1700 µm particles the osseointegration was complete, in the implant containing BCP 1700-2500 µm particles it was moderate, while in implants containing TCP slabs the osseointegration did not occur (FIG. 27). Moreover, the volume of newly formed bone was highest when 500-1700 µm particles were used. Therefore, particles of 500-1700 µm size were used in further experiments.

Example 11—OPS-20190604/Posterolateral Spinal Fusion/Rabbit

Example 11 was conducted to investigate ectopic bone formation and osseointegration in rabbit posterolateral spinal fusion (PLF) model using autologous bone graft substitute (ABGS) containing rhBMP6, autologous blood coagulum (ABC) and bioceramics as compression resistant matrix (CRM). This experiment compared two methods of rhBMP6 application in the implant (added directly in blood vs lyophilization on bioceramics) as well as two different compression resistant matrices (biphasic bioceramics vs tricalcium phosphate bioceramics). In this example 12 New Zealand White Rabbits (lat. *Oryctolagus cuniculus*, male, 3-5 kg) were used, which were assigned to 4 experimental groups according to the experimental design presented in Table 16.

Materials & Methods

Blood samples were collected from rabbit ear marginal vein into tubes without an anticoagulant substance in a volume of 2.5 mL. In groups A and C rhBMP6 (125 µg) was put in blood and mixed with bioceramics while in groups B and D rhBMP6 (125 µg) was lyophilized on bioceramics and then mixed with blood. After blood and bioceramics were mixed, device was rotated until formation of coagulum to achieve uniform distribution of bioceramic particles in blood coagulum. Spaces between transverse processes of lumbar spine were exposed and following bone decortication implants were implanted bilateraly between transverse processes of lumbar vertebrae L5-L6. All animals were euthanized on day 50 after the date of surgery.

Results

Figure 28:
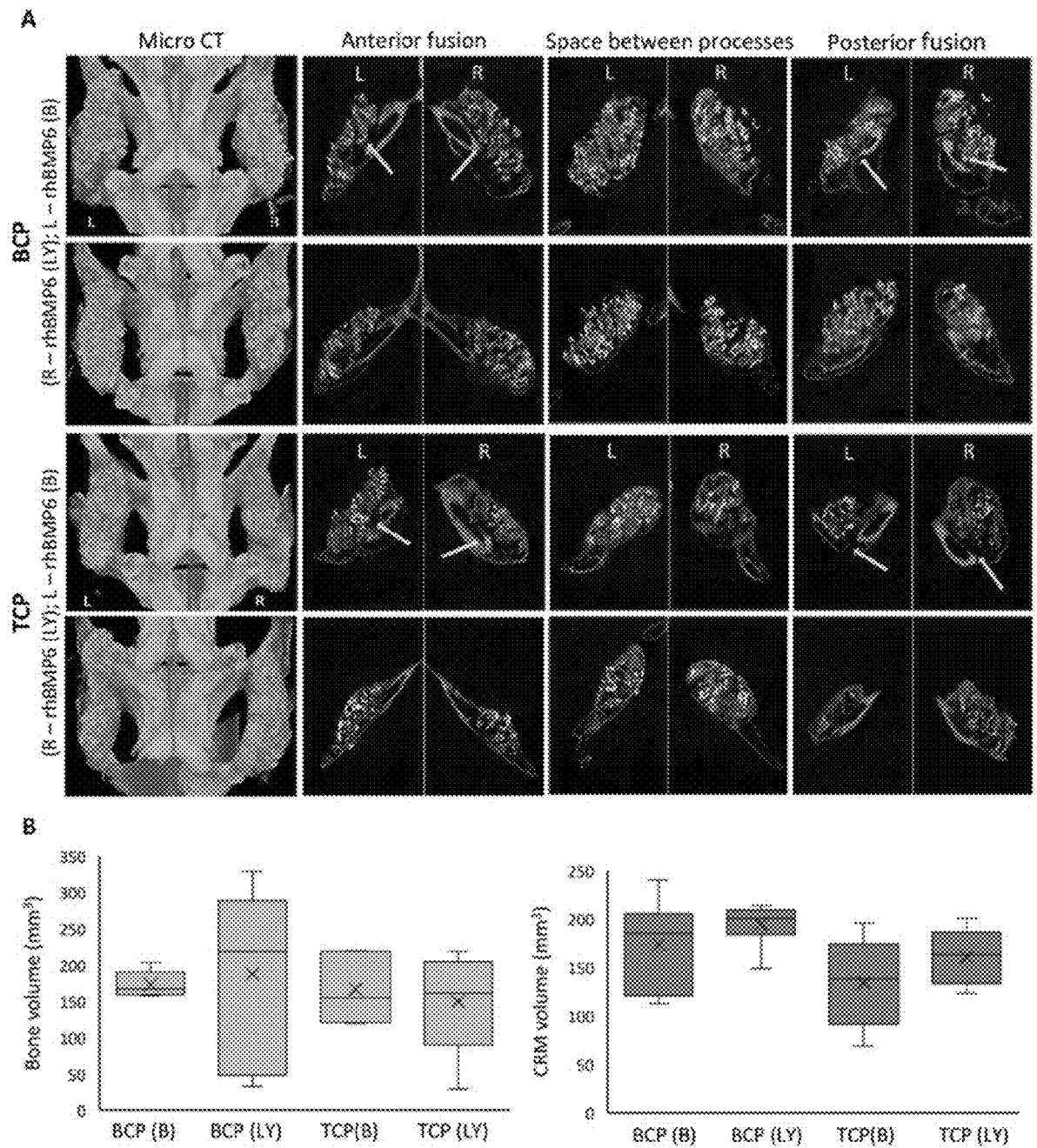
FIG. 28 illustrates MicroCT images, bone volume and CRM volume.
Figure 29:
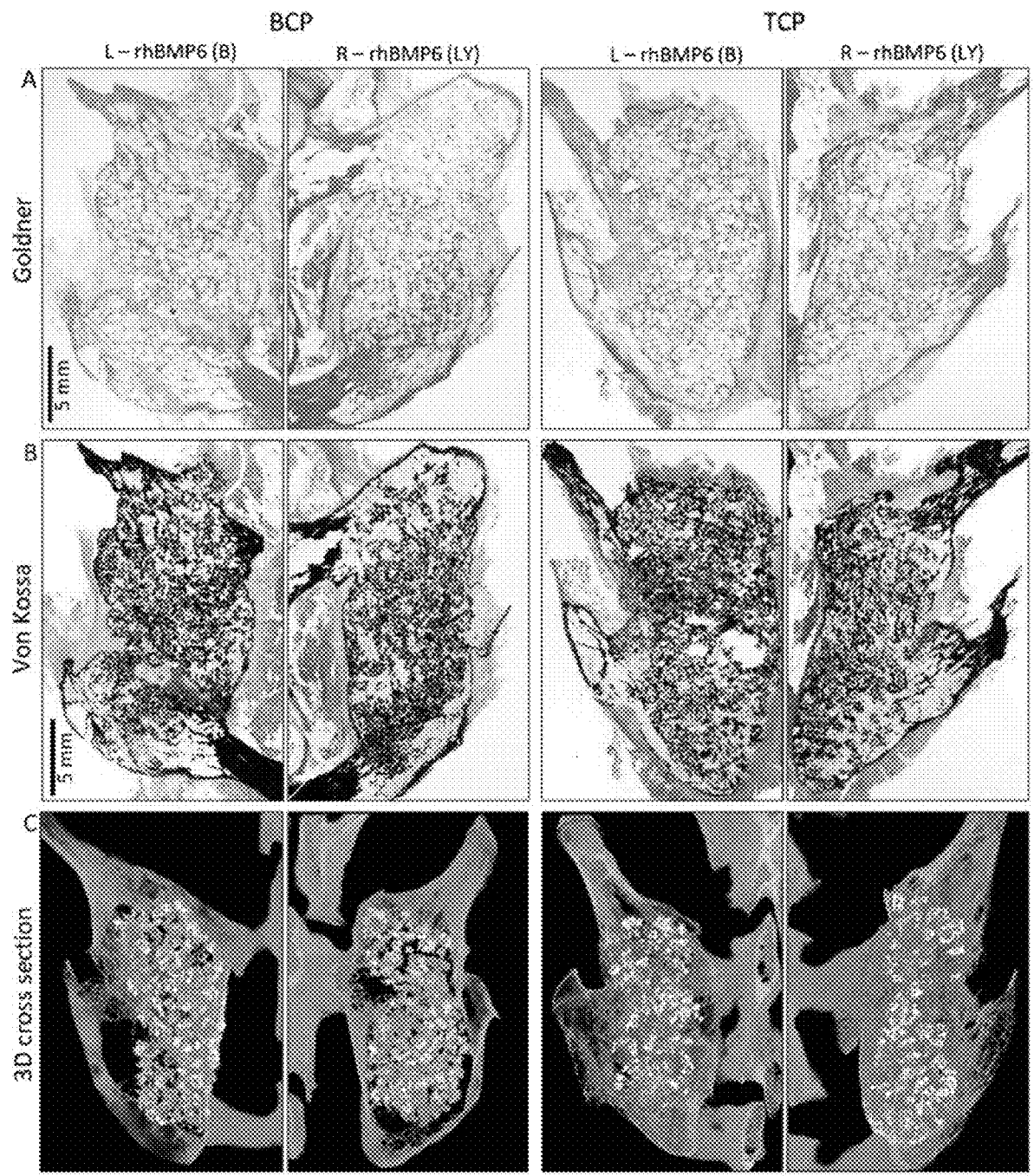
FIG. 29 Panels (A, B) show Histology sections stained by Goldner and Von Kossa staining, respectively of BCP and TCP ceramics.

Results are presented in Table 16 and FIGS. 28 and 29.

TABLE 16

Example 11—OPS-20190604 Groups and results

| Group | Group description | Result |
|---|---|---|
| A | BCP (TCP/HA 80/20) 500-1700 µm + ABGS (125 µg rhBMP6 in 2.5 mL ABC) (n = 6) | Successful rebridgment and osseointegration of newly formed bone with transverse processes was observed in 5/6 animals (83%) |
| B | BCP (TCP/HA 80/20) 500-1700 µm + 125 pg BMP6 (lyo) + 2.5 mL ABC (n = 6) | Successful rebridgment and osseointegration of newly formed bone with transverse processes was observed in 6/6 animals (100%) |
| C | TCP 500-1700 µm + ABGS (125 µg rhBMP6 in 2.5 mL ABC) (n = 6) | Successful rebridgment and osseointegration of newly formed bone with transverse processes was observed in 5/5 animals (100%) |

TABLE 16-continued

| | Example 11—OPS-20190604 Groups and results | |
|---|---|---|
| Group | Group description | Result |
| D | TCP 500-1700 μm + 125 μg BMP6 (lyo) + 2.5 mL ABC (n = 6) | Successful rebridgment and osseointegration of newly formed bone with transverse processes was observed in 4/5 animals (80%) |

FIG. 28 Panel (A) is MicroCT 3D reconstruction of PLF in rabbits showed successful integration with the transverse processes. MicroCT cross sections through anterior transverse process, space between transverse processes and posterior transverse process of rabbits. L=left side (rhBMP6 applied directly in autologus blood); R=right side (rhBMP6 lyophilized on ceramics particles); yellow arrows point at fusion site between newly formed bone and the transverse process. Panel (B) shows Bone volume and CRM volume (mm3) among experimental groups on day 50. Results are shown as median with interquartile range (IQR). Non-parametric Kruskal Wallis test was used with post hoc Mann Whitney U-test. B-rhBMP6 applied directly in autologus blood; LY-rhBMP6 lyophilized on ceramics particles. L—left side; R—right side.

FIG. 29 Panels (A, B) show Histology sections stained by Goldner and Von Kossa staining, respectively of BCP and TCP ceramics. On the left (L) side rhBMP6 was added in blood (B), while on the right side (R) rhBMP6 was lyophilized (LY). Panel (C) shows 3D cross sections of new ectopic bone fused with adjacent transverse processes among different experimental groups. Scale bars are indicated in the left corner of the histology images.

Newly formed bone and successful osseointegration with transverse processes was observed in all experimental groups (FIGS. 28-29). Successful spinal fusion between adjacent transverse processes was confirmed by both radiological methods (microCT sections, 3D reconstruction and analysis; x-ray images) and palpatory test of mobility of fused transverse processes. Total fusion success rate was 90.9% and the same result was obtained by both analysis of spinal fusion on microCT sections (FIG. 28 Panel A) and by palpatory mobility testing.

MicroCT analyses revealed that extensive amount of newly formed bone (bone volume) was present in all experimental groups and that there was no significant difference among experimental groups regardless used type of bioceramics (biphasic bioceramics or tricalcium phosphate bioceramics) or the method of rhBMP6 application in implant (rhBMP6 added directly in blood and then mixed with bioceramics or rhBMP6 lyophilized on bioceramics and then mixed with blood) (FIG. 28 Panel B). Therefore, all tested formulation achieved successful posterolateral spinal fusion in rabbits and might be tested in further rabbit and sheep experiments.

Example 12—OPS-20191030/Posterolateral Spinal Fusion/Rabbit

Example 12 was conducted to investigate spinal fusion outcome 14 weeks following implantation of ABGS (rhBMP6 in autologous blood coagulum with bioceramics) in rabbit posterolateral spinal fusion (PLF) model. This experiment compared two different types of bioceramics (tricalcium phosphate and biphasic bioceramics) as well as two different rhBMP6 doses (125 and 250 μg). In this example 8 New Zealand White Rabbits (lat. *Oryctolagus cuniculus*, male, 3-5 kg) were used, which were assigned to 5 experimental groups according to the experimental design listed below and presented in Table 17.

Materials & Methods

Blood samples were collected from rabbit ear marginal vein into tubes without an anticoagulant substance in a volume of 2.5 mL. In all groups rhBMP6 (125 or 250 μg) was put in blood and mixed with bioceramics. After blood and bioceramics were mixed, device was rotated until blood coagulation to achieve uniform distribution of bioceramic particles in blood coagulum. Spaces between transverse processes of lumbar spine were exposed and following bone decortication implants were implanted bilaterally between transverse processes of lumbar vertebrae L5-L6.

Results

Figure 30:
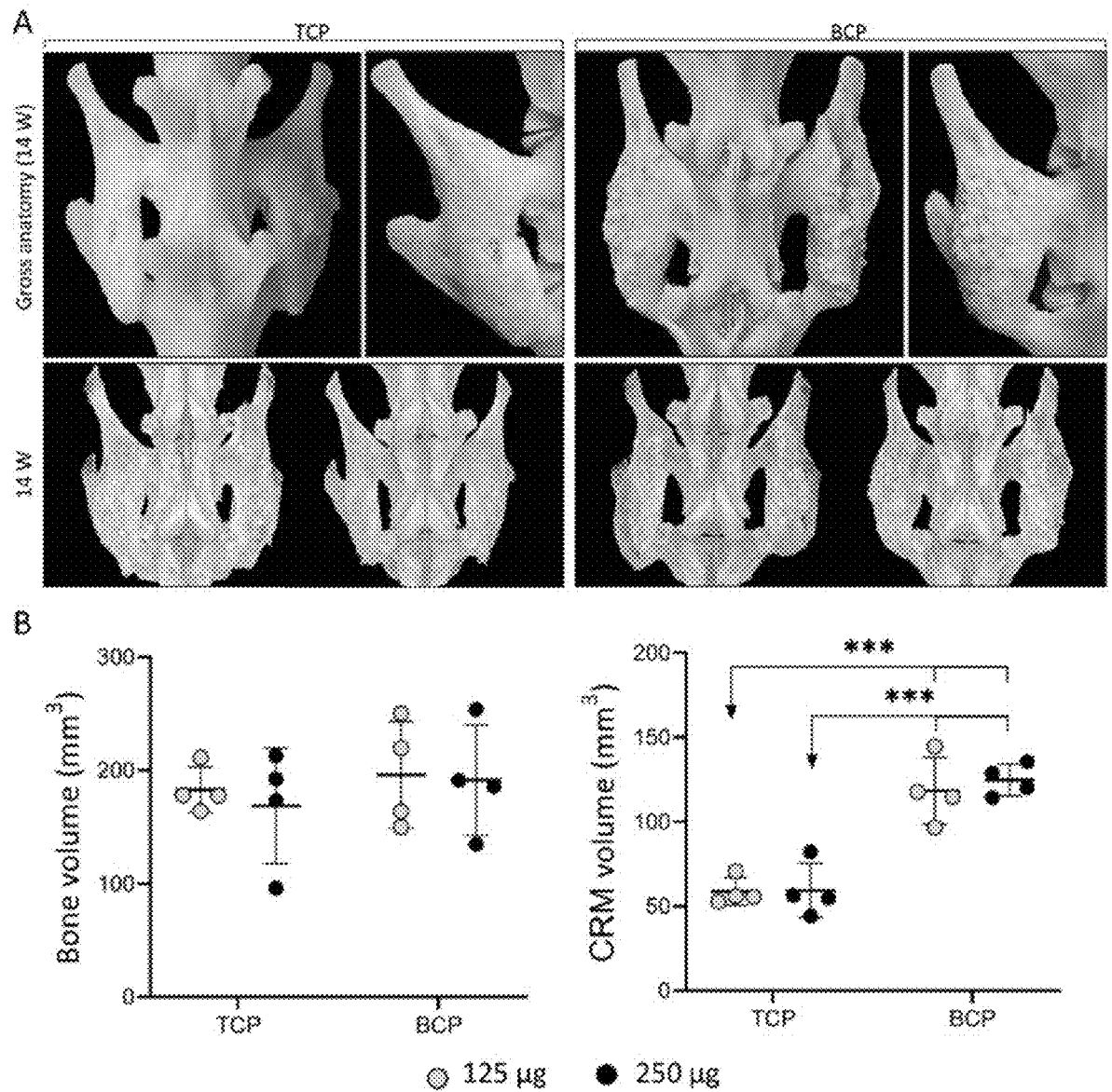
FIG. 30 Panel (A) shows Gross anatomy and MicroCT 3D reconstruction of fusion mass between transverse processes and Panel (B) shows Bone volume and CRM volume in BCS induced by ABGS containing TCP and BCP ceramic particles 14 weeks following ABGS implantation.

Results are presented in Table 17 and FIG. 30.

TABLE 17

| | Example 12—OPS-20191030 Groups and results | |
|---|---|---|
| Group | Group description | Result |
| A | TCP 500-1700 μm + ABGS (125 μg rhBMP6 in 2.5 mL ABC) (n = 4) | Successful rebridgment and osseointegration of newly formed bone with transverse processes was observed in 4/4 animals (100%) |
| B | TCP 500-1700 μm + ABGS (250 μg rhBMP6 in 2.5 mL ABC) (n = 4) | Successful rebridgment and osseointegration of newly formed bone with transverse processes was observed in 4/4 animals (100%) |
| C | BCP (TCP/HA 80/20) 1000-1700 μm + ABGS (125 μg rhBMP6 in 2.5 mL ABC) (n = 4) | Successful rebridgment and osseointegration of newly formed bone with transverse processes was observed in 4/4 animals (100%) |
| D | BCP (TCP/HA 80/20) 1000-1700 μm + ABGS (250 μg rhBMP6 in 2.5 mL ABC) (n = 4) | Successful rebridgment and osseointegration of newly formed bone with transverse processe swas observed in 4/4 animals (100%) |

FIG. 30 Panel (A) shows Gross anatomy and MicroCT 3D reconstruction of fusion mass between transverse processes. ABGS implants with TCP (left) and BCP (right) ceramics induced formation of bone which fused with adjacent transverse processes as observed on macerated specimens (first row) and MicroCT 3D reconstructions (second row) 14 weeks after surgery. The spinal fusion was achieved with ABGS (rhBMP6/ABC) and 500-1700 μm TCP or BCP ceramics with the rhBMP6 dose of 125 (left side of each animal) or 250 μg (right side of each animal). Panel (B) shows Bone volume and CRM volume in BCS induced by ABGS containing TCP and BCP ceramic particles 14 weeks following ABGS implantation. Dots represent ABGS with 125 μg (gray dots) and 250 μg (black dots) rhBMP6.

Successful osseointegration with transverse processes was observed in all experimental groups 14 weeks following implantation (FIG. 30A). Successful spinal fusion between adjacent transverse processes was confirmed by radiological methods (MicroCT sections, 3D reconstruction and analysis; x-ray images), on histological sections, by biomechanical testing and by palpatory test of mobility of fused transverse processes. Success rate in all groups was 100% and the same result was obtained by both analysis of spinal fusion on MicroCT sections and by palpatory mobility testing.

MicroCT analysis revealed that extensive amount of newly formed bone (bone volume) was present in all experimental groups and that there was no significant difference among experimental groups regardless the chemical composition of bioceramics (biphasic bioceramics or tricalcium phosphate bioceramics) or the rhBMP6 dose (125 or 250 μg) (FIG. 30B). However, both MicroCT and histological analysis revealed that the amount of CRM was significantly lower in groups containing pure TCP than BCP (FIG. 30B). All tested formulation achieved successful posterolateral spinal fusion in rabbits and might be tested in further rabbit and sheep experiments.

Example 13—OPS-20200610/Posterolateral Spinal Fusion/Rabbit

Example 13 was conducted to investigate spinal fusion outcome 27 weeks following implantation of ABGS (rhBMP6 in autologous blood coagulum with bioceramics) in rabbit posterolateral spinal fusion (PLF) model. This experiment compared two different types of bioceramics (tri-calcium phosphate and biphasic bioceramics in TCP/HA 40/60 ratio) as well as two different particle sizes (74-420 μm and 500-1700 μm). In this example 12 New Zealand White Rabbits (lat. *Oryctolagus cuniculus*, male, 3-5 kg) were used, which were assigned to 4 experimental groups according to the experimental design listed below and presented in Table 18.

Materials & Methods

Blood samples were collected from rabbit ear marginal vein into tubes without an anticoagulant substance in a volume of 2.5 mL. In all groups 125 μg of rhBMP6 was put in blood and mixed with bioceramics (0.5 g of 500-1700 μm and 0.8 g of 74-420 μm). After blood and bioceramics were mixed, device was rotated until blood coagulation to achieve uniform distribution of bioceramic particles in blood coagulum. Spaces between transverse processes of lumbar spine were exposed and following bone decortication implants were implanted bilateraly between transverse processes of lumbar vertebrae L5-L6.

Results

Figure 31:
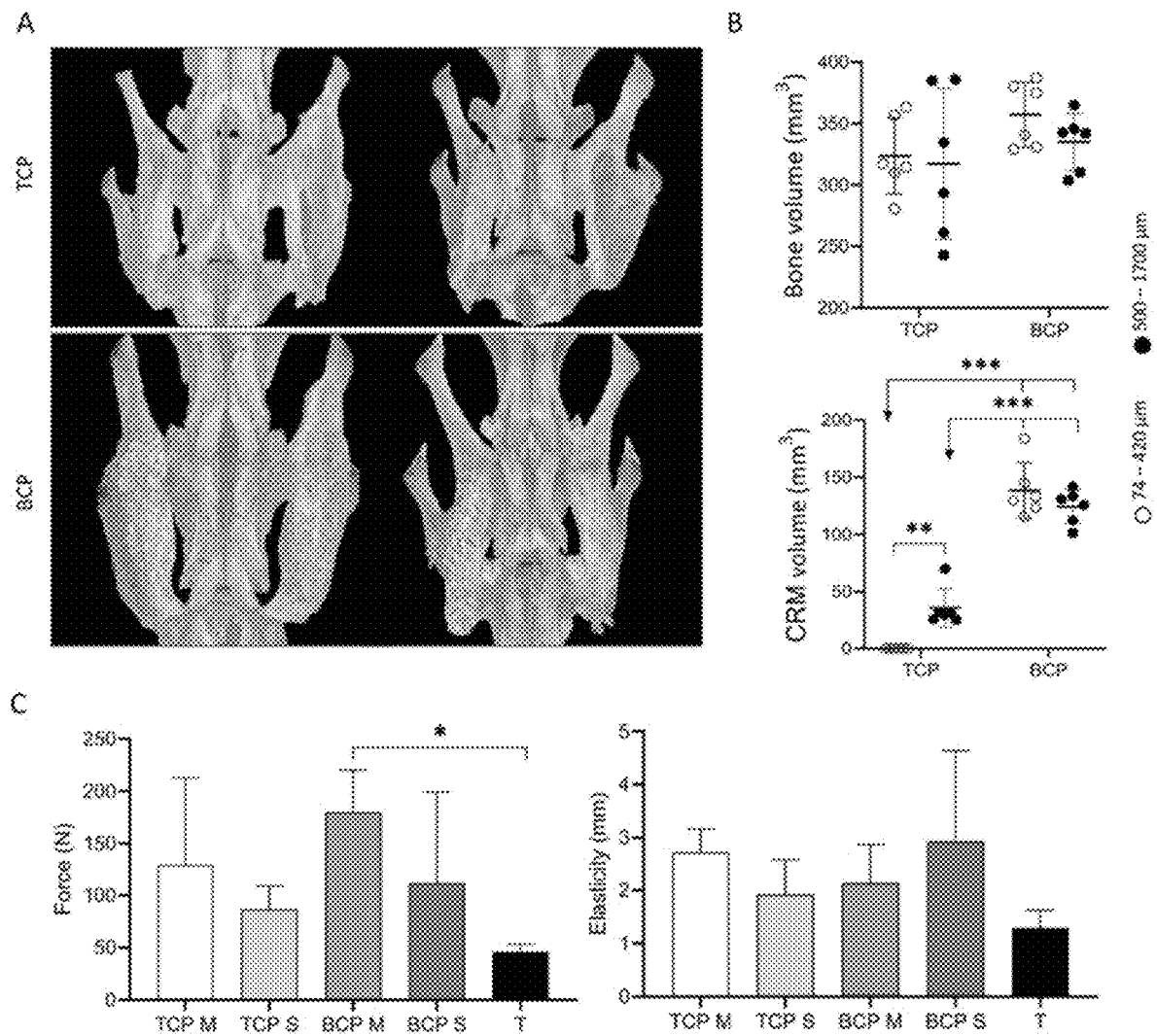
FIG. 31 Panel (A) illustrates MicroCT 3D reconstruction of fusion mass between transverse processes, Panel (B) illustrates Bone volume (first row) and CRM volume (second row) in BCS induced by ABGS with 74-420 μm (white dots) and 500-1700 μm (black dots) TCP or BCP ceramic particles, and Panel (C) illustrates Biomechanical properties of BCS containing TCP or BCP ceramic particles 27 weeks following ABGS implantation.

Results are presented in Table 18 and FIG. 31.

TABLE 18

Example 13—OPS-20200610 Groups and results

| Group | Group description | Result |
| --- | --- | --- |
| A | TCP 500-1700 μm + ABGS (125 μg rhBMP6 in 2.5 mL ABC) (n = 6) | Successful rebridgment and osseointegration of newly formed bone with transverse processes was observed in 6/6 animals (100%) |
| B | TCP 74-420 μm + ABGS (125 μg rhBMP6 in 2.5 mL ABC) (n = 6) | Successful rebridgment and osseointegration of newly formed bone with transverse processes was observed in 6/6 animals (100%) |
| C | BCP (TCP/HA 40/60) 500-1700 μm + ABGS (125 μg rhBMP6 in 2.5 mL ABC) (n = 6) | Successful rebridgment and osseointegration of newly formed bone with transverse processes was observed in 6/6 animals (100%) |
| D | BCP (TCP/HA 40/60) 74-420 μm + ABGS (125 μg rhBMP6 in 2.5 mL ABC) (n = 6) | Successful rebridgment and osseointegration of newly formed bone with transverse processes was observed in 6/6 animals (100%) |

FIG. 31 Panel (A) illustrates MicroCT 3D reconstruction of fusion mass between transverse processes. Spinal fusion was achieved with ABGS containing 125 μg rhBMP6 within ABC with TCP or BCP ceramics in two different particle sizes: 500-1700 μm (left side of each animal) or 74-420 μm (right side of each animal). Panel (B) illustrates Bone volume (first row) and CRM volume (second row) in BCS induced by ABGS with 74-420 μm (white dots) and 500-1700 μm (black dots) TCP or BCP ceramic particles. Panel (C) illustrates Biomechanical properties of BCS containing TCP or BCP ceramic particles 27 weeks following ABGS implantation. The size of particles was either 500-1700 μm (medium, M) or 74-420 μm (small, S). Transverse processes (T) were used as a control group.

Autologous bone graft substitute (ABGS) comprised of rhBMP6 in autologous blood coagulum (ABC) with small (74-420 μm) and medium (500-1700 μm) bioceramic (TCP and BCP with TCP/HA ratio 40/60) particles is effective in achieving posterolateral lumbar fusion (PLF) between adjacent transverse processes of lumbar vertebrae in rabbits.

Spinal fusion success rate in all groups was 100% and fusion was observed by radiological methods (microCT sections, 3D reconstruction and analysis; x-ray images) (FIG. 31A), by biomechanical testing and by palpatory test of mobility of fused transverse processes.

MicroCT analyses revealed that all tested ABGS formulations induced extensive amount of bone which was preserved and completely integrated with transverse processes 27 weeks following ABGS implantation (FIG. 31B). Although the bone volume was comparable between experimental groups, there was a striking difference in the CRM volume among experimental groups: TCP particles were almost completely resorbed (especially smaller, 74-420 μm particles) while BCP particles were preserved (FIG. 31B).

Example 14—OPS-20201111/Posterolateral Spinal Fusion/Sheep

Example 14 was conducted to investigate ectopic bone formation and osseointegration in rabbit posterolateral spinal fusion (PLF) model using autologous bone graft substitute (ABGS) containing rhBMP6, autologous blood coagulum (ABC) and bioceramics as compression resistant matrix (CRM). This experiment compared two different particle sizes (74-420 μm and 500-1700 μm) of calcium phosphate biphasic (BCP) bioceramics. In this example 10 Sheep (*Ovis aries*, 40-65 kg) were used, which were assigned to experimental groups according to the experimental design listed below and presented in Table 19.

Materials & Methods

Blood samples were collected from jugular vein into tubes without an anticoagulant substance in a volume of 8 mL. In all groups rhBMP6 (500 μg in the pilot and 800 μg in the main experiment) was put in blood and mixed with bioceramics (2.4 g of 74-420 μm and 1.6 g of 500-1700 μm). After blood and bioceramics were mixed, device was rotated until blood coagulation to achieve uniform distribution of bioceramic particles in the blood coagulum.

Spaces between transverse processes of lumbar spine were exposed and following bone decortication ABGS implants were implanted bilateraly between transverse processes of lumbar vertebrae L5-L6.

Results

Figure 32:
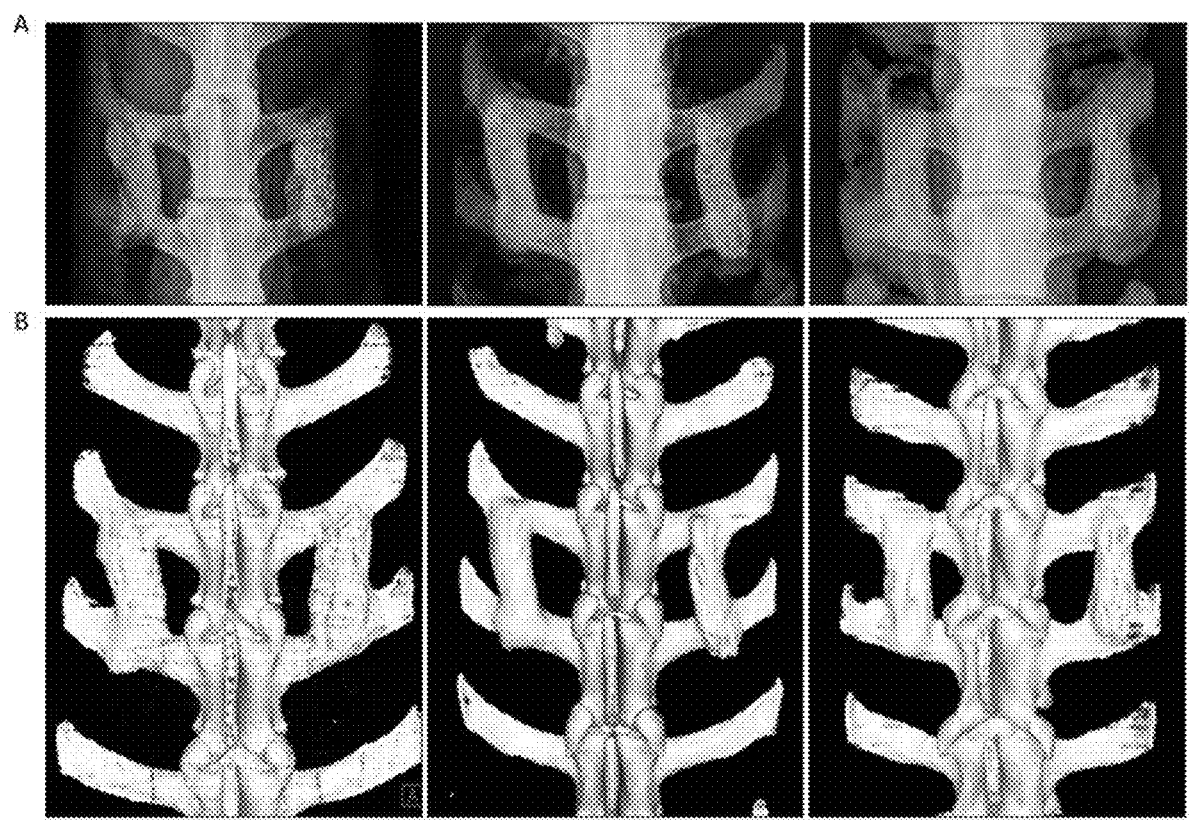
FIG. 32 are X-ray images (first row) and MicroCT 3D reconstruction of sheep lumbar spine showing successful spinal fusion between L5-L6 transverse processes.

Results are presented in Table 19 and FIG. 32.

TABLE 19

Example 14—OPS-20201111 Groups and results

| Group | Group description | Result |
|---|---|---|
| Pilot experiment | | |
| A | BCP (TCP/HA 40/60) 74-420 μm + ABGS (500 μg rhBMP6 in 8 mL ABC) (n = 1) | Successful rebridgment and osseointegration of newly formed bone with transverse processes was observed at the end of the experiment |
| B | BCP (TCP/HA 40/60) 500-1700 μm + ABGS (500 μg rhBMP6 in 8 mL ABC) (n = 1) | Successful rebridgment and osseointegration of newly formed bone with transverse processes was observed at the end of the experiment |
| Main experiment | | |
| A | BCP (TCP/HA 80/20) 74-420 μm + ABGS (800 μg rhBMP6 in 8 mL ABC) (n = 9) | Successful rebridgment and osseointegration of newly formed bone with transverse processes was observed in 9/9 animals (100%) |
| B | BCP (TCP/HA 80/20) 500-1700 μm + ABGS (800 μg rhBMP6 in 8 mL ABC) (n = 9) | Successful rebridgment and osseointegration of newly formed bone with transverse processes was observed in 8/9 animals (88.8%) |

FIG. 32 are X-ray images (first row) and MicroCT 3D reconstruction of sheep lumbar spine showing successful spinal fusion between L5-L6 transverse processes.

In this example it has been demonstrated that autologous bone graft substitute (ABGS) comprised of rhBMP6 in autologous blood coagulum (ABC) with small (74-420 μm) and medium (500-1700 μm) bioceramic (BCP with TCP/HA ratios 80/20 or 40/60) particles is effective in achieving spinal fusion in sheep posterolateral spinal fusion (PLF) model.

Formation of newly formed bone and osseointegration with native transverse processes was observed on x-ray images and CT 3D reconstructions (FIG. 32).

It will be appreciated that the application of the ABGS composition according to the present invention is not limited to use in the treatment of Posterolateral Lumbar Fusion; Anterior Lumbar Interbody Fusion, Adult Scoliosis, Trauma (Spine Reconstruction), Maxilla-cranial reconstruction or High Tibial Osteotomy, but could be applied anywhere in the human body where the ABGS composition is required.

The characteristics of the ABGS composition of the present invention, such as, inter alia, the safety; stability; and the ease of application thereof, not only overcomes the disadvantages of the prior art, but also renders the ABGS composition and the method of the invention suitable and available to a wide range of patients.

REFERENCES

1. Toth J M, Wang M, Lawson J, Badura J M, DuBose K B. Radiographic, biomechanical, and histological evaluation of rhBMP-2 in a 3-level intertransverse process spine fusion: an ovine study. Journal of neurosurgery Spine. 2016; 25(6):733-9.
2. Dimar J R, Glassman S D, Burkus K J, Carreon L Y. Clinical outcomes and fusion success at 2 years of single-level instrumented posterolateral fusions with recombinant human bone morphogenetic protein-2/compression resistant matrix versus iliac crest bone graft. Spine. 2006; 31(22):2534-9; discussion 40.
3. Lee J H, Yu C H, Yang J J, Baek H R, Lee K M, Koo T Y, et al. Comparative study of fusion rate induced by different dosages of Escherichia coli-derived recombinant human bone morphogenetic protein-2 using hydroxyapatite carrier. The spine journal: official journal of the North American Spine Society. 2012; 12(3):239-48.
4. Itoh H, Ebara S, Kamimura M, Tateiwa Y, Kinoshita T, Yuzawa Y, et al. Experimental spinal fusion with use of recombinant human bone morphogenetic protein 2. Spine. 1999; 24(14):1402-5.
5. Chu T M, Warden S J, Turner C H, Stewart R L. Segmental bone regeneration using a load-bearing biodegradable carrier of bone morphogenetic protein-2. Biomaterials. 2007; 28(3):459-67.
6. Hoffmann M F, Jones C B, Sietsema D L. Recombinant Human Bone Morphogenetic Protein-2 in Posterolateral Spinal Fusion: What's the Right Dose? Asian spine journal. 2016; 10(3):457-64.
7. Lee S H, Shin H. Matrices and scaffolds for delivery of bioactive molecules in bone and cartilage tissue engineering. Advanced drug delivery reviews. 2007; 59(4-5):339-59.
8. Akamaru T, Suh D, Boden S D, Kim H S, Minamide A, Louis-Ugbo J. Simple carrier matrix modifications can enhance delivery of recombinant human bone morphogenetic protein-2 for posterolateral spine fusion. Spine. 2003; 28(5):429-34.
9. Namikawa T, Terai H, Suzuki E, Hoshino M, Toyoda H, Nakamura H, et al. Experimental spinal fusion with recombinant human bone morphogenetic protein-2 delivered by a synthetic polymer and beta-tricalcium phosphate in a rabbit model. Spine. 2005; 30(15):1717-22.
10. Glassman S D, Dimar J R, Carreon L Y, Campbell M J, Puno R M, Johnson J R. Initial fusion rates with recombinant human bone morphogenetic protein-2/compression resistant matrix and a hydroxyapatite and tricalcium phosphate/collagen carrier in posterolateral spinal fusion. Spine. 2005; 30(15):1694-8.
11. Pelletier M H, Oliver R A, Christou C, Yu Y, Bertollo N, Irie H, et al. Lumbar spinal fusion with beta-TCP granules and variable Escherichia coli-derived rhBMP-2 dose. The spine journal: official journal of the North American Spine Society. 2014; 14(8):1758-68.
12. Louis-Ugbo J, Kim H S, Boden S D, Mayr M T, Li R C, Seeherman H, et al. Retention of 125I-labeled recombinant human bone morphogenetic protein-2 by biphasic calcium phosphate or a composite sponge in a rabbit posterolateral spine arthrodesis model. Journal of orthopaedic research: official publication of the Orthopaedic Research Society. 2002; 20(5):1050-9.
13. Suh D Y, Boden S D, Louis-Ugbo J, Mayr M, Murakami H, Kim H S, et al. Delivery of recombinant human bone morphogenetic protein-2 using a compression-resistant matrix in posterolateral spine fusion in the rabbit and in the non-human primate. Spine. 2002; 27(4):353-60.
14. Dohzono S, Imai Y, Nakamura H, Wakitani S, Takaoka K. Successful spinal fusion by E. coli-derived BMP-2-adsorbed porous beta-TCP granules: a pilot study. Clinical orthopaedics and related research. 2009; 467(12):3206-12.
15. Vukicevic S, Grgurevic L, Erjavec I, Pecin M, Bordukalo-Niksic T, Stokovic N, et al. Autologous blood coagulum is a physiological carrier for BMP6 to induce new bone formation and promote posterolateral lumbar spine 16. Boden S D, Schimandle J H, Hutton W C. 1995 Volvo Award in basic sciences. The use of an osteoinductive growth factor for lumbar spinal fusion. Part II: Study of dose, carrier, and species. Spine. 1995; 20(24):2633-44.
17. Jenis L G, Wheeler D, Parazin S J, Connolly R J. The effect of osteogenic protein-1 in instrumented and noninstrumented posterolateral fusion in rabbits. The spine journal: official journal of the North American Spine Society. 2002; 2(3):173-8.
18. Konishi S, Nakamura H, Seki M, Nagayama R, Yamano Y. Hydroxyapatite granule graft combined with recombinant human bone morphogenic protein-2 for solid lumbar fusion. Journal of spinal disorders & techniques. 2002; 15(3):237-44.
19. Minamide A, Kawakami M, Hashizume H, Sakata R, Yoshida M, Tamaki T. Experimental study of carriers of bone morphogenetic protein used for spinal fusion. Journal of orthopaedic science: official journal of the Japanese Orthopaedic Association. 2004; 9(2):142-51.
20. Lee J W, Lee S, Lee S H, Yang H S, Im G I, Kim C S, et al. Improved spinal fusion efficacy by long-term delivery of bone morphogenetic protein-2 in a rabbit model. Acta orthopaedica. 2011; 82(6):756-60.
21. Alam M I, Asahina I, Ohmamiuda K, Takahashi K, Yokota S, Enomoto S. Evaluation of ceramics composed of different hydroxyapatite to tricalcium phosphate ratios as carriers for rhBMP-2. Biomaterials. 2001; 22(12):1643-51.
22. Grgurevic L, Oppermann H, Pecin M, Erjavec I, Capak H, Pauk M, et al. Recombinant Human Bone Morphogenetic Protein 6 Delivered Within Autologous Blood Coagulum Restores Critical Size Segmental Defects of Ulna in Rabbits. JBMR plus. 2019; 3(5):e10085.
23. Jung U W, Choi S Y, Pang E K, Kim C S, Choi S H, Cho K S. The effect of varying the particle size of beta tricalcium phosphate carrier of recombinant human bone morphogenetic protein-4 on bone formation in rat calvarial defects. Journal of periodontology. 2006; 77(5):765-72.
24. Seeherman H, Wozney J M. Delivery of bone morphogenetic proteins for orthopedic tissue regeneration. Cytokine & growth factor reviews. 2005; 16(3):329-45.
25. El Bialy I, Jiskoot W, Reza Nejadnik M. Formulation, Delivery and Stability of Bone Morphogenetic Proteins for Effective Bone Regeneration. Pharmaceutical research. 2017; 34(6):1152-70.
26. Vukicevic S, Oppermann H, Verbanac D, Jankolija M, Popek I, Curak J, et al. The clinical use of bone morphogenetic proteins revisited: a novel biocompatible carrier device OSTEOGROW for bone healing. International orthopaedics. 2014; 38(3):635-47.
27. Grgurevic L, Erjavec, I.; Gupta, M.; Pecin, M.; Bordukalo-Niksic, T.; Stokovic, N., et al. Autologous blood coagulum containing rhBMP6 induces new bone formation to promote anterior lumbar interbody fusion (ALIF) and posterolateral lumbar fusion (PLF) of spine in sheep. Bone. 2020.
28. Tsuruga E, Takita H, Itoh H, Wakisaka Y, Kuboki Y. Pore size of porous hydroxyapatite as the cell-substratum controls BMP-induced osteogenesis. Journal of biochemistry. 1997; 121(2):317-24.
29. Albrektsson T, Johansson C. Osteoinduction, osteoconduction and osseointegration. European spine journal: official publication of the European Spine Society, the European Spinal Deformity Society, and the European Section of the Cervical Spine Research Society. 2001; 10 Suppl 2: S96-101.
30. Dorozhkin S V. Bioceramics of calcium orthophosphates. Biomaterials. 2010; 31(7):1465-85.
31. McKay B. Development of the first commercially available recombinant human bone morphogenetic protein (rhBMP-2) as an autograft replacement for spinal fusion and ongoing R&D direction. In: Vukicevic S & Sampath K, editor. Bone Morphogenetic Proteins: Regeneration of Bone and Beyond. Progress in Inflammation Research. Basel: Birkhauser; 2004. p. 163-85.
32. Valdes M, Moore D C, Palumbo M, Lucas P R, Robertson A, Appel J, et al. rhBMP-6 stimulated osteoprogenitor cells enhance posterolateral spinal fusion in the New Zealand white rabbit. The spine journal: official journal of the North American Spine Society. 2007; 7(3):318-25.
33. Tazaki J, Murata M, Akazawa T, Yamamoto M, Ito K, Arisue M, et al. BMP-2 release and dose-response studies in hydroxyapatite and beta-tricalcium phosphate. Biomedical materials and engineering. 2009; 19(2-3):141-6.
34. Xu H, Shimizu Y, Asai S, Ooya K. Experimental sinus grafting with the use of deproteinized bone particles of different sizes. Clinical oral implants research. 2003; 14(5):548-55.

What is claimed is:

1. An autologous bone graft substitute compostion for inducing new bone formation, promoting bone growth and treating of bone defect, wherein the composition comprises:
   (i) autologous blood;
   (ii) an osteogenic bone morphogenetic protein selected from BMP-6, BMP-2, BMP-7, BMP-4, BMP-5, BMP-8, BMP-9, BMP-12, and BMP-13, analogs thereof or heterodimers thereof, and combinations thereof, in a range of from 2 to 1000 µg per mL of autologous blood; and
   (iii) hydroxyapatite, tri-calcium phosphate, or a mixture thereof as a compression resistant matrix, the compression resistant matrix comprises particles having a particle size in the range of 74 to 420 µm,
   wherein the autologous blood forms an autologous blood coagulum comprising a fibrin-meshwork reinforced with the compression resistant matrix, the autologous blood coagulum containing the osteogenic bone morphogenetic protein, whereby the autologous blood coagulum and the compression resistant matrix provide a sustained multiphasic release of the osteogenic bone morphogenetic protein.

2. The composition according to claim 1, wherein a ratio between the compression resistant matrix and the autologous blood coagulum is from 100 to 250 mg of the compression resistant matrix per mL of the autologous blood coagulum.

3. The composition according to claim 1, wherein the ratio between the compression resistant matrix and the autologous blood coagulum is from 200 to 500 mg of the compression resistant matrix per mL of the autologous blood coagulum.

4. The composition according to claim 1, wherein the ratio between the compression resistant matrix and the autologous blood coagulum is from 50 to 500 mg of the compression resistant matrix per mL of the autologous blood coagulum.

5. The composition according to claim 1, wherein an average pore diameter of tri-calcium phosphate is in the range of from 320 to 444 µm.

6. The composition according to claim 1, wherein a total porous volume of tri-calcium phosphate is in a range of from 82 to 86%.

7. The composition according to claim 1, wherein the average pore diameter of the mixture of tri-calcium phosphate and hydroxyapatite is in the range of from 356 to 544 µm.

8. The composition according to claim 1, wherein the total porous volume of the mixture of tri-calcium phosphate and hydroxyapatite is in a range of from 86 to 89%.

9. The composition according to claim 1, wherein a ratio between tri-calcium phosphate and hydroxyapatite is 80/20.

10. The composition according to claim 1, wherein the ratio between tri-calcium phosphate and hydroxyapatite is 60/40.

11. An autologous bone graft substitute composition for inducing new bone formation, promoting bone growth and treating of bone defect, wherein the composition comprises:
i) autologous blood;
(ii) an osteogenic bone morphogenetic protein selected from BMP-6 or BMP-2, analogs thereof or heterodimers thereof, and combination thereof, in a range of 2 to 1000 µg per mL of autologous blood; and
(iii) hydroxyapatite, tri-calcium phosphate, or a mixture thereof as a compression resistant matrix, the compression resistant matrix comprises particles having a particle size in the range of 74 to 8000 µm,
wherein the autologous blood forms an autologous blood coagulum comprising a fibrin-meshwork reinforced with the compression resistant matrix, the autologous blood coagulum containing the osteogenic bone morphogenetic protein, whereby the autologous blood coagulum and the compression resistant matrix provide a sustained multiphasic release of the osteogenic bone morphogenetic protein.

12. The composition according to claim 11, wherein the particle size is in the range of from 500 to 1700 µm.

13. The composition according to claim 11, wherein the particle size is in the range of from 1700 to 2500 µm.

14. The composition according to claim 11, wherein the particle size is in the range of from 1000 to 4000 µm.

15. The composition according to claim 11, wherein BMP-6 or BMP-2 is present in the range of from 10 to 100 µg per mL of the autologous blood coagulum.

16. The composition according to claim 15, wherein BMP-6 is in the amount of 50 µg per 1 mL of the autologous blood coagulum.

17. The composition according to claim 15, wherein BMP-6 is in the amount of 100 µg per 1 mL of the autologous blood coagulum.

18. A method of inducing or promoting bone growth by treatment of a bone with an autologous bone graft substitute composition comprising:
(i) autologous blood;
(ii) an osteogenic bone morphogenetic protein selected form BMP-6, BMP-2, BMP-7, BMP-4, BMP-5, BMP-8, BMP-9, BMP-12, and BMP-13, analogs thereof or heterodimers thereof, and combinations thereof, in a range of 2 to 1000 µg per ml of autologous blood; and
(iii) hydroxyapatite, tri-calcium phosphate, or a mixture thereof as a compression resistant matrix, the compression resistant matrix comprises particles having a particle size in the range of 74 to 420 µm, or 500 to 1700 µm, or 1700 to 2500 µm, or 1000 to 4000 µm,
wherein the autologous blood forms an autologous blood coagulum comprising a fibrin-meshwork reinforced with the compression resistant matrix, the autologous blood coagulum containing the osteogenic bone morphogenetic protein, whereby the autologous blood coagulum and the compression resistant matrix provide a sustained multiphasic release of the osteogenic bone morphogenetic protein.

19. The method according to claim 18, wherein an average pore diameter of tri-calcium phosphate is in the range of from 320 to 444 µm.

20. The method according to claim 18, wherein a total porous volume of tri-calcium phosphate is in a range of from 82 to 86%.

21. The method according to claim 18, wherein the average pore diameter of the mixture of tri-calcium phosphate and hydroxyapatite is in the range of from 356 to 544 µm.

22. The method according to claim 18, wherein the total porous volume of the mixture of tri-calcium phosphate and hydroxyapatite is in a range of from 86 to 89%.

23. The method according to claim 18, wherein a ratio between tri-calcium phosphate and hydroxyapatite is 80/20 or 60/40.

24. A method of inducing or promoting bone growth by treatment of a bone with an autologous bone graft substitute composition comprising:
(i) autologous blood;
(ii) an osteogenic bone morphogenetic protein selected from BMP-6 or BMP-2, analogs thereof or heterodimers thereof, and combination thereof, in a range of 2 to 1000 µg per ml of autologous blood; and
(iii) hydroxyapatite, tri-calcium phosphate, or a mixture thereof as a compression resistant matrix, the compression resistant matrix comprises particles having a particle size in the range of 74 to 8000 µm,
wherein the autologous blood forms an autologous blood coagulum comprising a fibrin-meshwork reinforced with the compression resistant matrix, the autologous blood coagulum containing the osteogenic bone morphogenetic protein, whereby the autologous blood coagulum and the compression resistant matrix provide a sustained multiphasic release of the osteogenic bone morphogenetic protein.

25. The method according to claim 24, wherein a ratio between the compression resistant matrix and the autologous blood coagulum is from 50 to 500 mg of the compression resistant matrix per mL of the autologous blood coagulum.

26. The method according to claim 24, wherein BMP-6 or BMP-2 is present in the range of from 10 to 100 µg per mL of the autologous blood coagulum.

* * * * *